(12) United States Patent
Dictenberg et al.

(10) Patent No.: US 12,053,454 B2
(45) Date of Patent: Aug. 6, 2024

(54) COMPOSITIONS FOR CRYOPRESERVATION AND METHODS OF USE THEREOF

(71) Applicant: EVERGREEN BIOSCIENCES, New York, NY (US)

(72) Inventors: Jason Dictenberg, New York, NY (US); Pavel Iserovich, Brooklyn, NY (US)

(73) Assignee: Evergreen Biosciences, New York, NY (US)

( * ) Notice: Subject to any disclaimer, the term of this patent is extended or adjusted under 35 U.S.C. 154(b) by 0 days.

(21) Appl. No.: 16/237,442

(22) Filed: Dec. 31, 2018

(65) Prior Publication Data

US 2019/0201381 A1 Jul. 4, 2019

Related U.S. Application Data

(60) Provisional application No. 62/612,552, filed on Dec. 31, 2017.

(51) Int. Cl.
| | |
|---|---|
| *A61K 31/4166* | (2006.01) |
| *A61K 38/17* | (2006.01) |
| *A61K 38/44* | (2006.01) |
| *A61K 47/54* | (2017.01) |
| *A61P 1/18* | (2006.01) |
| *A61P 9/10* | (2006.01) |
| *A61P 25/28* | (2006.01) |

(52) U.S. Cl.
CPC ...... *A61K 31/4166* (2013.01); *A61K 38/1761* (2013.01); *A61K 38/446* (2013.01); *A61K 47/549* (2017.08); *A61P 1/18* (2018.01); *A61P 9/10* (2018.01); *A61P 25/28* (2018.01); *C12Y 115/01001* (2013.01)

(58) Field of Classification Search
CPC .............. A61K 31/4166; A61K 47/549; A61K 38/1761; A61K 38/446; A61P 9/10; A61P 25/28; A61P 1/18; C12Y 115/01001
See application file for complete search history.

(56) References Cited

U.S. PATENT DOCUMENTS

| | | | |
|---|---|---|---|
| 8,410,110 B2 | 4/2013 | Halazy et al. | |
| 2002/0042052 A1* | 4/2002 | Nilsen | C12N 9/22 536/23.1 |
| 2012/0040933 A1* | 2/2012 | Halazy | A61P 1/00 514/64 |
| 2014/0357570 A1* | 12/2014 | Vavvas | A61P 25/28 514/17.7 |
| 2015/0037783 A1* | 2/2015 | Herickhoff | C12N 5/0652 435/1.3 |
| 2016/0151442 A1 | 6/2016 | Vavvas | |
| 2016/0279190 A1 | 9/2016 | Watts et al. | |

FOREIGN PATENT DOCUMENTS

| | | |
|---|---|---|
| CN | 102307593 B | 10/2009 |
| JP | 2014-530881 A | 11/2014 |
| JP | 2003-512371 A | 3/2020 |
| WO | WO 00/19818 A1 | 4/2000 |
| WO | WO 2001-029028 | 4/2001 |
| WO | WO 2010-075561 | 7/2010 |
| WO | WO 2013-059791 | 4/2013 |
| WO | WO 2014/049022 A1 | 4/2014 |
| WO | WO 2010/075561 | 7/2020 |

OTHER PUBLICATIONS

Lyu et al (Year: 2012).*
Keller et al (Year: 1988).*
Lee et al (Year: 2014).*
PubChem CID 2828334 (Year: 2005).*
Henry et al (Year: 2016).*
Finucane et al (Year: 1999).*
Lee (Year: 2014).*
Hetz (Year: 2005).*
Bombrun (Year: 2003).*
Teng (Year: 2005).*
Keller (Year: 1998).*
Bandlien et al (Year: 1983).*
Jane et al. "Inhibition of Phosphatidylinositol 3-Kinase/AKT Signaling by NVP BKM120 Promotes ABT-737-Induced Toxicity in a Caspase-Dependent Manner through Mitochondrial Dysfunction and DNA Damage Response in Established and Primary Cultured Glioblastoma Cells" The Journal of Pharmacology and Experimental Therapeutics. Jul. 2014, vol. 350, p. 22-35.
Yao et al. "B-cell lymphoma 2 inhibitor ABT-737 induces Beclin1- and reactive oxygen species-dependent autophagy in Adriamycin-resistant human hepatocellular carcinoma cells" Tumor Biology. Mar. 29, 2017 (Mar. 29, 2017), vol. 39, p. 1-12.
International Search Report for corresponding PCT Application No. PCT/US2018/068205 date Apr. 30, 2019.
Temkin, V., Huang, Q., Liu, H., Osada, H. & Pope, R.M. (2006) Inhibition of ADP/ATP exchange in receptor-interacting protein-mediated necrosis. Mol. Cell. Biol. 26, 2215-2225.
Los, M. et al. (2002) Activation and caspase-mediated inhibition of PARP: a molecular switch between fibroblast necrosis and apoptosis in death receptor signaling. Mol. Biol. Cell 13, 978-988.

(Continued)

*Primary Examiner* — Jeffrey S Lundgren
*Assistant Examiner* — Ibrahim D Bori
(74) *Attorney, Agent, or Firm* — Mark S. Cohen; PEARL COHEN ZEDEK LATZER BARATZ LLP

(57) ABSTRACT

Provided herein are compositions for cryopreservation of mammalian cells, tissues, and organs. The compositions include a necroptosis inhibitor compound and a Bax channel inhibitor compound. Provided herein are also methods of use of the compositions, for treating, preventing, inhibiting, or reducing the incidence of cellular plasticity, or necroptosis or necrosis, of a plurality of cells, wherein the cells are brought into contact with the composition.

27 Claims, 21 Drawing Sheets

(14 of 21 Drawing Sheet(s) Filed in Color)

(56) References Cited

OTHER PUBLICATIONS

Ying W. (2013) Roles of nad, parp-1, and sirtuins in cell death, ischemic brain injury, and synchrotron radiation x-ray-induced tissue injury. Scientifica 2013:691251.
J.L. Sims, S.J. Berger, N.A. Berger. Poly(ADP-ribose) polymerase inhibitors preserve nicotinamide adenine dinucleotide and adenosine 5'-triphosphate pools in DNA-damaged cells: mechanism of stimulation of unscheduled DNA synthesis. Biochemistry, 22 (1983), pp. 5188-5194.
Karch J, Kwong JQ, Burr AR, Sargent MA, Elrod JW, Peixoto PM, Martinez-Caballero S, Osinska H, Cheng EHY, Robbins J, Kinnally KW, Molkentin JD. (2013) Bax and bak function as the outer membrane component of the mitochondrial permeability pore in regulating necrotic cell death in mice. Elife. 2013:2 ).
Karch J et al. (2015) Necroptosis Interfaces with MOMP and the MPTP in Mediating Cell Death. PLoS One 10: e01305205.
Irrinki KM, Mallilankaraman K, Thapa RJ, Chandramoorthy HC, Smith FJ, Jog NR, Gandhirajan RK, Kelsen SG, Houser SR, May MJ, Balachandran S, Madesh M. (2011) Requirement of fadd, nemo, and bax/bak for aberrant mitochondrial function in tumor necrosis factor alpha-induced necrosis. Mol Cell Biol. 31:3745-3758.
Sun L, Wang H, Wang Z, He S, Chen S, Liao D, Wang L, Yan J, Liu W, Lei X, et al. (2012) Mixed lineage kinase domain-like protein mediates necrosis signaling downstream of RIP3 kinase. Cell 148: 213-227.
Dong H., et al (2016) Cell-Permeable Peptide Blocks TLR4 Signaling and Improves Islet Allograft Survival). Cell Transplant 25:1319-29.
Giovannoni L, et al (2105) Enhancement of islet engraftment and achievement of long-term islet allograft survival by Toll-like receptor 4 blockade. Transplantation 99:29-35.
Bender and Kadenbach (2000) The allosteric ATP-inhibition of cytochrome c oxidase activity is reversibly switched on by cAMP-dependent phosphorylation. FEBS Letters 466: 130-134.
Kadenbach et al (1999) Possible Influence of Metabolic Activity on Aging. J. Anti-Aging Med. 2: 255-264.
M.L. Litsky, D.R. Pfeiffer Regulation of the mitochondrial Ca2+ uniporter by external adenine nucleotides: the uniporter behaves like a gated channel which is regulated by nucleotides and divalent cations. Biochemistry, 36: 7071-7080.
C. Giorgi, A. Romagnoli, P. Pinton, R. Rizzuto (2008) Ca2+ signaling, mitochondria and cell death. Curr. Mol. Med., 8: pp. 119-130.
M. Favaron, P. Bernardi (1985) Tissue-specific modulation of the mitochondrial calcium uniporter by magnesium ions. FEBS Lett., 183: pp. 260-264.
Bombrun et al (2003) 3,6-Dibromocarbazole Piperazine Derivatives of 2-Propanol as First Inhibitors of Cytochrome c Release via Bax Channel Modulation. Journal of Medicinal Chemistry 46(21): 4365-8.
Yoshida et al (2004) Bax-inhibiting peptide derived from mouse and rat Ku70. Biochem. Biophys. Res. Commun. 321: 961-966.
Sawatzky et al (2006) The involvement of the apoptosis-modulating proteins ERK 1/2, Bcl-xL and Bax in the resolution of acute inflammation in vivo. Am.J.Pathol. 168: 33-41.
Sawada et al. (2003) (Retraction Letter) Cytoprotective membrane-permeable peptides designed from the Bax-binding domain of Ku70. Nat Cell Biol. Apr. 2003;5(4):352-7.
Peixoto et al (2009) MAC inhibitors suppress mitochondrial apoptosis. Biochem.J. 423: 381-387.
Zheng et al (2012) NAD(+) administration decreases ischemic brain damage partially by blocking autophagy in a mouse model of brain ischemia. Neurosci Lett. Mar. 23, 2012;512(2):67-71.
Ying et al (2007) Intranasal administration with NAD+ profoundly decreases brain injury in a rat model of transient focal ischemia. Front Biosci., 12:2728-34.

Katsumi Shibata & Kazumi Tanaka (1986) Simple Measurement of Blood NADP and Blood Levels of NAD and NADP in Humans, Agricultural and Biological Chemistry, 50: 2941-2942.
Wang et al (2014) P7C3 Neuroprotective Chemicals Function by Activating the Rate-Limiting Enzyme in NAD Salvage. Cell 158: 1324-1334.
Peixoto et al . Mitochondrial Apoptosis-Induced Channel (MAC) Function Triggers a Bax/Bak-Dependent Bystander Effect. Am J Pathol. Jan. 2011; 178(1): 48-54.
Garg et al (2010) Immunogenic cell death, DAMPs and anticancer therapeutics: an emerging amalgamation. Biochem. Biophys. Acta 1805: 53-71.
Lin J.H., Weigel H., Cotrina M.L., Liu S., Bueno E., Hansen A.J., Hansen T.W., Goldman S., Nedergaard M. Gap-junction-mediated propagation and amplification of cell injury. Nat Neurosci. 1998;1:494-500.
V. Nikoletopoulou, M.Markaki, K. Palikaras, N. Tavernarakis (2013) Crosstalk between apoptosis, necrosis and autophagy. Biochem. Biophys. Acta 1833: 3448-3459.
Majno G, Joris I. (1995) Apoptosis, oncosis, and necrosis. An overview of cell death. Am J Pathol. 146: 3.
Festjens N, Vanden Berghe T, Vandenabeele P. (2006) Necrosis, a well-orchestrated form of cell demise: Signalling cascades, important mediators and concomitant immune response. BBA Bioenergetics Biochem. Biophys. Acta 1757:1371-1387.
Cohen G. (1997) Caspases: The executioners of apoptosis. Biochem J. 326:1-16.
Skulachev V. (2006) Bioenergetic aspects of apoptosis, necrosis and mitoptosis. Apoptosis 11:473-485.
Vieira et al. (2014) Ischemic insults induce necroptotic cell death in hippocampal neurons through the up-regulation of endogenous RIP3. Neurobiol Dis. 68: 26-36.
Linkermann et al. (2012) Rip1 mediates necroptosis and contributes to renal ischemia/reperfusion injury. Kidney Int. 81:751-61.
Rosenbaum DM, Degterev A, David J, Rosenbaum PS, Roth S, Grotta JC, Cuny GD, Yuan J, Savitz SI. (2010) Necroptosis, a novel form of caspase-independent cell death, contributes to neuronal damage in a retinal ischemia-reperfusion injury model. J Neurosci Res. 88:1569-1576.
Halestrap AP. (2009) What is the mitochondrial permeability transition pore? J Mol Cell Cardiol. 46:821-831.
Broekemeier KM, Dempsey ME, Pfeiffer DR. (1989) Cyclosporin A is a potent inhibitor of the inner membrane permeability transition in liver mitochondria. J Biol Chem 264:7826-7830.
Baines CP, Kaiser RA, Purcell NH, Blair NS, Osinska H, Hambleton MA, Brunskill EW, Sayen MR, Gottlieb RA, Dorn GW, Robbins J, Molkentin JD. (2005) Loss of cyclophilin D reveals a critical role for mitochondrial permeability transition in cell death. Nature 434:658-662.
Schinzel AC, Takeuchi O, Huang Z, Fisher JK, Zhou Z, Rubens J, Hetz C, Danial NN, Moskowitz MA, Korsmeyer SJ. (2005) Cyclophilin D is a component of mitochondrial permeability transition and mediates neuronal cell death after focal cerebral ischemia. Proc Natl Acad Sci USA. 102:12005-12010.
Nakagawa T, Shimizu S, Watanabe T, Yamaguchi O, Otsu K, Yamagata H, Inohara H, Kubo T, Tsujimoto Y. (2005) Cyclophilin D-dependent mitochondrial permeability transition regulates some necrotic but not apoptotic cell death. Nature 434:652-658.
Millay DP, Sargent MA, Osinska H, Baines CP, Barton ER, Vuagniaux G, Sweeney HL, Robbins J, Molkentin JD. (2008) Genetic and pharmacologic inhibition of mitochondrial-dependent necrosis attenuates muscular dystrophy. Nat Med. 14:442-447.
Ramachandran A, Lebofsky M, Baines CP, Lemasters JJ, Jaeschke H. (2011) Cyclophilin D deficiency protects against acetaminophen-induced oxidant stress and liver injury. Free Radic Res. 45:156-164.
Lim S, Davidson S, Mocanu M, Yellon D, Smith C. (2007) The cardioprotective effect of necrostatin requires the cyclophilin-D component of the mitochondrial permeability transition pore. Cardiovasc Drugs Ther. 21:467-469.
Nazareth W, Yafei N, Crompton M. (1991) Inhibition of anoxia-induced injury in heart myocytes by cyclosporin a. J Mol Cell Cardiol. 23:1351-1354.

(56) References Cited

OTHER PUBLICATIONS

C. Garrido, L. Galluzzi, M. Brunet, P.E. Puig, C. Didelot, G. (2006) Kroemer, Mechanisms of cytochrome c release from mitochondria, Cell Death Differ. 13: 1423-1433.
M. Krajewska, J.K. Mai, J.M. Zapata, K.W. Ashwell, S.L. Schendel, J.C. Reed, S. Krajewski. (2002) Dynamics of expression of apoptosis-regulatory proteins Bid, Bcl-2, Bcl-X, Bax and Bak during development of murine nervous system, Cell Death Differ. 9: 145-157.
I. Liste, E. Garcia-Garcia, C. Bueno, A. Martinez-Serrano (2007) Bcl-XL modulates the differentiation of immortalized human neural stem cells, Cell Death Differ. 14: 1880-1892.
M.Y. Chang, W. Sun, W. Ochiai, K. Nakashima, S.Y. Kim, C.H. Park, J.S. Kang, J.W. Shim, A.Y. Jo, C.S. Kang, Y.S. Lee, J.S. Kim, S.H. Lee (2007) Bcl-XL/Bax proteins direct the fate of embryonic cortical precursor cells, Mol. Cell. Biol. 27: 4293-4305.
K.M. Wright, M.W. Linhoff, P.R. Potts, M. Deshmukh (2004) Decreased apoptosome activity with neuronal differentiation sets the threshold for strict IAP regulation of apoptosis, J. Cell. Biol. 167: 303-313.
S. Sola, M.M. Aranha, C.M. Rodrigues (2012) Driving apoptosis-relevant proteins toward neural differentiation, Mol. Neurobiol. 46: 316-331.
M.M. Aranha, S. Sola, W.C. Low, C.J. Steer, C.M. Rodrigues (2009) Caspases and p53 modulate FOXO3A/Id1 signaling during mouse neural stem cell differentiation. J. Cell. Biochem. 107: 748-758.
D.M. Santos, J.M. Xavier, A.L. Morgado, S. Sola, C.M. Rodrigues (2012) Distinct regulatory functions of calpain 1 and 2 during neural stem cell self-renewal and differentiation. PLoS One 7: e33468.
Sola S, Morgado AL, Rodrigues CM. (2013) Death receptors and mitochondria: two prime triggers of neural apoptosis and differentiation. Biochim Biophys Acta. 1830: 2160-6.
C. Parker, G. Acsadi, C.A. Brenner (2009) Mitochondria: determinants of stem cell fate? Stem Cells Dev. 18: 803-806.
M. McBride, M. Neuspiel, S. Wasiak (2006) Mitochondria: more than just a powerhouse, Curr. Biol. 16: R551-R560.
S. Mandal, A.G. Lindgren, A.S. Srivastava, A.T. Clark, U. Banerjee (2011) Mitochondrial function controls proliferation and early differentiation potential of embryonic stem cells, Stem Cells 29: 486-495.
W. Wang, P. Osenbroch, R. Skinnes, Y. Esbensen, M. Bjoras, L. Eide (2010) Mitochondrial DNA integrity is essential for mitochondrial maturation during differentiation of neural stem cells, Stem Cells 28: 2195-2204.
M. Cozzolino, E. Ferraro, A. Ferri, D. Rigamonti, F. Quondamatteo, H. Ding, Z.S. Xu, F. Ferrari, D.F. Angelini, G. Rotilio, E. Cattaneo, M.T. Carri, F. Ceccon (2004) Apoptosome inactivation rescues proneural and neural cells from neurodegeneration, Cell Death Differ. 11: 1179-1191.
R. Behjati, K. Kawai, Y. Inadome, J. Kano, H. Akaza, M. Noguchi (2011) APAF-1 is related to an undifferentiated state in the testicular germ cell tumor pathway, Cancer Sci. 102: 267-274).
W. Wang, Y. Esbensen, D. Kunke, R. Suganthan, L. Rachek, M. Bjoras, L. Eide (2011) Mitochondrial DNA damage level determines neural stem cell differentiation fate, J. Neurosci. 31: 9746-9751.
A.J. Trevelyan, D.M. Kirby, T.K. Smulders-Srinivasan, M. Nooteboom, R. Acin-Perez, J.A. Enriquez, M.A. Whittington, R.N. Lightowlers, D.M. Turnbull (2010) Mitochondrial DNA mutations affect calcium handling in differentiated neurons, Brain 133: 787-796.
Vanden Berghe et al.(2006) Necrptotic cells, but not apoptotic cells, secrete IL-6, which can function as an alarmin Necrosis is associated with IL-6 production but apoptosis is not. Cell. Signal. 18: 328-335.
P. Lassus, X. Opitz-Araya, Y. Lazebnik. Requirement for caspase-2 in stress-induced apoptosis before mitochondrial permeabilization. Science, 297 (2002), pp. 1352-1354.
SJ Kim et al. "Caspase blockade induces RIP3-mediated programmed necrosis in Toll-like receptor-activated microglia" Cell Death and Disease (2013) 4, e716; doi:10.1038/cddis.2013.238; published online Jul. 11, 2013 Subject Category: Neuroscience p. 1-12.
Y T Wu et al. "zVAD-induced necroptosis in L929 cells depends on autocrine production of TNFa mediated by the PKC-MAPKs-AP-1 pathway" Cell Death and Differentiation (2011) 18, 26-37; doi:10.1038/cdd.2010.72; published online Jun. 11, 2010 p. 26-37.
Christophe Lemaire et al "Inhibition of caspase activity induces a switch from apoptosis to necrosis" Institut de Biochimie, CNRS ERS 0571, Baêt. 430, Universiteè Paris-Sud, 91405 Orsay, France Received Jan. 17, 1998 p. 266-270.
European Search Report for corresponding European Application No. 18895402.8 date Aug. 31, 2021.
Davidson et al.. "Cardioprotective actions of necrostatin" Abstract Journal of Molecular and Cellular Cardiology 42 (2007).
Arnoult et al. "Caspase inhibition prevents the mitochondrial release of apoptosis-inducing factor" Cell Death and Differentiation (2003) 10, 845-849.
Kroemer et al. "Classification of cell death: recommendations of the Nomenclature Committee on Cell Death 2009" Cell Death and Differentiation (2009) 16, 3-11; doi:10.1038/cdd.2008.150; published online Oct. 10, 2008.
Jagtap et al. "Structure-Activity Relationship Study of Tricyclic Necroptosis Inhibitors" J. Med. Chem. 2007, 50, 1886-1895.
Wang et al. "Necrostatin-1 Suppresses Autophagy and Apoptosis in Mice Traumatic Brain Injury Model" Neurochem Res (Published Jun. 27, 2012) 37:1849-1858.
Teng et al. "Structure-activity relationship study of novel necroptosis inhibitors" Bioorganic & Medicinal Chemistry Letters 15 (2005) 5039-5044.
Search Report for corresponding Sigaporean Application No. 11202006304S date Jun. 1, 2021.
Office Action for corresponding Saudian Arabian application No. 520412361 dated May 26, 2022.
Esther P. Jane, Daniel R. Premkumar, Alejandro Morales, Kimberly A. Foster and Ian F. Pollack Journal of Pharmacology and Experimental Therapeutics; Jul. 2014, 350 (1) 22-35.
Mi-Ae Lyu et al. Bax345/BLyS: A novel, completely human fusion protein targeting malignant B cells and delivering a unique mitochondrial toxin, Cancer Letters, vol. 322, Issue 2, 2012, p. 159-168.
Office Action for corresponding Japanes Application No. 2020-555745 dated Jan. 16, 2023.
Office Action for corresponding Israeli Appliation No. 275739 dated Feb. 15, 2023.
Office Action for corresponding chinese Application No. 201880087753.7 dated Feb. 16, 2023.
Takahashi et al. "Necrostatin-1 analogues: critical issues on the specificity, activity and in vivo use in experimental disease models" Citation: Cell Death and Disease (2012).
Lee et al. "Effect of necrostatin on mouse ovarian cryopreservation and transplantation" Jung Ryeol Lee et al. European Journal of Obstetrics & Gynecology and Reproductive Biology 178 (2014) 16-20.
M Kunitz "Crystalline desoxyribonuclease i. Isolation and general properties spectrophotometric method for the measurement op desoxyribonuclease activity" Obstetrics & Gynecology and Reproductive Biology, vol. 178, pp. 16-20 Downloaded from http:/rupress.org/jgp/article pdf/33/4/349/1240450/349.pdf by guest on Mar. 8, 2023.
Jane et al., "Inhibition of Phosphatidylinositol 3-Kinase/AKT Signaling by NVP-BKM120 Promotes ABT-737-Induced Toxicity in a Caspase-Dependent Manner through Mitochondrial Dysfunction and DNA Damage Response in Established and Primary Cultured Glioblastoma Cells", The Journal of Pharmacology and Experimental Therapeutics, (Jul. 00, 2014), vol. 350, pp. 22-35.
Hetz et al. "Bax Channel Inhibitors Prevent Mitochondrion-mediated Apoptosis and Protect Neurons in a Model of Global Brain Ischemia" The Journal of Biological Chemistry, vol. 280, No. 52, pp. 42960-42970.
Bombrun et al. "3,6-Dibromocarbazole Piperazine Derivatives of 2-Propanol as First Inhibitors of Cytochrome c Release via Bax Channel Modulation," Journal of Medicinal Chemistry, vol. 46, No. 21, pp. 4365-4368.

(56) References Cited

OTHER PUBLICATIONS

Dejean et al "MAC and Bcl-2 family proteins conspire in a deadly plot" *Biochim Biophys Acta.* 2010 ; 1797(6-7): 1231-1238. doi:10.1016/j.bbabio.2010.01.007.
Office Action for corresponding IN application No. 202017033017 dated Mar. 1, 2023.
Davidson et al, "Cardioprotective actions of necrostatin", Journal of Molecular and Cellular Cardiology, Academic Press, GB, (May 25, 2007), vol. 42, No. 6, doi:10.1016/J.YJMCC.2007.03.586, ISSN 0022-2828, p. S193 (2007).
Chang P, Dong W, Zhang M, et al. (2014) Anti-necroptosis chemical necrostatin-1 can also suppress apoptotic and autophagic pathway to exert neuroprotective effect in mice intracerebral hemorrhage model. J Mol Neurosci 52:242-249.
Y. Wang, H. Wang, Y. Tao, S. Zhang, J. Wang, X. Feng,. Necroptosis inhibitor necrostatin-1 promotes cell protection and physiological function in traumatic spinal cord injury, Neuroscience, vol. 266, 2014, pp. 91-101.
Nikseresht, S., Khodagholi, F., Nategh, M et al. RIP1 Inhibition Rescues from LPS-Induced RIP3-Mediated Programmed Cell Death, Distributed Energy Metabolism and Spatial Memory Impairment. J Mol Neurosci 57, 219-230 (2015).
Jie H, He Y, Huang X, Zhou Q, Han Y, Li X, Bai Y, Sun E. Necrostatin-1 enhances the resolution of inflammation by specifically inducing neutrophil apoptosis. Oncotarget. Apr. 12, 2016;7(15):19367-81.
Ning, Yichun, et al. "Necrostatin-1 attenuates cisplatin-induced nephrotoxicity through suppression of apoptosis and oxidative stress and retains klotho expression." Frontiers in pharmacology 9 (2018): 384.
Office Action for corresponding Arab Emirates Application No. P6000983-2020 dated Dec. 18, 2023.
Jeffrey N. Keller et al., "Mitochondrial manganese superoxide dismutase prevents neural apoptosis and reduces ischemic brain injury: suppression of peroxynitrite production, lipid peroxidation, and mitochondrial dysfunction", Journal of Neuroscience, 1998, vol. 18, No. 2, pp. 687-697.
Lue et al., "Authophagy is involved in Traumatic Brain Injury-Induced cell Death and Contributes to Functional outcome deficits in mice" Journal of Neuroscience, 2011, vol. 184 pp. 54-63.
Fox et al. "Neutrophil apoptosis: relevance to the innate immune response and inflammatory disease" Journal of Innate Immunity, 2010,2:216-227.
Dubey et al. "Nitric oxide-mediated apoptosis of neutrophils through caspase-8 and caspase-3-dependent mechanism" Citation: Cell Death and Disease (2016) 7, e2348, doi:10.1038/cddis 2016.248. Official journal of the Cell Death Differentiation Association pp. 1-12.
Juergensmeier Juliane et al Bax directly induces release cytochrome c from isolated mitochondria 1998-pnas.95.9.4997.
Office Action for corresponding CN application No. 201880087753.7 dated Feb. 16, 2023.
Jung Ryeol Lee et al. European Journal of Obstetrics & Gynecology and Reproductive Biology 178 (2014) 16-20.
NEC-2-pubchem.ncbi.nlm.nih.gov-2023-07-13.
Office Action for corresponding Japanese application No. 202-555745 dated Sep. 25, 2023.
Office Action for corresponding Singapore application No. 11202006304S.
Robert Eskes et al. "Bax-induced Cytochrome C Release from Mitochondria Is Independent of the Permeability Transition Pore but Highly dependent on $Mg^{2+}$ Ions." The Rockefeller University Press, 0021-9525/98/10/217/8. The Journal of Cell Biology, vol. 143, No. 1, Oct. 5, 1998 217-224 http://www.jcb.org.

* cited by examiner

Nox1 cell staining

Uridine Staining
(Arbitrary Units)

COMPOSITIONS FOR CRYOPRESERVATION AND METHODS OF USE THEREOF

CROSS-REFERENCE TO RELATED APPLICATION

This application claims priority to U.S. Provisional Patent Application 62/612,552, filed Dec. 31, 2017, which is incorporated by reference herein in its entirety.

FIELD OF INTEREST

Compositions and methods thereof for cryopreservation of mammalian cells, tissues, and organs are described herein.

BACKGROUND

Excessive cell death is a major barrier to the clinical use of cells, tissues, and organs obtained from a live donor, or cells grown in culture. This problem is particularly acute when there is a protracted time period between procuring cells and using them, requiring that the cells be stabilized during prolonged storage. Generally, the process of isolation of donor cells, tissues or organs damages cells in and of itself, as it involves enzymatic or mechanical removal, enzymatic digestion of extracellular proteins, cell transferring between vessels, centrifugation, resuspension in solutions, and filtration steps. Cells can also suffer significant damage during seeding into growth chambers, a process termed trituration. Routine cell manipulation in vitro is likewise a major source of cell damage. Cells in culture are routinely separated from the matrices on which they grow to allow for further amplification of cell numbers and subsequent growth, for procedural manipulation to introduce experimental treatments such as DNA introduction, and routine measurements downstream, which require cells to first be removed from their environment. These procedures often disrupt the integrity of the outer membrane of many cells, causing punctures and ruptures. Such physical damage to the cells causes metabolites to leak from their cytoplasm and into the surrounding extracellular space. On the physiological level, damage to plasma membrane integrity results in excess calcium release within cells, decreased ATP concentrations, decreased NAD concentrations, and activation of pathways that lead to necrosis and necroptosis.

In addition, the isolated cells, tissues, and organs suffer physiological damage due to interruption of circulation which leaves the cells within removed tissues and organs at significant risk of lack of oxygenation, free radical generation, and ischemia. These insults rapidly lead to necrosis and necroptosis within cells in the tissue, resulting in excessive cell death, especially for primary cells derived from animal or human tissue, ultimately leaving insufficient material for subsequent clinical use. It has also been long appreciated that these necrotic cells spill their contents onto neighboring cells and cause them to signal death from the outside. The spilling of these cellular components, characterized as damage-associated molecular patterns (DAMPS), activates an immunogenic response whereby these molecules themselves can activate pattern-recognition receptors and cause neighboring cells to activate necroptosis as a response to perceived inflammation. Furthermore, the cells that do survive may undergo de-differentiation, a process of reversion of committed or differentiated cells with less capacity into ones with greater differentiative capacity.

Physiological damage can be prevented in part through slowing down or halting of cell metabolism during times of stress. One approach is to hold cells and tissues, as well as organs for transplant, at hypothermic temperatures during the period between isolation and later use. Another option for halting cell metabolism and any resultant oxidative damage, which is available in the case of cell cultures and individual cells, is preserving cells at subfreezing temperatures, a process called cryopreservation. However, cryopreservation itself and freeze-thaw cycles associated with cryopreservation, cause damage to cells through ice crystal formation in the immediate vicinity of the cells and, sometimes, within cells, again causing punctures and ruptures of external plasma membrane and of internal organelles (so-called to freeze-thaw damage). The combination of isolation and cryopreservation-associated cell damage can also result in the trans-differentiation of cells from one differentiated state into another cell type, or dedifferentiation of cells, thereby further complicating subsequent use of any isolated cells.

Current methods do not address the ensuing cell damage and death due to these insults, and leave cells and tissues and organs with excessive damage. Additionally, no solutions have been implemented to stop the ensuing necrosis. Likewise, few advances, if any, have led to improvement in cryopreservation techniques, and it is not understood what molecular pathways exactly lead to cell death upon freeze-thaw processes.

Thus, there is an ongoing need for a method of isolating and or storing tissues, cells, and organs that avoids necrosis, necroptosis and de-differentiation stemming from physical and physiological damage the cells suffer in the process of isolation. Further, there is an ongoing need for a method of cryopreserving cells that avoids necrosis, necroptosis and de-differentiation stemming from physical and physiological damage the cells suffer in the process of cryopreservation. Finally, there is an ongoing need for a reducing cellular plasticity, necroptosis, or necrosis that results from physical and physiological damage cells incur in the course of cell manipulations in vitro, during liberation from tissue.

The composition and methods thereof disclosed herein addresses these needs, wherein use of the composition may reduce the incidence of necroptosis or necrosis during cryopreservation, and may treat, prevent, inhibit, or reduce the incidence of cellular plasticity in a plurality of cells.

SUMMARY

In one aspect, disclosed herein is a composition comprising a necroptosis inhibitor and a. Bax channel inhibitor. In another aspect, the necroptosis inhibitor comprises a 5-((7-Chloro-1H-indol-3-yl)methyl)-3-methyl-2,4-imidazolidin-edione compound or an analog, derivative, isomer, or pharmaceutically acceptable salt thereof, and the Bax channel inhibitor comprises a 3,6-Dibromo-a-(1-piperazinylmethyl)-9H-carbazole-9-ethanol dihydrochloride compound, or an analog, derivative, isomer, or pharmaceutically acceptable salt thereof.

In a related aspect, a necroptosis inhibitor comprises a 3-p-Methoxyphenyl-5,6-tetramethylenothieno[2,3-d]pyrimidin-4-one-2-mercaptoethylcyanide compound, a (Z)-5-((3-(4-Fluorophenyl)-1-H-pyrazol-4-yl)methylene)-2-imino-3-(thiazol-2-yl)thiazolidin-4-one compound, a 5-(Indol-3-ylmethyl)-(2-thio-3-methyl)hydantoin compound, 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound, (S)—N-(1)-[2-chloro-6- fluorophenyl]ethyl)-5-cyano-1-methyl-1H-pyrrole-2-carboxamide compound, methyl-thiohydantoin-tryptophan compound, (E)-N-(4-(N-(3-Methoxypyrazin-2-yl)sulfamoyl)phenyl)-3-(5-nitrothiophene-2-yl)acrylamide compound, 1-(4-(4-Arninofuro[2,3-d]pyrimidin-5-yl)phenyl)-3-(2-fluoro-5-(trifluoromethyl)phenyl)urea compound, or 2,2-dimethyl-1-(5(S)-phenyl-4,5-dihydro-pyrazol-1-yl)-propan-1-one compound, or an analog, derivative, isomer, or pharmaceutically acceptable salt of said necroptosis inhibitor compound.

In another related aspect, the concentration of the 5-((7-Chloro-1H-indol-3-yl)methyl)-3-methyl-2,4-imidazolidinedione compound or said analog, derivative, isomer, or pharmaceutically acceptable salt thereof is about 0.2 nM-2 µM. In another related aspect, the concentration of said 3,6-Dibromo-α-(1-piperazinylmethyl)-9H-carbazole-9-ethanol dihydrochloride compound, or analog, derivative, isomer, or pharmaceutically acceptable salt thereof is about 0.5 nM-50 µM.

In another aspect, a composition disclosed herein further comprises a nicotinamide adenine dinucleotide (NAD), an adenosine triphosphate (ATP), a cyclosporin A, or a superoxide dismutase, or any combination thereof. In a related aspect, the superoxide dismutase comprises a manganese superoxide dismutase or a zinc superoxide dismutase. In another related aspect, the concentration of said NAD is about 5 nM-500 µM. In another related aspect, the concentration of said ATP is about 10 nM-1 mM. In another related aspect, the concentration of said cyclosporin A is about 1 nM-1 nM. In another related aspect, the concentration of said superoxide dismutase is about 0.001-100 Kunitz Units (KU).

In another aspect, a composition disclosed herein comprises about 20 nM 5-((7-Chloro-1H-indol-3-yl)methyl)-3-methyl-2,4-imidazolidinedione), about 5 nM 3,6-Dibromo-a-(1-piperazinylmethyl)-9H-carbazole-9-ethanol dihydrochloride, about 0.05 mM nicotinamide adenine dinucleotide (NAD), about 0.01 µM adenosine triphosphate (ATP), about 0.01 µM cyclosporin A, and about 0.1 Kunitz Unit manganese superoxide dismutase or zinc superoxide dismutase.

In a related aspect, a composition described herein further comprises a cryoprotective agent. In another related aspect, the cryoprotective agent comprises DMSO, or serum, or any combination thereof.

In a related aspect, a composition described herein further comprises a pharmaceutically acceptable excipients or carriers.

In one aspect, disclosed herein is a method of cryopreservation, the method comprising the steps of: bringing a plurality of cells in contact with a composition comprising a necroptosis inhibitor and a Bax channel inhibitor; and cooling the composition comprising the plurality of cells of step (a), wherein the necroptosis inhibitor comprises a 5-((7-chloro-1H-indol-3-yl)methyl)-3-methyl-2,4-imidazolidinedione compound or an analog, derivative, isomer, or pharmaceutically acceptable salt thereof, and wherein the Bax channel inhibitor comprises 3,6-dibromo-α-(1-piperazinylmethyl)-9H-carbazole-9-ethanol dihydrochloride or an analog, derivative, isomer, or pharmaceutically acceptable salt thereof.

In one aspect, disclosed herein is a method of treating, preventing, inhibiting, or reducing the incidence of cellular plasticity, or necroptosis or necrosis in a plurality of cells, said method comprising the step of: bringing said plurality of cells in contact with a composition comprising a necroptosis inhibitor and a Bax channel inhibitor, wherein the necroptosis inhibitor comprises a 5-((7-chloro-1H-indol-3-yl)methyl)-3-methyl-2,4-imidazolidinedione compound or an analog, derivative, isomer, or pharmaceutically acceptable salt thereof, and wherein the Bax channel inhibitor comprises 3,6-dibromo-α-(1-piperazinylmethyl)-9H-carbazole-9-ethanol dihydrochloride or an analog, derivative, isomer, or pharmaceutically acceptable salt thereof.

In a related aspect, the necroptosis or necrosis is associated with aging or disease. In another related aspect, the disease is myocardial infarction, diabetes secondary to beta-cell necroptosis, cholestatic liver disease, stroke, organ ischemia, ischemia-reperfusion injury, liver disease, necrosis from cancer chemotherapy or radiation therapy, traumatic brain injury, necrotizing pancreatitis, pathogen-induced necroptosis, inflammation, or neurodegenerative disease.

In a related aspect, the treating, preventing, inhibiting, or reducing the incidence of cellular plasticity, or necroptosis or necrosis, comprises in vitro or in vivo treating, preventing, inhibiting, or reducing the incidence of cellular plasticity, necroptosis, or necrosis. In another related aspect, the plurality of cells comprises tissue culture cells, primary cells, egg cells, a tissue, or an organ or a portion thereof, or any combination thereof. In another related aspect, the tissue culture cells or primary cells comprise stem cells, adult cells, transdifferentiated cells, dedifferentiated cells, or differentiated cells, or any combination thereof. In another related aspect, the plurality of cells comprises human cells or animal cells. In another related aspect, the bringing in contact is in vivo, ex vivo, or in vitro. In another related aspect, the bringing in contact in vivo or ex vivo comprises perfusion of an animal or a portion thereof, an organ or a portion thereof, or a tissue. In another related aspect, the perfusion is cardiac perfusion. In another related aspect, the bringing in contact in vitro comprises immersing said plurality of cells in said composition, supplementing a growth media of said plurality of cells with said composition, perfusing said plurality of cells with said composition via non-thermal reversible electroporation, or perfusing said plurality of cells with said composition in a bioreactor.

In a related aspect, methods disclosed herein further comprise a step of physical, chemical, or thermodynamic manipulation of said plurality of cells. In a related aspect, the thermodynamic manipulation comprises heating or cooling said plurality of cells. In a related aspect, the cooling comprises cryopreservation or a freeze-thaw cycle, or a combination thereof.

In a related aspect, methods disclosed herein prevent, inhibit, or reduce necrosis or necroptic death of said plurality of cells during said cryopreservation or a freeze-thaw cycle thereof, compared with an uncontacted plurality of cells.

In a related aspect, the methods disclosed herein protect said plurality of cells from physical damage during said cryopreservation or freeze-thaw cycles thereof. In another related aspect, the methods enhance growth potential of said plurality of cells during cryopreservation compared with uncontacted cells. In another related aspect, the methods prevent oxidative damage to said plurality of cells during cryopreservation or freeze-thaw cycles thereof. In another related aspect, the methods prevent ischemia of said cells during cryopreservation or freeze-thaw cycles thereof. In another related aspect, the methods inhibit necrosis pathway signaling. In another related aspect, the methods prevent, inhibit, or reduce changes in the differentiation state of said cells, thereby stabilizing the identity of said cells compared with uncontacted cells. In another related aspect, the methods induce a state of metabolic suspension in said cells. In another related aspect, the metabolic suspension comprises reversible cessation of oxygen metabolism. In another related aspect, the methods improve viability or latent viability of said cells compared with an uncontacted plurality of cells.

In another aspect, in methods disclosed herein the necroptosis inhibitor compound comprises a 3-p-Methoxyphenyl-5,6-tetramethylenothieno[2,3-d]primidin-4-one-2-mercaptoethylcyanide compound, a (Z)-5-((3-(4-Fluorophenyl)-1H-pyrazol-4-yl)methylene)-2-imino-3-(thiazol-2-yl) thiazolidin-4-one, a 5-(Indol-3-ylmethyl)-(2-thio-3-methyl) hydantoin, a methyl-thiohydantoin-tryptophan compound, a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone, a (S)—N-(1-[2-chloro-6-fluorophenyl] ethyl)-5-cyano-1-methyl-1H-pyrrole-2-carboxamide, a (E)-N-(4-(N-(3-Methoxypyrazin-2-yl)sulfamoyl)phenyl)-3-(5-nitrothiophene-2-yl)acrylamide, a 1-(4-(4-Aminofuro[2,3-d] pyrimidin-5-yl)phenyl)-3-(2-fluoro-5-(trifluoromethyl) phenyl)urea, or a 2,2-dimethyl-1-(5(S)-phenyl-4,5-dihydro-pyrazol-1-yl)-propan-1-one, or a derivative, isomer, or pharmaceutically acceptable salt of any one of said necroptosis inhibitor compounds.

In a related aspect, in the methods disclosed herein the concentration of the 5-((7-Chloro-1H-indol-3-yl)methyl)-3-methyl-2,4-imidazolidinedione compound or said analog, derivative, isomer, or pharmaceutically acceptable salt thereof is about 0.2 nM-2 µM, and wherein the concentration of the 3,6-Dibromo-a-(1-piperazinylmethyl)-9H-carbazole-9-ethanol dihydrochloride compound, or analog, derivative, isomer, or pharmaceutically acceptable salt thereof is about 0.5 nM-50 µM.

In another related aspect, in the methods disclosed herein the composition further comprises, a nicotinamide adenine dinucleotide (NAD), an adenosine triphosphate (ATP), a cyclosporine A, a manganese-superoxide dismutase, or a zinc-superoxide dismutase, or any combination thereof. In another related aspect, in the methods disclosed herein, the concentration of said NAD is about 5 nM-500 µM, the concentration of said ATP is about 10 nM-1 mM, the concentration of said cyclosporin A is about 1 nM-1 mM, and the concentration of said manganese-superoxide dismutase or said zinc-superoxide is about 0.001 KU-100.0 KU.

In another related aspect, in the methods disclosed herein, the concentration of necroptosis inhibitor 5-((7-chloro-1H-indol-3-yl)methyl)-3-methyl-2,4-imidazolidinedione compound, or the analog, a derivative, a isomer, or a pharmaceutically acceptable salt thereof is about 20 nM, the concentration of Bax channel inhibitor 3,6-Dibromo-a-(1-piperazinylmethyl)-9H-carbazole-9-ethanol dihydrochloride compound, or the analog, the derivative, the isomer, or the pharmaceutically acceptable salt thereof is about 5 nM, the concentration of said NAD is about 0.05 nM, the concentration of said ATP is about 0.01 µM, the concentration of said cyclosporin A is about 0.01 µM, and the concentration of said manganese-superoxide dismutase or the zinc-superoxide is about 0.1 KU.

In a related aspect, in the methods disclosed herein, the composition further comprises a cryoprotective agent. In another related aspect, the cryoprotective agent comprises DMSO, or serum, or any combination thereof.

In a related aspect, in the methods disclosed herein, the composition further comprises a pharmaceutically acceptable carriers or excipients.

BRIEF DESCRIPTION OF THE DRAWINGS

The following drawings form part of the present specification and are included to further demonstrate certain embodiments of the present disclosure, the methods described herein may be better understood by reference to one or more of these drawings in combination with the detailed description of specific embodiments presented herein.

The patent or application file contains at least one drawing executed in color. Copies of this patent or patent application publication with color drawing(s) will be provided by the Office upon request and payment of the necessary fee.

FIG. 1A shows mouse cortical neuron tissue dissection and cell manipulation produced. ROS (detection of Nox1). Whereas no dissection yielded little ROS (mock), the freshly dissected tissue (fresh) yielded several-fold increase in ROS generation, while inclusion of the cryopreservation solution (Soln) diminished the ROS levels. FIG. 1B shows that apoptosis was enhanced after dissection (fresh) compared to unmanipulated tissue (mock), although to a lesser extent than ROS generation (FIG. 1A) or necrosis (FIG. 1C), while inclusion of the cryopreservation solution (+Soln) decreased this back to baseline levels. FIG. 1C shows that necrosis was enhanced after tissue dissection and cell manipulation (fresh) compared to no tissue manipulation (mock), an effect that was almost completely removed by inclusion of the cryopreservation solution (+Soln). (For FIGS. 1A-1C Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 nM nicotinamide adenine dinucleotide (NAD). 0.01 µM adenosine triphosphate (ATP), 0.01 µM cyclosporin A, and 0.1 Kuntz Unit manganese superoxide dismutase.)

FIG. 2A shows freeze/thaw of neurons produced ROS (detection of Nox1) (freeze) compared to tissue before freezing (mock), an effect which was almost completely abolished by inclusion of the cryopreservation solution (+Soln). FIG. 2B shows apoptosis was slightly enhanced after freeze/thaw (freeze) compared to tissue before freezing (mock), an effect that was decreased by inclusion of the cryopreservation solution during the freezing process (+Soln). FIG. 2C shows necrosis was greatly enhanced after cell freeze/thaw (freeze) compared to tissue before freezing (mock), an effect that was almost eliminated by inclusion of the cryopreservation solution (+Soln). (For FIGS. 2A-2C Soln: 20 nM 5-((7-Chloro-1H-indol-3-yl)methyl)-3-methyl-2,4-imidazolidinedione), 5 nM 3,6-Dihromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.) CypD-Cyclophilin D FIG. 3. Cellular freeze/thaw cycle causes stem cells to lose their identity, as measured by the level of CHAT1 in motor neurons. Cryoprotectants in solution used to freeze the cells, maintained motor neuron identity, as measure by the level of CHAT1.

FIG. 4A shows that the cryopreservation solutions disclosed herein, by itself was able to increase the percent viability of freshly dissected cells as well as cells that had been frozen in an embodiment of a cryopreservation solution, and then thawed. (Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.) Key FIG. 4A and throughout the figures: Fresh represents Freshly dissected cells; Fresh+Soln represents Freshly dissected cells in composition solution; Freeze represents Frozen/Thawed cells; and Freeze+Soln represents Frozen/Thawed cells in composition solution. FIG. 4B shows metabolic suspension of cells (hippocampal neuron) enhanced cell viability, wherein the percent viability provided by different components of cryopreservation solutions is shown. The cell viability for neurons was measure after 7 days in vitro. Vehicle is no cryopreservation solution addition, while necrostatin1 (Nec1), cyclosporine A (CspA), iMAC2 (iMAC2), or the combination of those 3 reagents (combine), were introduced to cells before the freeze/thayw process. In one embodiment (combine+Perfuse), the 3-reagent cryopreservation solution was perfused into a living pregnant mouse briefly just minutes before the pups were isolated from the dam, and then the hippocampal neurons isolated from the E18 (embryonic day 18) pups. The concentrations of the different components are those concentrations used in FIG. 4A.

FIG. 5 shows a comparison of the change in temperature over time during freezing in either an embodiment of a cryopreservation solution, disclosed herein (EVERGREEN™ Media Soln: 20 nM 5-((7-Chloro-1H-indol-3-yl)methyl)-3-methyl-2,4-imidazolidinedione), 5 nM 3,6-Dibrorno-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutaseq also known as EVERLAST™) versus a traditional media. Notice the absence of the early downward spike in temperature that occurs in traditional media.

FIG. 6A shows cortical neuron cell viability was maintained when freshly dissected cells were suspended in an embodiment of a cryopreservation solution (fresh+Soln) disclosed herein, or dissection in and then frozen in an embodiment of a cryopreservation solution disclosed herein (freeze+Soln). FIG. 6B shows the time course of percent neuron viability over time (days) after plating cells subjected to these freezing and non-freezing conditions. The inclusion of cryopreservation solution was compared to the same cells exposed to 10% DMSO before freezing (freeze) or to cells that were freshly dissected without any freezing cryoprotectant (fresh). FIG. 6C shows fat (adipose tissue-derived) stem cell viability was maintained when freshly dissected cells were suspended in an embodiment of a cryopreservation solution (fresh+Soln) disclosed herein, or dissection in and then frozen in an embodiment of a cryopreservation solution disclosed herein (freeze+Soln). FIG. 6D shows the time course of percent fat stem cell viability over time (days) after plating cells subjected to these freezing and non-freezing conditions. The inclusion of cryopreservation solution was compared to the same cells exposed to 10% DMSO before freezing (freeze) or to cells that were freshly dissected without any freezing cryoprotectant (fresh). (For FIGS. 6A-6D, Soln: 20 nM 5-((7-Chloro-1H-indol-3-yl) methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

FIG. 7A shows a comparison of the effects of cryoprotectant on early apoptotic cells (primary liver hepatocytes) from fresh and frozen cells suspended in an embodiment of a cryopreservation solution disclosed herein, compared with cell suspended in an absence of such a solution (mock). For cells frozen that were not treated with cryopreservation solution (mock), they were suspended in 10% DMSO before freezing. Caspase3 (green) labels cells in an early apoptotic state in culture. FIG. 7B shows the number of apoptotic cells, as defined by annexin V labeling, in fresh or frozen and thawed cells suspended in an embodiment of a cryopreservation solution disclosed herein or in the absence of such a solution (mock). (For FIGS. 7A-7B, Soln: 20 nM 5-((7-Chloro-1H-indol-3-yl) methyl)-3-methyl-2,4-midazolidinedione), 5 nM 3,6-Dibromo-a-(1-piperazinylmethyl)-9H-carbazole-9-ethanol dihydrochloride, 0.05 mN nicotinamide adenine dinucleotide (NAD), 0.01 µM adenosine triphosphate (ATP), 0.01 µM cyclosporin A, and 0.1 Kuntz Unit manganese superoxide dismutase.)

FIG. 8A shows a comparison of the presence of necrotic cells from solutions of fresh and frozen cells suspended in an embodiment of a cryopreservation solution disclosed herein, compared with cell suspended in an absence of such a solution. Anti-cyclophilin antibody labels cells in an early apoptotic state in culture. FIG. 8B shows the percent of necrotic cells after dissection performed in an embodiment of a cryopreservation solution, or the absence of such a solution. (For FIGS. 8A-8B, Soln: 20 nM 5-((7-Chloro-1H-indol-3-yl)methyl)-3-methyl-2,4-imidazolidinedione), 5 nM 3,6-Dibramo-a-(1-piperazinylmethyl)-9H-carbazole-9-ethanol dihydrochlorid, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

FIG. 9A shows Nox1 staining in fresh (dissected in saline only, and not frozen) neurons, fresh neurons dissected in cryopreservation solution (Fresh+Soln), neurons frozen while suspended in an embodiment of a cryopreservation solution disclosed herein, then thawed (Freeze+Soln) or in the presence of a conventional cryoprotectant (10% DMSO, dimethyl sulfoxide) (Freeze). Fresh or thawed neurons were plated and allowed to adhere before fixation and labeling for 4 hours. NADPH Oxidase (Nox1) labels ROS in cells. NeuN stains for cortical neurons (not glia). FIG. 9B shows ROS generation (Nox1 intensity) in freshly dissected cortical neuron tissue alone (fresh, blue bar), fresh cortical neuronal tissue dissected in the suspension of an embodiment of a cryopreservation solution disclosed herein (fresh+Soln, red bar), frozen cells suspended in an embodiment of a cryopreservation solution disclosed herein (freeze+soln, yellow bar) then thawed, or cells frozen and then thawed in the presence of 10% DMSO (green bar). (For FIGS. 9A-9B, Soln: 20 nM 5-((7-Chloro-1H-indol-3-yl)methyl-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

FIG. 10A shows the micrographs of neurons before or after freezing, in the presence or absence (10% DMSO only) of a cryopreservation solution disclosed herein. FIG. 10B shows motor neuron cell identity (as measure by the presence of CIAT1-positive, S100-positive immunofluorescence signal) in cells before and after freezing in conventional cryopreservation solutions (10% DMSO), and an embodiment of a cryopreservation solution disclosed herein ("after freeze composition"). (For FIGS. 10A-10B, Soln: 20 nM 5-((7-Chloro-1H-indol-3-yi)methyl)-3-methyl-2,4-imidazolidinedione), 5 nM 3,6-Dibramo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.

FIG. 11A shows a comparison of fresh and frozen liver cells (blue stain), incubated in the presence or absence (fresh, not frozen) of a cryopreservation solution disclosed herein, and either not (-galactosamine) or stimulated with galactosamine briefly before fixation and staining for antibody-conjugated uridine (red stain), as a general measure of galactosamine-induced transcription. FIG. 11B shows a comparison of liver cell transcriptional activity in fresh and frozen cells suspended in an embodiment of a cryopreservation solution disclosed herein, wherein the liver cell activity is similar after freeze/thaw when cells are maintained in the presence of a cryopreservation solution disclosed herein. Bars measure anti-body-conjugated uridine staining (arbitrary units). (For FIGS. 11A-11B, Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz, Unit manganese superoxide dismutase.)

FIG. 12 shows the effects of cryopreservation solutions comprising different necrostatins, wherein the presence of necrostatins (Nec1 (red bar), Nec2 (yellow bar). Nec3 (green bar) significantly enhanced percent viability of primary mouse cortical neuron cells compared to control cells (vehicle, blue bar) cryopreserved with conventional cryoprotectant (10% DMSO). The concentration of the different necrostatins is 20 nM, and the other components of the "soln" remain the same, that is: 5 nM 3,6-Dibromo-a-(1-piperazinylinethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.

FIG. 13A shows images of primary mouse liver cells (hepatocytes) before and after freezing in conventional cryopreservation solution (10% DMSO) and in an embodiment of a cryopreservation solution disclosed, herein ("composition freeze"). The cells here are staining with an antibody that recognizes HMBG1 (green) as a marker for necroptosis. FIG. 13B shows that necroptotic markers were significantly inhibited in a cell suspension in an embodiment of a cryopreservation solution disclosed herein, compared with 10% DMSO ("DMSO freeze"). (cryopreservation solution used herein was: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

Media Solution (7-9). (**) Significant difference (p<0.001) between LPS alone (4-6) and LPS+100% EVERGREEN™ Media Solution (10-12).

Figure 16:
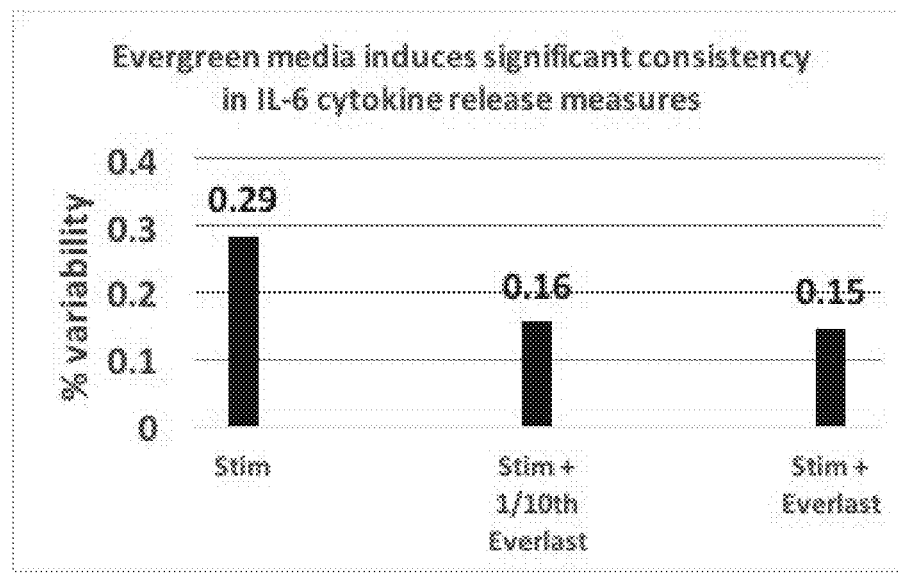

FIG. 16. A cryopreservation solution (EVERGREEN™ Media Soln: 20 nM 5-((7-Chloro-1H-indol-3-yl)methyl)-3-methyl-2,4-imidazoidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosportin A, and 0.1 Kuntz Unit manganese superoxide dismutase; also known as EVERLAST™) produced significant consistency in cytokine release measures. Percent variability was calculated by averaging the percent errors of each (triplicate) experiment (n=3), and expressing each group's (stimulated, 10% EVERGREEN™, 100% EVERGREEN™) percent variability as a ratio to the mock (control) stimulated group variability. From this, there is ~100% increase in variability without the use of EVERGREEN™ Media Solution (both at 10% and 100% levels).

Figure 17:
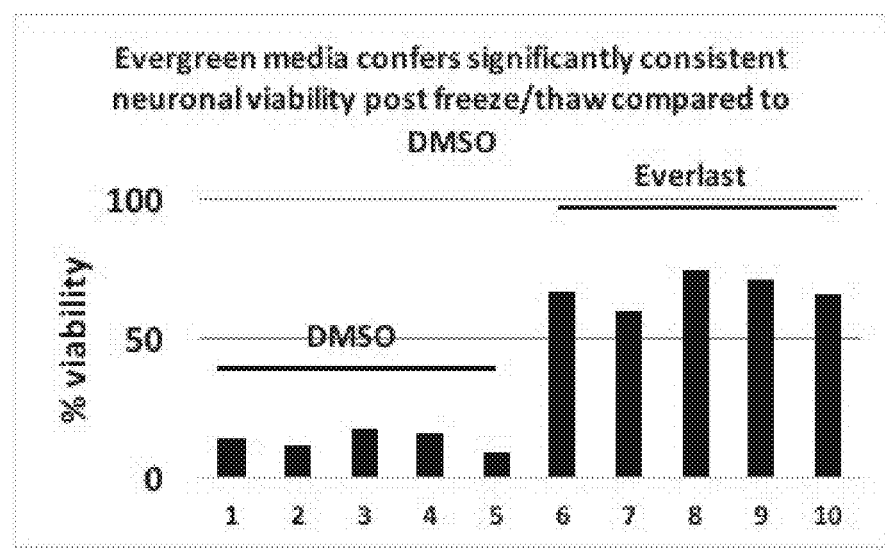

FIG. 17. A cryopreservation solution (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; also known as EVERLAST™) conferred significantly consistent neuronal viability post freeze/thaw compared to DMSO. EVERGREEN™ Media Solution was used to freeze primary mouse hippocampal neurons compared to dimethyl sulfoxide (DMSO) and viability post-thaw was measured and plotted. Five independent experiments were measured.

Figure 18:
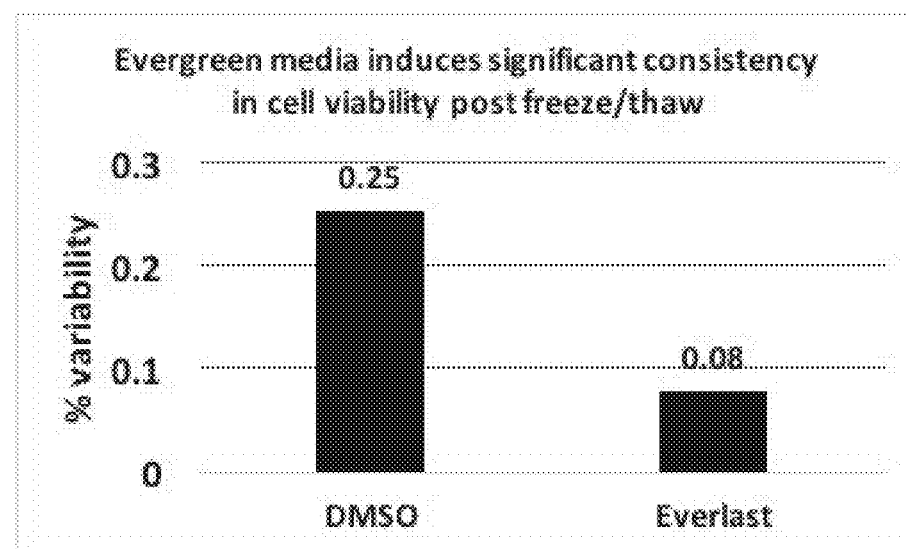

FIG. 18. A cryopreservation solution (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-1-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; also known as EVERLAST™) induced significant consistency in neuronal cell viability post freeze/thaw. Percent variability was calculated by averaging the means of each experiment (n=5) and expressing each group's individual measurement as a ratio of the individual value to the mean value. From this, the percent deviation was calculated and expressed as a ratio to the mean. From this, there is an ~300% increase in variability without the use of EVERGREEN™ Media Solution.

Figure 19A:
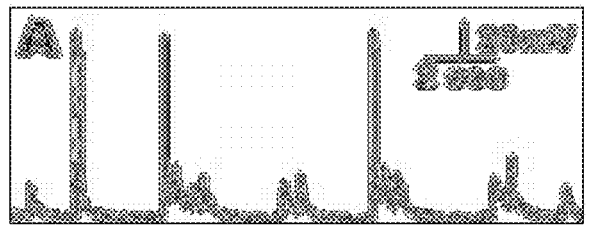
Figure 19B:
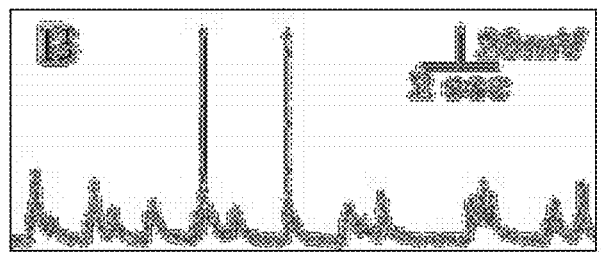
Figure 19C:
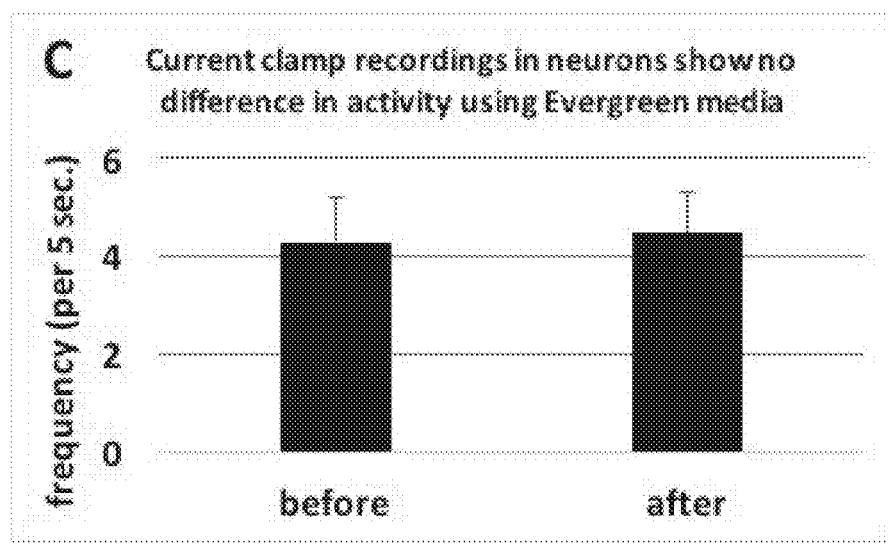
Figure 19D:
Figure 19E:
Figure 19F:
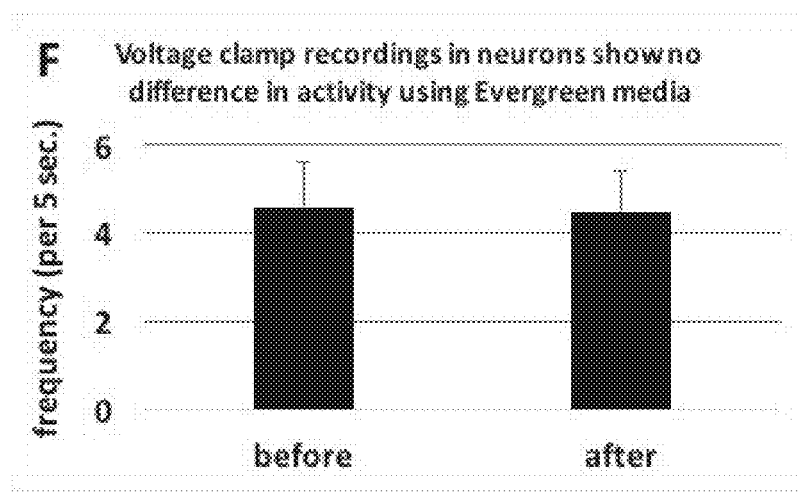
Figure 19G:
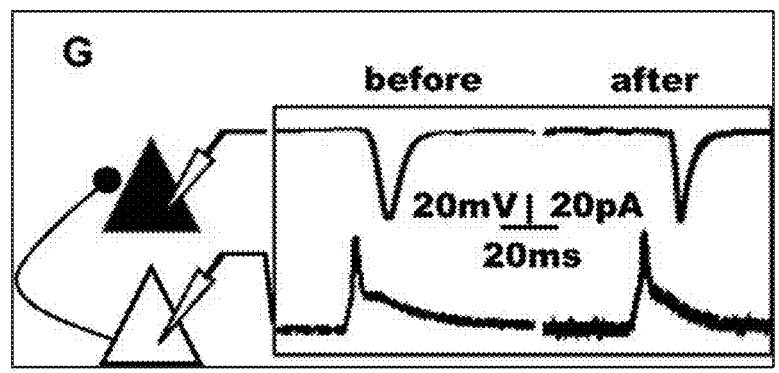
Figure 19H:
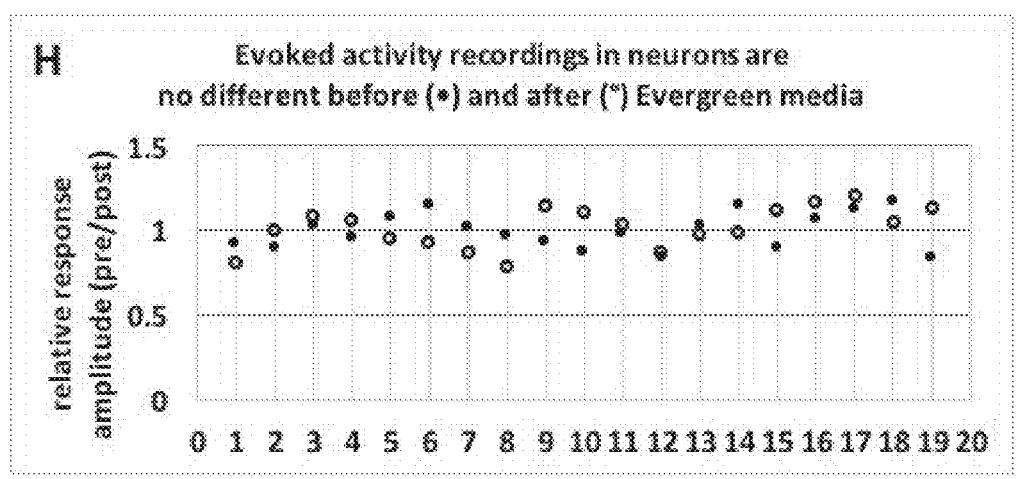

FIGS. 19A-19H. Hippocampal neurons show physiological characteristics that are indistinguishable from before (freshly dissected) and after freeze/thaw using a cryopreservation solution (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinytmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; also known as EVERLAST™). Patch clamp of embryonic day 17-19 neurons shows current and voltage profiles from both spontaneous and evoked neuronal activities. FIG. 19A shows hippocampal neurons from freshly dissected mouse brain showing whole cell current clamp (at resting membrane potential) recording demonstrates network activity in culture. Vertical bar represents 20 milliVolts (mV) magnitude and horizontal bar 2 seconds (sec) of recording. FIG. 19B shows hippocampal neuron from freshly dissected mouse brain after freeze/thaw using EVERGREEN™ Media Solution showing whole cell current clamp (at resting membrane potential) recording demonstrates network activity in culture. Vertical bar represents 20 milliVolts (mV) magnitude and horizontal bar 2 seconds (sec) of recording. FIG. 19C shows Cumulative frequency over 5 minutes recording interval for current clamp data showing average frequency of action potential discharges. Values are mean+SE (standard error) of at least 4 independent experiments, which show no statistically significant differences (p>0.7, Student's t-test) either before or after freeze/thaw using EVERGREEN™ Media Solution. FIG. 19D shows hippocampal neuron from freshly dissected mouse brain showing whole cell voltage clamp (at −60 mV) recording demonstrates network activity in culture. Vertical bar represents 200 picoAmps (pA) magnitude and horizontal bar 2 seconds (sec) of recording. FIG. 19E shows hippocampal neuron from freshly dissected mouse brain after freeze/thaw using EVERGREEN™ Media Solution showing whole cell voltage clamp (at −60 mV) recording demonstrates network activity in culture. Vertical bar represents 200 picoAmps (pA) magnitude and horizontal bar 2 seconds (sec) of recording. FIG. 19F shows cumulative frequency over 5 minutes recording interval for voltage clamp data showing average frequency of action potential discharges. Values are mean+SE (standard error) of at least 4 independent experiments, which show no statistically significant difference (p>0.8) either before or after freeze/thaw using EVERGREEN™ Media Solution. FIG. 19G shows evoked presynaptic action potential shown (lower traces) in current clamp mode at resting potential and the post-synaptic excitatory synaptic response (upper traces) (shown on schematic at left as black circle at end of axon from lower presynaptic neuron) from two adjacent coupled hippocampal neurons, both before (left traces, freshly dissected) and after (right traces) freeze/thaw using EVERGREEN™ Media Solution. Here, the excitatory post synaptic currents (EPSCs) are not statistically different between treatments (actual values 71+/−23 pA before versus 76+/−28 pA after). Representative traces from n=19-22 neurons, at least 3 independent experiments for each treatment (p>0.7, Student's t-test). Vertical bar represents 20 picoAmps (pA) magnitude for current clamped neurons (pre-synaptic, lower traces) and 20 milli-Volts (mV) for the excitatory synaptic responses (post-synaptic, upper traces); horizontal bar represents 20 milli-Seconds (ms) of recording. FIG. 19H shows evoked action potential amplitude ratios for presynaptic over post-synaptic (pre/post) responses for 19 hippocampal neurons (as measured in part G) both before (closed circles) and after (open circles) freeze/thaw using EVERGREEN™ Media Solution. Average ratios are not statistically different for neurons before and after freeze/thaw using EVERGREEN™ Media Solution (p>0.7, Student's t-test) (average values 71+/−23 pA for before versus 76+/−28 pA for after freeze/thaw). X values correspond to neuron numbers for each treatment.

DETAILED DESCRIPTION

In the following detailed description, numerous specific details are set forth in order to provide a thorough understanding of the compositions and methods presented herein. In other instances, well-known methods, procedures, and components have not been described in detail so as not to obscure the compositions and methods and resultant inhibition of necrosis and necroptosis, suppression of ischemia and oxidative damage, improvement in cell viability, enhancement of cells' growth potential, and stabilization of cell identity, as disclosed herein.

In one embodiment, disclosed herein is a composition for cryopreservation of mammalian cells, tissues, organs and portions thereof, comprising a necroptosis inhibitor and a Bax channel inhibitor. In another embodiment, disclosed herein is a method for cryopreservation of mammalian cells, tissues, and organs, comprising the steps of (a) bringing said cells, tissues, or organs or portions thereof in contact with a composition comprising a necroptosis inhibitor and a Bax channel inhibitor, and (b) cooling the composition comprising said cells, tissues, or organs or portions thereof. In a further embodiment, disclosed herein is method for suppressing, preventing or avoiding cell necrosis that results from physical and physiological damage cells incur in the course of cell manipulations in vitro, during liberation from tissue, and during cryopreservation and freeze-thaw cycles thereof.

Compositions

In one embodiment, disclosed herein is a composition comprising a necroptosis inhibitor and a Bax channel inhibitor. A skilled artisan would appreciate that necroptosis may encompass any form of active necrosis (death of living cells or tissues). In some embodiments, necrosis comprises cell membrane and organelle disruption, cell swelling and mitochondrial impairment, followed by cell lysis and accompanied by inflammatory response. In some embodiments, necroptosis comprises response to inflammatory signals and stress in particular from tissues. In some embodiments, necroptosis comprises regulated necrosis.

In one embodiment, necroptosis comprises an active or programed form of necrosis (cell death). In another embodiment, necroptosis comprises a necrotic cell death dependent on receptor-interacting protein kinase-1 (RIPK1). In another embodiment, necroptosis comprises a necrotic cell death dependent on receptor-interacting protein kinase-3 (RIPK3). In another embodiment, necroptosis comprises a regulated caspase-independent cell death mechanism that results in morphological features resembling necrosis. In some embodiments activation of TNF-receptor leads to RIPK1 activation and subsequent recruitment of RIPK3 forming the necrosome. In another embodiment, necroptosis comprises a non-apoptotic cell death pathway.

In one embodiment, a necroptosis inhibitor comprises a compound that inhibits any form of active necrosis. In another embodiment, a necroptosis inhibitor comprises a compound that inhibits any form of necrosis. In another embodiment, a necroptosis inhibitor comprises a compound that inhibits any form of necroptosis. In another embodiment, a necroptosis inhibitor comprises an inhibitor of necrotic cell death dependent on receptor-interacting protein kinase-1 (RIPK1). In another embodiment, a necroptosis inhibitor comprises an inhibitor of necrotic cell death dependent on receptor-interacting protein kinase-3 (RIPK3). In another embodiment, a necroptosis inhibitor comprises an inhibitor of regulated caspase-independent cell death mechanism that results in morphological features resembling necrosis.

While not wishing to be bound by theory, the activity of receptor interacting protein kinases (RIPK) has been shown to be important for cells to undergo necroptosis. Furthermore, RIP kinases' activity is also known to promote the release of inflammatory mediators such as TNF alpha from cells which can induce inflammation and also promote further necroptosis. In one embodiment, a necroptosis inhibitor comprises a RIPK inhibitor. In another embodiment, a necroptosis inhibitor comprises a RIP1 inhibitor. In another embodiment, a necroptosis inhibitor comprises a RIP3 inhibitor.

In one embodiment, the necroptosis inhibitor comprises a 5-((7-Chloro-1H-indol-3-yl)methyl)-3-methyl-2,4-imidazolidinedione (necrostatin-1s) compound, or an analog, a derivative, an isomer, or a pharmaceutically acceptable salt thereof. In another embodiment, the structure of necrostatin-1s is represented in Formula 1:

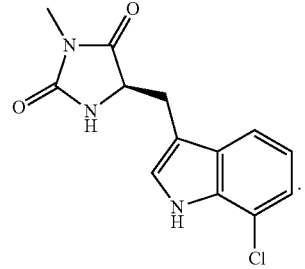

Formula I

As used herein, the terms "5-((7-Chloro-1H-indol-3-yl)methyl)-3-methyl-2,4-imidazolidinedione", "5-((7-Chloro-1H-indol-3-yl)methyl)-3-methylimidazolidine-2,4-dione", "7-Cl—O-MH-Trp", "necrostatin-1 s", "Nec-1 s", "Nec-1 stable", "RIPK1 Inhibitor II", "Receptor-Interacting Protein 1 Inhibitor II", "Necrosis Inhibitor IV", and "7N-1" may be used interchangeably having all the same meanings and qualities.

One of ordinary skill in the art would appreciate that term "analog" may encompass any compound having a structure similar to that of another one, but differing from it in respect of a certain component such as a functional group or a substructure. The term "analog" is used interchangeably with "analog compound".

One of ordinary skill in the art would appreciate that term "necrostatin-1s analog" may encompass a compound having a structure similar to that of necrostatin-1s, but differing from it in respect of a certain component such as replacement of one atom or a group of atoms or a functional group or a substructure with another atom or group of atoms or functional group or a substructure. In another embodiment, the necroptosis inhibitor is any necrostatin-1 s analog known in the art.

In another embodiment, the necroptosis inhibitor comprises a 5-((7-Chloro-1H-indol-3-yl)methyl)-3-methyl-2,4-imidazolidinedione (necrostatin-1s) compound or an analog, a derivative, an isomer, or a pharmaceutically acceptable salt thereof. In another embodiment, a necroptosis inhibitor compound comprises a 3-p-Methoxyphenyl-5,6-tetramethylenothieno[2,3-d]pyrimidin-4-one-2-mercaptoethylcyanide (Nec-5) compound or an analog, a derivative, an isomer, or a pharmaceutically acceptable salt thereof. In another embodiment, a necroptosis inhibitor compound comprises a (Z)-5-((3-(4-Fluorophenyl)-1H-pyrazol-4-yl)methylene-2-imino-3-(thiazol-2-yl)thiazolidin-4-one compound (Nec-7) or an analog, a derivative, an isomer, or a pharmaceutically acceptable salt thereof. In another embodiment, a necroptosis inhibitor compound comprises a 5-(Indol-3-ylmethyl)-(2-thio-3-methyl)hydantoin compound (necrostatin-1; Nec-1), or an analog, a derivative, an isomer, or a pharmaceutically acceptable salt thereof. In one embodiment, Nec-1 is represented by a structure of Formula II Formula II

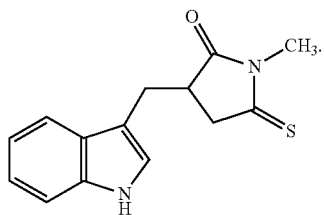

In another embodiment, a necroptosis inhibitor compound comprises a methyl-thiohydantoin-tryptophan compound, or an analog, a derivative, an isomer, or a pharmaceutically acceptable salt thereof. In another embodiment, a necroptosis inhibitor compound comprises a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound (Nec-3a), or an analog, a derivative, an isomer, or a pharmaceutically acceptable salt thereof. In another embodiment, a necroptosis inhibitor compound comprises a (S)—N-(1-[2-chloro-6-fluorophenyl]ethyl)-5-cyano-1-methyl-1H-pyrrole-2-carboxamide compound (Nec-4), or an analog, a derivative, an isomer, or a pharmaceutically acceptable salt thereof. In another embodiment, a necroptosis inhibitor compound comprises a (E)-N-(4-(N-(3-Methoxypyrazin-2-yl)sulfamoyl)phenyl)-3-(5-nitrothiophene-2-yl)acrylamide compound (necrosulfonamide), or an analog, a derivative, an isomer, or a pharmaceutically acceptable salt thereof. In another embodiment, a necroptosis inhibitor compound comprises a 1-(4-(4-Aminofuro[2,3-d]pyrimidin-5-yl)phenyl)-3-(2-fluoro-5-(trifluoromethyl)phenyl)urea compound (RIP1 Inhibitor III), or an analog, a derivative, an isomer, or a pharmaceutically acceptable salt thereof.

In another embodiment, a necroptosis inhibitor compound comprises a 3-p-Methoxyphenyl-5,6-tetramethylenothieno[2,3-d]pyrimidin-4-one-2-mercaptoethylcyanide (Nec-5) compound, a (Z)-5-((3-(4-Fluorophenyl)-1H-pyrazol-4-yl)methylene)-2-imino-3-(thiazol-2-yl)thiazolidin-4-one compound (Nec-7), a 5-(Indol-3-ylmethyl)-(2-thio-3-methyl)hydantoin compound (Nec-1), a methyl-thiohydantoin-tryptophan compound, a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound (Nec-3a), a (S)—N-(1-[2-chloro-6-fluorophenyl]ethyl)-5-cyano-1-methyl-1H-pyrrole-2-carboxamide compound (Nec-4), a (E)-N-(4-(N-(3-Methoxypyrazin-2-yl)sulfamoyl)phenyl)-3-(5-nitrothiophene-2-yl)acrylamide compound (necrosulfonamide), a 1-(4-(4-Aminofuro[2,3-d]pyrimidin-5-yl)phenyl)-3-(2-fluoro-5-(trifluoromethyl)phenyl)urea compound (RIP1 inhibitor III), 2,2-dimethyl-1-(5(S)-phenyl-4,5-dihydro-pyrazol-1-yl)-propan-1-one (GSK'963), or an analog, a derivative, an isomer, or a pharmaceutically acceptable salt of any one of said necroptosis inhibitor compounds.

In another embodiment, the necroptosis inhibitor comprises a 5-(1H-Indol-3-ylmethyl)-3-methyl-2-thioxo-4-Imidazolidinone (necrostatin-1) compound, or an analog, a derivative, an isomer, or a pharmaceutically acceptable salt thereof. As used herein, the term "5-(1H-Indol-3-ylmethyl)-3-methyl-2-thioxo-4-Imidazolidinone", may be used interchangeably with necrostatin-1, "5-(Indol-3-ylmethyl)-3-methyl-2-thio-Hydantoin", "Methylthiohydantoin-DL-tryptophan", or "MTH-DL-Tryptophan", "MTH-Trp", "RIP1 Inhibitor I", "Necrosome Inhibitor I", "Receptor-Interacting Protein 1 Inhibitor I", "Necrosis Inhibitor I" or "Nec-1", having all the same qualities and meanings.

One of ordinary skill in the art would appreciate that term "necrostatin-1 analog" may encompass a compound having a structure similar to that of necrostatin-1, but differing from it in respect of a certain component such as replacement of one atom or a group of atoms or a functional group or a substructure with another atom or group of atoms or functional group or a substructure. Multiple necrostatin-1 analogs have been described in the art and are contemplated herein (see e.g. U.S. Pat. No. 8,324,262, columns 1-31 and 51-52; U.S. Pat. No. 8,658,689 columns 2-31; U.S. Pat. No. 9,108,955 columns 2-31; and U.S. Pat. No. 9,499,521 columns 2-5, 12-20 and 49-57; U.S. Patent Application Publications Ser. No: 2005/0119260, paragraphs [0008]-[0103]; 2013/0158024, paragraphs [0009]-[0166]; 2010/0190836, paragraphs [0009]-[01.68]; 2012/0122889, paragraphs [0008]-[0266]; and 2014/0024657, paragraphs [0008]-[0423] and [447]; PCT Patent Application Publications Ser. No. WO 2014152182, pages 2-4, 6-9, 11-14; and WO 2016094846, pages 2-4, 13-19 and 39-50; and EPO Patent Application Publication Ser. No. EP 3017825 paragraphs [0009], [0021], and [0025], all of which are hereby incorporated by reference in their entirety).

In another embodiment, the necroptosis inhibitor is any necrostatin-1 analog or necrostatin-1s inhibitor known in the art.

In another embodiment, a necroptosis inhibitor comprises a 5-((7-Chloro-1H-indol-3-yl)methyl)-3-methyl-2,4-imidazolidinedione (Nec-1s), a 3-p-Methoxyphenyl-5,6-tetramethylenothieno[2,3-d]pyrimidin-4-one-2-mercaptoethylcyanide (Nec-5) compound, a (Z)-5-((3-(4-Fluorophenyl)-1H-pyrazol-4-yl)methylene)-2-imino-3-(thiazol-2-yl) thiazolidin-4-one compound (Nec-7), a 5-(Indol-3-ylmethyl)-(2-thio-3-methyl)hydantoin compound (Nec-1), a methyl-thiohydantoin-tryptophan compound, a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound (Nec-3a), a (S)—N-(1-[2-chloro-6-fluorophenyl]ethyl)-5-cyano-1-methyl-1H-pyrrole-2-carboxamide compound (Nec-4), a (E)-N-(4-(N-(3-Methoxypyrazin-2-yl)sulfamoyl)phenyl)-3-(5-nitrothiophene-2-yl)acrylamide compound (necrosulfonamide), a 1-(4-(4-Aminofuro[2,3-d]pyrimidin-5-yl)phenyl)-3-(2-fluoro-5-(trifluoromethyl)phenyl)urea compound (RIP1 Inhibitor III), or 2,2-dimethyl-1-(5(S)-phenyl-4,5-dihydro-pyrazol-1-yl)-propan-1-one compound (GS K'963), or an analog, a derivative, an isomer, or a pharmaceutically acceptable salt of any one of said necroptosis inhibitors.

While not wishing to be bound by theory, it is believed that mitochondria are the central orchestrators of both apoptosis and regulated necrosis. In some embodiments, during regulated necrosis the mitochondria become dysfunctional in a process that is, termed "maladaptive" where mitochondria swell, lose their ability to generate ATP, and subsequently rupture. In some embodiments, the maladaptive process is driven in part by the opening of the mitochondrial permeability transition pores (MPTP), a process that is in turn activates Bax and Bak protein-mediated signaling. In some embodiments, Bax (Bcl-2-associated X protein) is a protein that primarily found in cytosol. In some embodiments, upon initiation of necrosis, Bax undergoes a conformational shift and becomes associated with mitochondrial membrane, where it forms a multimeric pore within the mitochondrial membrane.

Multiple Bax channel inhibitors have been described in the art and are contemplated herein (see e.g. PCT Patent Application Publications Ser. No. WO 2014110476, pages 18-40; and EPO Patent Application Publication Ser. No. EP 1094063, pages 5-14, all of which are hereby incorporated by reference in their entirety). In another embodiment, the Bax channel inhibitor is any Bax channel inhibitor known in the art. In another embodiment, the Bax channel inhibitor comprises an analog, a derivative, an isomer, or a pharmaceutically acceptable salt of a Bax channel inhibitor.

In one embodiment, the Bax channel inhibitor comprises a 3,6-Dibromo-a-(1-piperazinylmethyl)-9H-carbazole-9-ethanol dihydrochloride compound, or an analog, a derivative, an isomer, or a pharmaceutically acceptable salt thereof.

In one embodiment, a composition disclosed herein comprises a necroptosis inhibitor comprising a 5-((7-Chloro-1H-indol-3-yl)methyl)-3-methyl-2,4-imidazolidinedione compound or an analog, derivative, isomer, or pharmaceutically acceptable salt thereof, and a Bax channel inhibitor comprising a 3,6-Dibromo-a-(1-piperazinylmethyl)-9H-carbazole-9-ethanol dihydrochloride compound, or an analog, derivative, isomer, or pharmaceutically acceptable salt thereof.

In one embodiment, the composition comprises a necroptosis inhibitor selected from the group comprising a 5-((7-Chloro-1H-indol-3-yl)methyl)-3-methyl-2,4-imidazolidinedione, a 3-p-Methoxyphenyl-5,6-tetramethylenothieno[2,3-d]pyrimidin-4-one-2-mercaptoethylcyanide compound, a (Z)-5-((3-(4-Fluorophenyl)-1H-pyrazol-4-yl)methylene)-2-imino-3-(thiazol-2-yl)thiazolidin-4-one compound, a 5-(Indol-3-ylmethyl)-(2-thio-3-methyl)hydantoin compound, 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound, (S)—N-(1-[2-chloro-6-fluorophenyl]ethyl)-5-cyano-1-methyl-1H-pyrrole-2-carboxamide compound, methyl-thiohydantoin-tryptophan compound, (E)-N-(4-(N-(3-Methoxypyrazin-2-yl)sulfamoyl)phenyl)-3-(5-nitrothiophene-2-yl)acrylamide compound, or 1-(4-(4-Aminofuro[2,3-d]pyrimidin-5-yl)phenyl)-3-(2-fluoro-5-(trifluoromethyl)phenyl)urea compound, or 2,2-dimethyl-1-(5 (S)-phenyl-4,5-dihydro-pyrazol-1-yl)-propan-1-one compound, or an analog, derivative, isomer, or pharmaceutically acceptable salt of said necroptosis inhibitor compound, and a Bax channel inhibitor or an analog, derivative, isomer, or pharmaceutically acceptable salt thereof.

In another embodiment, the composition comprises a necroptosis inhibitor selected from the group comprising a 5-((7-Chloro-1H-indol-3-yl)methyl)-3-methyl-2,4-imidazolidinedione, a 3-p-Methoxyphenyl-5,6-tetramethylenothieno[2,3-d]pyrimidin-4-one-2-mercaptoethylcyanide compound, a (Z)-5-((3-(4-Fluorophenyl)-1H-pyrazol-4-yl)methylene)-2-imino-3-(thiazol-2-yl)thiazolidin-4-one compound, a 5-(Indol-3-ylmethyl)-(2-thio-3-methyl)hydantoin compound, 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone compound, (S)—N-(1-[2-chloro-6-fluorophenyl]ethyl)-5-cyano-1-methyl-1H-pyrrole-2-carboxamide compound, methyl-thiohydantoin-tryptophan compound, (E)-N-(4-(N-(3-Methoxypyrazin-2-yl)sulfamoyl)phenyl)-3-(5-nitrothiophene-2-yl) acrylamide compound, 1-(4-(4-Aminofuro[2,3-d]pyrimidin-5-yl)phenyl)-3-(2-fluoro-5-(trifluoromethyl)phenyl)urea compound, or 2,2-dimethyl-1-(5(S)-phenyl-4,5-dihydro-pyrazol-1-yl)-propan-1-one compound, or an analog, derivative, isomer, or pharmaceutically acceptable salt of said necroptosis inhibitor compound, and a Bax channel inhibitor comprising a 3,6-Dibromo-a-(1-piperazinylmethyl)-9H-carbazole-9-ethanol dihydrochloride compound, or an analog, derivative, isomer, or pharmaceutically acceptable salt thereof.

One of ordinary skill in the art would appreciate that term "isomer" may encompass an optical isomers and analogs, structural isomers and analogs, conformational isomers and analogs, and the like. Optical isomers, are also known as enantiomers and may in one embodiment comprise one of two stereoisomers that are mirror images of each other that are non-superposable (not identical).

In one embodiment, an isomer comprises optical isomers of the necroptosis inhibitor compound. It will be appreciated by those skilled in the art that the necroptosis inhibitor compound disclosed herein may contain at least one chiral center. Accordingly, the necroptosis inhibitor compound used in the compositions and methods disclosed herein may exist in optically-active or racemic forms. Some compounds may also exhibit polymorphism. It is to be understood that in one embodiment, the necroptosis inhibitor compounds may encompass any racemic, optically-active, polymorphic, or stereo-isomeric form, or mixtures thereof, which form possesses properties useful in methods of cryopreservation herein. In another embodiment, any racemic, optically-active, polymorphic, or stereo-isomeric form, or mixtures thereof, of a necroptosis inhibitor compound described herein, may possess properties useful in method of treating, preventing, inhibiting, or reducing the incidence of cellular plasticity disclosed herein.

One of ordinary skill in the art would appreciate that term "enantiomer", may encompass compound having a center of chirality and being one of two stereoisomers that are non-superposable complete mirror images of each other. As known in the art, enantiomers differ from each other in their ability to rotate plane-polarized light and may be classified according to the CIP (Cahn-Ingold-Prelog)-convention as S- or R-enantiomer. The S- and R-configurations represent the three-dimensional orientation of the four substituents about the chiral center carbon atom.

In one embodiment, a necroptosis inhibitor compound is the pure (R)-isomer. In another embodiment, a necroptosis inhibitor compound is the pure (S)-isomer. In another embodiment, a necroptosis inhibitor compound comprises a mixture of the (R) and the (S) isomers. In another embodiment, a necroptosis inhibitor compound is a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In one embodiment, a Bax channel inhibitor compound is the pure (R)-isomer. In another embodiment, a Bax channel inhibitor compound is the pure (S)-isomer. In another embodiment, a Bax channel inhibitor compound comprises a mixture of the (R) and the (S) isomers. In another embodiment, a Bax channel inhibitor compound is a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

One of ordinary skill in the art would appreciate that term "tautomer" may encompass compounds produced by the phenomenon wherein a proton of one atom of a molecule shifts to another atom, thereby forming a structural isomer of the original compound. See, Jerry March, Advanced Organic Chemistry: Reactions, Mechanisms and Structures, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal, aromatic tautomers and the like. The compounds described herein may have one or more tautomers and therefore include various isomers. All such isomeric forms of these compounds are expressly included in the compositions disclosed herein.

One of ordinary skill in the art would appreciate that term "derivative", may encompass any pharmaceutically acceptable derivative or non-pharmaceutically acceptable derivative which is suitable for use in the process disclosed herein. The skilled person will appreciate that non-pharmaceutically acceptable derivatives may be used to prepare compounds and derivatives suitable for pharmaceutical use. In one embodiment, the derivatives used or prepared in the compositions disclosed herein are pharmaceutically acceptable derivatives.

One of ordinary skill in the art would appreciate that term "pharmaceutically acceptable salt" may encompass salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For a review on suitable salts see Berge et al., J. Pharm. Sci., 1977, 66, 1-19.

Typically, a pharmaceutically acceptable salt may be readily prepared by using a desired acid or base as appropriate. The salt may precipitate from solution and be collected by filtration or may be recovered by evaporation of the solvent. The salt can also be prepared in situ during the final isolation and purification of the compounds of a composition disclosed herein or separately by reacting the free base group with a suitable organic acid.

Salts my comprise acid addition salts resulting from reaction of an acid with basic nitrogen atom. Salts encompassed within the term "pharmaceutically acceptable salts" refer to non-toxic salts of the compounds disclosed herein. Suitable addition salts are formed from acids which form non-toxic salts and examples are acetate, p-aminobenzoate, ascorbate, aspartate, benzenesulfonate, benzoate, bicarbonate, bismethylenesalicylate, bisulfate, bitartrate, borate, bromide, calcium edetate, camsylate, carbonate, chloride, clavulanate, citrate, cyclohexylsulfamate, dihydrochloride, edetate, edisylate, estolate, esylate, ethanedisulfonate, ethanesulfonate, formate, fumarate, gluceptate, gluconate, glutamate, glutarate, glycollate, glycollylarsanilate, hemisulfate, hexylresorcinate, hydrabamine, hydrobromide, hydrochloride, hydrogen phosphate, hydroiodide, hydroxynaphthoate, iodide, isethionate, itaconate, lactate, lactobionate, laurate, malate, maleate, mandelate, mesylate, methylbromide, methyinitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, piruvate, polygalacturonate, propionate, saccharate, salicylate, stearate, subacetate, succinate, sulfate, tannate, tartrate, teoclate, tosylate, triethiodide, trifluoroacetate and valerate. In some embodiments, salts prepared in the compositions disclosed herein include the succinate, glutarate and hemisulfate salts.

In one embodiment, the concentration of a necroptosis inhibitor comprised in a composition disclosed herein, comprises a range of about 0.2 nM to 2 µM. In another embodiment, the concentration of the necroptosis inhibitor comprises a range of about 0.2 nM to about 0.5 nM. In another embodiment, the concentration of the necroptosis inhibitor comprises a range of about 0.5 nM to about 5 nM. In another embodiment, the concentration of a necroptosis inhibitor comprises a range of about 5 nM to about 50 nM. In another embodiment, the concentration of a necroptosis inhibitor comprises a range of about 50 nM to about 500 nM. In another embodiment, the concentration of a necroptosis inhibitor comprises a range of about 50 nM to about 100 nM, In another embodiment, the concentration of a necroptosis inhibitor comprises a range of about 100 nM to about 200 nM. In another embodiment, the concentration of a necroptosis inhibitor comprises a range of about 200 nM to about 300 nM. In another embodiment, the concentration of a necroptosis inhibitor comprises a range of about 300 nM to about 400 nM. In another embodiment, the concentration of a necroptosis inhibitor comprises a range of about 400 nM to about 500 nM. In another embodiment, the concentration of a necroptosis inhibitor comprises a range of about 500 nM to about 1 µM. In another embodiment, the concentration of a necroptosis inhibitor comprises a range of about 500 nM to about 600 nM. In another embodiment, the concentration of a necroptosis inhibitor comprises a range of about 600 nM to about 700 nM. In another embodiment, the concentration of a necroptosis inhibitor comprises a range of about 700 nM to about 800 nM. In another embodiment, the concentration of a necroptosis inhibitor comprises a range of about 800 nM to about 900 nM, In another embodiment, the concentration of a necroptosis inhibitor comprises a range of about 900 nM to about 1 µM. In another embodiment, the concentration of a necroptosis inhibitor comprises a range of about 1 µM to about 2 µM. In another embodiment, the concentration of a necroptosis inhibitor comprises a range of about 1 µM to about 1.1 µM. In another embodiment, the concentration of a necroptosis inhibitor comprises a range of about 1 µM to about 1.2 µM. In another embodiment, the concentration of a necroptosis inhibitor comprises a range of about 1.2 µM to about 1.3 µM. In another embodiment, the concentration of a necroptosis inhibitor comprises a range of about 1.3 µM to about 1.4 µM, In another embodiment, the concentration of a necroptosis inhibitor comprises a range of about 1.4 µM to about 1.5 µM. In another embodiment, the concentration of a necroptosis inhibitor comprises a range of about 1.5 µM to about 1.6 µM. In another embodiment, the concentration of a necroptosis inhibitor comprises a range of about 1.6 µM to about 1.7 µM. In another embodiment, the concentration of a necroptosis inhibitor comprises a range of about 1.7 µM to about 1.8 µM. In another embodiment, the concentration of a necroptosis inhibitor comprises a range of about 1.8 µM to about 1.9 µM. In another embodiment, the concentration of a necroptosis inhibitor comprises a range of about 1.9 µM to about 2.0 µM. In another embodiment, the concentration of a necroptosis inhibitor comprises a range of about 2 µM to about 200 µM. In another embodiment, the concentration of a necroptosis inhibitor comprises a range of about 200 µM to about 500 µM.

In one embodiment, the final concentration of the necroptosis inhibitor comprised in a composition disclosed herein is about 0.2 nM. In another embodiment, the final concentration of the necroptosis inhibitor is about 2.0 nM. In another embodiment, the final concentration of the necroptosis inhibitor is about 20 nM. In another embodiment, the final concentration of the necroptosis inhibitor is about 200 nM. In another embodiment, the final concentration of the necroptosis inhibitor is about 2 µM.

In one embodiment, the concentration of a necrostatin-1s compound comprised in a composition disclosed herein, comprises a range of about 0.2 nM to 2 µM. In another embodiment, the concentration of the necrostatin-1s compound comprises a range of about 0.2 nM to about 0.5 nM. In another embodiment, the concentration of the necrostatin-1s compound comprises a range of about 0.5 nM to about 5 nM. In another embodiment, the concentration of a necrostatin-1s compound comprises a range of about 5 nM to about 50 nM. In another embodiment, the concentration of a necrostatin-1s compound comprises a range of about 50 nM to about 500 nM. In another embodiment, the concentration of a necrostatin-1s compound comprises a range of about 50 nM to about 100 nM. In another embodiment, the concentration of a necrostatin-1s compound comprises a range of about 100 nM to about 200 nM. In another embodiment, the concentration of a necrostatin-1s compound comprises a range of about 200 nM to about 300 nM, In another embodiment, the concentration of a necrostatin-1s compound comprises a range of about 300 nM to about 400 nM. In another embodiment, the concentration of a necrostatin-1s compound comprises a range of about 400 nM to about 500 nM. In another embodiment, the concentration of a necrostatin-1s compound comprises a range of about 500 nM to about 1 µM. In another embodiment, the concentration of a necrostatin-1s compound comprises a range of about 500 nM to about 600 nM. In another embodiment, the concentration of a necrostatin-1s compound comprises a range of about 600 nM to about 700 nM. In another embodiment, the concentration of a necrostatin-1s compound comprises a range of about 700 nM to about 800 nM. In another embodiment, the concentration of a necrostatin-1s compound comprises a range of about 800 nM to about 900 nM. In another embodiment, the concentration of a necrostatin-1s compound comprises a range of about 900 nM to about 1 µM. In another embodiment, the concentration of a necrostatin-1s compound comprises a range of about 1 µM to about 2 µM. In another embodiment, the concentration of a necrostatin-1s compound comprises a range of about 1 µM to about 1.1 µM. In another embodiment, the concentration of a necrostatin-1s compound comprises a range of about 1 µM to about 1.2 µM. In another embodiment, the concentration of a necrostatin-1s compound comprises a range of about 1.2 µM to about 1.3 µM. In another embodiment, the concentration of a necrostatin-1s compound comprises a range of about 1.3 µM to about 1.4 µM. In another embodiment, the concentration of a necrostatin-1s compound comprises a range of about 1.4 µM to about 1.5 µM. In another embodiment, the concentration of a necrostatin-1s compound comprises a range of about 1.5 µM to about 1.6 µM. In another embodiment, the concentration of a necrostatin-1s compound comprises a range of about 1.6 µM to about 1.7 µM. In another embodiment, the concentration of a necrostatin-1s compound comprises a range of about 1.7 µM to about 1.8 µM. In another embodiment, the concentration of a necrostatin-1s compound comprises a range of about 1.8 µM to about 1.9 µM. In another embodiment, the concentration of a necrostatin-1s compound comprises a range of about 1.9 µM to about 2.0 µM. In another embodiment, the concentration of a necrostatin-1s compound comprises a range of about 2 µM to about 200 µM. In another embodiment, the concentration of a necrostatin-1s compound comprises a range of about 200 µM to about 500 µM.

In one embodiment, the final concentration of necrostatin-1s compound comprised in a composition disclosed herein, or an analog, derivative, isomer, or pharmaceutically acceptable salt of the necrostatin-1s, is about 0.2 nM. In another embodiment, the final concentration of necrostatin-1s compound comprised in a composition disclosed herein, or an analog, derivative, isomer, or pharmaceutically acceptable salt thereof, is about 2.0 nM. In another embodiment, the final concentration of necrostatin-1s compound comprised in a composition disclosed herein, or an analog, derivative, isomer, or pharmaceutically acceptable salt thereof, is about 20 nM. In another embodiment, the final concentration of necrostatin-1s compound comprised in a composition disclosed herein, or an analog, derivative, isomer, or pharmaceutically acceptable salt thereof, is about 200 nM. In another embodiment, the final concentration of necrostatin-1s compound comprised in a composition disclosed herein, or an analog, derivative, isomer, or pharmaceutically acceptable salt thereof, is about 2 µM.

In one embodiment, the concentration of Bax channel inhibitor comprised in a composition disclosed herein comprises a range of about 0.5 nM to about 50 µM. In another embodiment, the concentration of Bax channel inhibitor comprises a range of about 0.5 nM to about 5 nM. In another embodiment, the concentration of Bax channel inhibitor comprises a range of about 5 nM to about 50 nM. In another embodiment, the concentration of Bax channel inhibitor comprises a range of about 50 nM to about 500 nM. In another embodiment, the concentration of Bax channel inhibitor comprises a range of about 500 nM to about 5 µM. In another embodiment, the concentration of Bax channel inhibitor comprises a range of about 5 µM to about 50 µM.

In one embodiment, the concentration of a 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 0.5 nM to about 50 µM. In another embodiment, the concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 0.5 nM to about 5 nM. In another embodiment, the concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 5 nM to about 50 nM. In another embodiment, the concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 50 nM to about 500 nM. In another embodiment, the concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 500 nM to about 5 µM. In another embodiment, the concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof comprises a range of about 5 µM to about 50 µM.

In one embodiment, the final concentration of said Bax channel inhibitor comprised in a composition disclosed herein is about 0.5 nM, in another embodiment, the final concentration of said Bax channel inhibitor comprised in a composition disclosed herein is about 5 nM. In another embodiment, the final concentration of said Bax channel inhibitor comprised in a composition disclosed herein is about 50 nM. In another embodiment, the final concentration of said Bax channel inhibitor disclosed herein is about 500 nM. In another embodiment, the final concentration of said Bax channel inhibitor comprised in a composition disclosed herein is about 5 µM. In another embodiment, the final concentration of said Bax channel inhibitor comprised in a composition disclosed herein is about 50 µM.

In one embodiment, the final concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof is about 0.5 nM. In another embodiment, the final concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof is about 5 nM. In another embodiment, the final concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof is about 50 nM. In another embodiment, the final concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof is about 500 nM. In another embodiment, the final concentration of 3,6-Dibromo-α-(1-piperazinylmethyl)-9H-carbazole-9-ethanol dihydrochloride compound comprised in a composition disclosed herein, or an analog, derivative, isomer, or pharmaceutically acceptable salt thereof is about 5 µM. In another embodiment, the final concentration of 3,6-Dibromo-α-(1-piperazinylinethyl)-9H-carbazole-9-ethanol dihydrochloride compound comprised in a composition disclosed herein, or an analog, derivative, isomer, or pharmaceutically acceptable salt thereof is about 50 µM.

In some embodiments, the compositions disclosed herein further comprise an Adenosine triphosphate (ATP). While not wishing to be bound by theory, it is believed that in some embodiments the loss of cellular ATP and reactive oxygen species are produced (both as the result of mitochondrial maladaptive process) are harmful to cells and further push toward necrotic signaling. In addition, in some embodiments, depletion of ATP allows $Ca^{2+}$ update by mitochondria, resulting in permeability transition pore (PTP) opening, which leads, in some embodiments, to cytochrome C release, mitochondrial swelling and death. Thus, in some embodiments, said ATP in the composition reverses or mitigates the loss of ATP due to cell membrane disruption caused by cell dissociation from tissue and cryopreservation, thereby relieving the necroptotic pressure. In additional embodiments, ATP in the composition preserves mitochondrial function through minimizing the slowdown in mitochondrial respiration and also aids in replenishment of lost cellular metabolites lost in the process of breaking up cells.

In one embodiment, said ATP is present at a concentration of from about 10 nM to about 1 nM. In another embodiment, said ATP is present at a concentration of from about 10 nM to about 100 nM. In another embodiment, said ATP is present at a concentration of from about 100 nM to about 1 µM. In another embodiment, said ATP is present at a concentration of from about 1 µM to about 10 µM. In another embodiment, said ATP is present at a concentration of from about 10 µM to about 100 µM. In another embodiment, said ATP is present at a concentration of from about 100 µM to about 100 mM.

In some embodiments, the final concentration of ATP comprised in a composition disclosed herein is about 10 nM. In another embodiment, the final concentration of ATP comprised in a composition disclosed herein is about 100 nM. In another embodiment, the final concentration of ATP comprised in a composition disclosed herein is about 1 µM. In another embodiment, the final concentration of ATP comprised in a composition disclosed herein is about 10 µM. In another embodiment, the final concentration of ATP comprised in a composition disclosed herein is about 100 µM. In another embodiment, the final concentration of ATP comprised in a composition disclosed herein is about 1 mM.

In some embodiments, the compositions disclosed herein further comprise a nicotinamide adenine dinucleotide (NAD) compound. While not wishing to be bound by theory, it is believed that, in some embodiments, the loss cellular of NAD additionally contributes to cellular necrosis through various mechanisms, including, in some embodiments, inhibition of glycolysis and decreasing activity of the sirtuin family of proteins. An additional effect of NAD depletion is, in some embodiments, the reduction of NADP/NADPH production. In some embodiments, NADPH provides the reducing equivalents for biosynthetic reactions and in protecting against the necroptotic-inducing signals of ROS (reactive oxygen species). Therefore, in some embodiments low NAD levels are believed to be a trigger for activation of several mediators of necroptotic cell death. Thus, in some embodiments, said NAD in the composition reverses or mitigates the loss of NAD due to cell membrane disruption caused, in some embodiments, by cell dissociation from tissue or cryopreservation. In other embodiments said NAD in the composition suppresses necroptotic signaling.

In some embodiments, replenishment of NAD prevents decrease of NAD levels in hippocampus and subsequent release of cathepsin B from lysosomes after ischemia/reperfusion injury. In some embodiments, high intracellular NAPDH causes CaMKII to phosphorylate and inactivate caspase-2, which has multiple effects including prevention of necrosis by keeping caspase-2 in its pro-caspase inactive enzyme form. In some embodiments, NAD also influences the differentiation state of cells, maintaining their active state to prevent de-differentiation and self-renewal programs. Thus, in some embodiments, the addition of NAD to the freezing composition prevents excessive cell death and loss by ensuring the regeneration of chemical reducing pathways. In addition, sufficient cellular NADPH, which derives from NAD, causes caspases to remain at sufficiently low activity to avoid cell death (necrosis) while preventing regression along the differentiation pathways. Thus, in some embodiments NAD in the composition suppresses cell differentiation and supports maintenance of cellular identity in cells experiencing stress due to membrane disruption caused, in some embodiments, by cell dissociation from tissue or cryopreservation.

In one embodiment, said NAD is present at a concentration of from about 5 nM to about 500 µM. In another embodiment, said NAD is present at a concentration of from about 5 nM to about 50 nM. In another embodiment, said NAD is present at a concentration of from about 5 nM to about 50 nM. In another embodiment, said NAD is present at a concentration of from about 50 nM to about 500 nM. In another embodiment, said NAD is present at a concentration of from about 500 nM to about 5 µM. In another embodiment, said NAD is present at a concentration of from about 5 µM to about 50 µM. In another embodiment, said NAD is present at a concentration of from about 50 µM to about 500 µM.

In one embodiment, the final concentration of NAD comprised in a composition disclosed herein is about 5 nM. In another embodiment, the final concentration of comprised in a composition disclosed herein is about 50 nM. In another embodiment, the final concentration of NAD comprised in a composition disclosed herein is about 500 nM. In another embodiment, the final concentration of NAD comprised in a composition disclosed herein is about 5 µM. In another embodiment, the final concentration of NAD comprised in a composition disclosed herein is about 50 µM. In another embodiment, the final concentration of NAD comprised in a composition disclosed herein is about 500 µM.

In some embodiments, the compositions disclosed herein further comprise Cyclosporin A. In one embodiment, the compositions disclosed herein further comprise an inhibitor of Cyclophilin D (CypD). In another embodiment, said inhibitor is Cyclosporin A. In some embodiments, Cyclosporin A is an immunosuppressant drug that interferes with the swelling of mitochondria secondary to calcium activation, and, in some embodiments, has been shown to protect against reactive oxygen species-induced necrotic death in many cell types, including liver. In some embodiments, Cyclophilin D (cypD) is a peptidyl-prolyl isomerase that resides in the mitochondrial matrix and controls the MPTP, and, in some embodiments, is central to the early determination of mitochondrial dysfunction leading to necrotic cell death.

While not wishing to be bound by theory, it is believed that, in some embodiments, cyclophilin D modulates regulated necrosis, or necroptosis, through controlling the opening state of the MPTP, and its inhibition by cyclosporin A was shown to be protective in calcium- and oxidative stress induced death of hepatocytes. In some embodiments, CypD inhibition also results in protection from ischemic injury, and, in some embodiments, can rescue several aspects of neurodegenerative diseases including muscular dystrophy and also in liver toxicity models. Thus, necroptosis resulting from ischemia-reperfusion injury is, in some embodiments, sensitive to CypD activity, implicating it directly in this form of injury-mediated cell death.

In one embodiment, said cyclosporin A is present at a concentration of from about 1 nM to about 1 mM. In another embodiment, said cyclosporin A is present at a concentration of from about 1 nM to about 10 nM. In another embodiment, said cyclosporin A is present at a concentration of from about 10 nM to about 100 nM. In another embodiment, said cyclosporin A is present at a concentration of from about 100 nM to about 1 µM. In another embodiment, said cyclosporin A is present at a concentration of from about 1 µM to about 10 µM. In another embodiment, said cyclosporin A is present at a concentration of from about 10 µM to about 100 µM. In another embodiment, said cyclosporin A is present at a concentration of from about 100 µM to about 1 mM.

In one embodiment, the final concentration of cyclosporin A comprised in a composition disclosed herein is about 1 nM. In another embodiment, the final concentration of cyclosporin A comprised in a composition disclosed herein is about 10 nM. In another embodiment, the final concentration of cyclosporin A comprised in a composition disclosed herein is about 100 nM. In another embodiment, the final concentration of cyclosporin A comprised in a composition disclosed herein is about 1 µM. In another embodiment, the final concentration of cyclosporin A comprised in a composition disclosed herein is about 10 µM. In another embodiment, the final concentration of cyclosporin A comprised in a composition disclosed herein is about 100 µM. In another embodiment, the final concentration of cyclosporin A comprised in a composition disclosed herein is about 1 mM.

In some embodiments, the compositions disclosed herein further comprise superoxide dismutase. In one embodiment, the superoxide dismutase is a Cu—Zn superoxide dismutase. In another embodiment, the superoxide dismutase is a Fe—Mn superoxide dismutase. In one embodiment, the superoxide dismutase is a mammalian superoxide dismutase. In another embodiment, the superoxide dismutase is human superoxide dismutase. Mammals have three types of superoxide dismutase: type 1, termed SOD-1 is the cytoplasmic form, type 2, termed SOD2, is the mitochondrial form, and type 3, termed SOD3, is the extracellular form.

While not wishing to be bound by theory, it is believed that removal of cells, tissues, or organs from their natural environment results, in some embodiments, in disruption of metabolic nourishment and normal oxygenation causing ischemia, which in turn leads, in some embodiments, to calcium overload and generation of excessive reactive oxygen species (ROS), such as peroxides, superoxide, and hydroxyl radicals. In some embodiments, high levels of reactive oxygen damage cellular structures and cause oxidative stress, thereby, in some embodiments, inducing necrosis. Thus, in some embodiments, said superoxide dismutase in the composition neutralizes the ischemia-induced reactive oxygen species. The superoxide dismutase can be, in one embodiment, native superoxide dismutase purified from a human or animal tissue. In another embodiment, superoxide dismutase is recombinant superoxide dismutase, expressed in human, animal or bacterial cell culture, and subsequently purified. Methods of expressing and purifying recombinant proteins are well known in the art. For example, see Sambrook et al. (MOLECULAR CLONING: A LABORATORY MANUAL (Sambrook et al, eds., Cold Spring Harbor Laboratory Press, Cold Spring Harbor, 1989), Ausubel et al. (CURRENT PROTOCOLS IN MOLECULAR BIOLOGY Ausubel et al., eds., John Wiley & Sons, New York, 1987).

In one embodiment, said superoxide dismutase is present at a concentration of from about 0.001 Kunitz Units (KU) to about 100 KU. In another embodiment, said superoxide dismutase is present at a concentration of from about 0.001 KU to about 0.01 KU. In another embodiment, said superoxide dismutase is present at a concentration of from about 0.01 KU to about 0.1 KU. In another embodiment, said superoxide dismutase is present at a concentration of from about 0.1 KU to about 1 KU. In another embodiment, said superoxide dismutase is present at a concentration of from about 1 KU to about 10 KU. In another embodiment, said superoxide dismutase is present at a concentration of from about 10 KU to about 100 KU.

In one embodiment, the final concentration of superoxide dismutase comprised in a composition disclosed herein is about 0.001 Kunitz Units (KU). In another embodiment, the final concentration of superoxide dismutase comprised in a composition disclosed herein is about 0.01 KU. In another embodiment, the final concentration of superoxide comprised in a composition disclosed herein is about 0.1 KU. In another embodiment, the final concentration of superoxide dismutase comprised in a composition disclosed herein is about 1 KU. In another embodiment, the final concentration of superoxide dismutase comprised in a composition disclosed herein is about 10 KU. In another embodiment, the final concentration of superoxide dismutase comprised in a composition disclosed herein is about 100 KU.

As used herein, the tem "Kunitz Units" denote units of enzymatic activity as defined in Kunitz assay (Kunitz M., 1950 Crystalline Deoxyribonuclease II. Digestion of Thymus Nucleic Acid. The Kinetics of Reaction: J. Gen. Physiol., 33 363-377).

In some embodiments, the compositions disclosed herein comprise a necroptosis inhibitor, for example a 5-((7-Chloro-1H-indol-3-yl)methyl)-3-methyl-2,4-imidazolidinedione compound or an analog, derivative, isomer, or pharmaceutically acceptable salt thereof, and a Bax channel inhibitor, for example a 3,6-Dibromo-a-(1-piperazinylmethyl)-9H-carbazole-9-ethanol dihydrochloride compound, or an analog, derivative, isomer, or pharmaceutically acceptable salt thereof, and further comprise a nicotinamide adenine dinucleotide (NAD), an adenosine triphosphate (ATP), a cyclosporin A, or a manganese superoxide dismutase or a zinc superoxide dismutase, or any combination thereof.

In some embodiments, the compositions disclosed herein, comprise a necrosis inhibitor, a Bax channel inhibitor, a nicotinamide adenine dinucleotide (NAD), an adenosine triphosphate (ATP), a cyclosporin A, or a manganese superoxide dismutase or a zinc superoxide dismutase, or any combination thereof.

In some embodiments, a compositions disclosed herein comprise a 5-((7-Chloro-1H-indol-3-yl)methyl)-3-methyl-2, 4-imidazolidinedione) compound, a 3,6-Dibromo-a-(1-piperazinylmethyl)-9H-carbazole-9-ethanol dihydrochloride compound, a nicotinamide adenine dinucleotide (NAD), an adenosine triphosphate (ATP), a cyclosporin A, and a manganese superoxide dismutase or a zinc superoxide dismutase. In some embodiments, a compositions disclosed herein comprises a 5-((7-Chloro-1H-indol-3-yl)methyl)-3-methyl-2,4-imidazolidinedione)compound, a 3,6-Dibromo-a-(1-piperazinylmethyl)-9H-carbazole-9-ethanol dihydrochloride compound, a nicotinamide adenine dinucleotide (NAD), an adenosine triphosphate (ATP), a cyclosporin A, or a manganese superoxide dismutase or a zinc superoxide dismutase, or any combination thereof.

In another embodiment, the composition disclosed herein comprises 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase or zinc superoxide dismutase (EVERGREEN™ Media Solution or EVERLAST™).

In further embodiments the composition disclosed herein further comprise cryoprotective agents. One of ordinary skill in the art would appreciate that term "cryoprotective agent" may encompass a chemical that minimizes ice crystal formation in a cellular sample (e.g. cell culture, tissue, or organ) when the sample is cooled to subzero temperatures and results in substantially no damage to the sample after warming, in comparison to the effect of cooling without the agent. Suitable cryoprotective agents can be either natural or synthetic and comprise polyvinyl pyrrolidone, dextran, maltodextrins, 2,3-butanediol, hydroxyethyl starch, polyethylene glycol, propylene glycol, glucose, glycerol, dimethylformamide, sucrose, raffinose, maltodextrin, stachyose, lactose, starch, trehalose, glucose, cyclodextrin (e.g., α-cyclodextrin, β-cyclodextrin, γ-cyclodextrin or mixtures thereof), mannitol, dextrose, carboxymethyl cellulose, serum (either human, animal or synthetic replacements with supplements that are essential for proper nutritive support), and other commonly used agents (such as pH stabilizers, sugars, amino acids, stabilizers, antibiotics), or combinations thereof, each representing an independent embodiment of a composition disclosed herein. Multiple additional cryoprotective agents are known in the art (see, e.g. U.S. Pat. No. 8,440,390, hereby incorporated by reference in its entirety).

In some embodiments, the amount of a cryoprotective agent in a composition disclosed herein comprises a range from 1% by weight to 15% by weight. In some embodiments, the amount is about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at least about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at most about 1 wt %, 2 wt %, 3 wt %, 4 wt %, 5 wt %, about 6 wt %, 7 wt %, 8 wt %, 9 wt %, 10 wt %, or 15 wt %.

In some embodiments, the cryoprotective agent of the present compositions comprises dimethyl sulfoxide (DMSO). In some embodiments, the amount of DMSO in a composition disclosed herein comprises a range from 1% by weight to 15% weight. In some embodiments, the amount of DMSO in a composition disclosed herein comprises a range from 3% by weight to 10% weight. In some embodiments, the amount is about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at least about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at most about 1 wt %, 2 wt %, 3 wt %, 4 wt %, 5 wt %, about 6 wt %, 7 wt %, 8 wt %, 9 wt %, 10 wt %, or 15 wt %.

In some embodiments, the cryoprotective agent of the present compositions comprises serum. In one embodiment, serum comprises human serum, animal serum, or synthetic serum replacements that may include supplements that are essential for proper nutritive support of cells, tissues, and/or organs. In another embodiment, serum comprises human serum. In another embodiment, serum comprises animal serum. In another embodiment, serum comprises synthetic serum replacements. In another embodiment, synthetic serum replacements include supplements that are essential for proper nutritive support of cells, tissues, and/or organs.

In some embodiments, the amount of serum in a composition disclosed herein comprises a range from 1% by weight to 15% weight. In some embodiments, the amount of serum in a composition disclosed herein comprises a range from 3% by weight to 10% weight. In some embodiments, the amount is about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at least about 1 wt %, 2 wt %, 3 wt %, 4 wt %, 5 wt %, about 6 wt %, 7 wt %, 8 wt %, 9 wt %, 10 wt %, or 15 wt %. In some embodiments, the amount is at most about 1 wt %, 2 wt %, 3 wt %, 4 wt %, 5 wt %, about 6 wt %, 7 wt %, 8 wt %, 9 wt %, 10 wt %, or 15 wt %.

In some embodiments, compositions disclosed herein further comprise a cryoprotective agent comprising DMSO or serum, or any combination thereof. In come embodiments, compositions disclosed herein further comprise any cryoprotective agent known in the art.

In some embodiments, compositions disclosed herein further comprise a pharmaceutically acceptable excipients or carriers.

In one, embodiment, the compositions disclosed herein comprise a necrosis inhibitor, a Bax channel inhibitor, nicotinamide adenine dinucleotide (NAD), adenosine triphosphate (ATP), cyclosporin A, and manganese superoxide dismutase or zinc superoxide dismutase, a cryoprotective agent, and a pharmaceutically acceptable carrier or excipient.

In another embodiment, the compositions disclosed herein comprise 5-((7-Chloro-1H-indol-3-yl)methyl)-3-methyl-2,4-imidazolidinedione), 3,6-Dibromo-a-(1-piperazinylmethyl)-9H-carbazole-9-ethanol dihydrochloride, nicotinamide adenine dinucleotide (NAD), adenosine triphosphate (ATP), cyclosporin A, manganese superoxide dismutase or zinc superoxide dismutase, a cryoprotective agent, and a pharmaceutically acceptable carrier or excipient.

In another embodiment, the compositions disclosed herein comprise 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase or zinc superoxide dismutase, a cryoprotective agent, and a pharmaceutically acceptable carrier or excipient.

One of ordinary skill in the art would appreciate that term "pharmaceutically acceptable" in reference to carriers and excipients, may encompass compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

One of ordinary skill in the art would appreciate that term "pharmaceutically-acceptable carrier" may encompass a pharmaceutically-acceptable material, composition or vehicle, such as a liquid or solid filler, diluent, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers and s include: sugars, such as lactose, glucose and sucrose; starches, such as corn starch and potato starch; cellulose, and its derivatives, such as sodium carboxymethyl cellulose, ethyl cellulose and cellulose acetate; surfactants, such as polysorbate 80 (i.e. Tween 80); powdered tragacanth; malt; gelatin; talc; s, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

In some embodiments, the compositions disclosed herein comprise one or more pharmaceutical excipients or other additives. Such excipients or additives can include one or more stabilizing polyols, e.g., higher polysaccharides/polymers (for promoting controlled release), magnesium stearate, leucine or trileucine (as lubricants), and phospholipids or surfactants.

One of ordinary skill in the art would appreciate that term "pharmaceutically acceptable excipient" may encompass any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palm itate, shellac, silicon dioxide, sodium carboxym ethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

One of ordinary skill in the art would appreciate that terra "pH-stabilizer" may encompass buffers and pH-altering agents. Suitable pH-stabilizing agents include tribasic sodium phosphate, anhydrous sodium carbonate, glycine, citric acid and the like or mixtures thereof. Flavouring agents are well known to persons skilled in the art and include, but are not limited to fruity flavours. Frescofort Flavour Permaseal, Grenadine Flavour Permaseal and Tutti Frutti Flavour or combinations thereof.

One of ordinary skill in the art would appreciate that term "sugar" may encompass all known monosaccharides, disaccharides and/or oligosaccharides, for example, sucrose (saccharose), glucose, fructose, maltose, lactose, galactose and/or starch hydrolyzates that are usual in the pharmaceutical industry. An embodiment of the inventive composition is characterized in that it particularly contains sucrose as sugar.

One of ordinary skill in the art would appreciate that term "amino acid" may encompass one of the naturally occurring amino carboxylic acids of which proteins are comprised, or a synthetic amino acids not found in nature.

One of ordinary skill in the art would appreciate that term "antibiotic" may encompass pharmacologically active substances for the treatment of microbial infectious diseases, including broad-spectrum antibiotics, which are effective against many families of microbes, and narrow-spectrum antibiotics, which are specifically effective against individual microbe species.

In one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

In some embodiments, the term "comprise" or grammatical forms thereof, refers to the inclusion of the indicated active agents, such as the compounds disclosed herein, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredients are the indicated active ingredients, however, other compounds may be included which are for stabilizing, preserving, etc. the formulation, but are not involved directly in the therapeutic effect of the indicated active ingredient. In some embodiments, the term "consisting essentially of" may refer to components, which exert a therapeutic effect via a mechanism distinct from that of the indicated active ingredients. In some embodiments, the term "consisting essentially of" may refer to components, which exert a therapeutic effect and belong to a class of compounds distinct from that of the indicated active ingredients. In some embodiments, the term "consisting essentially of" may refer to components, which exert a therapeutic effect and belong to a class of compounds distinct from that of the indicated active ingredients, by acting via a different mechanism of action, disclosed herein In some embodiments, the term "consisting essentially of" may refer to components which facilitate the release of the active ingredients. In some embodiments, the term "consisting" refers to a composition, which contains the active ingredients and a pharmaceutically acceptable carrier or excipient.

In some embodiments, the compositions disclosed herein, consist essentially of a necrosis inhibitor, a Bax channel inhibitor, a nicotinamide adenine dinucleotide (NAD), an adenosine triphosphate (NIP), a cyclosporin A, or a manganese superoxide dismutase or a zinc superoxide dismutase, or any combination thereof, in some embodiments, the compositions disclosed herein, consist essentially of a necroptosis inhibitor, a Bax channel inhibitor, a nicotinamide adenine dinucleotide (NAD), an adenosine triphosphate (ATP), a cyclosporin A, or a manganese superoxide dismutase or a zinc superoxide dismutase, or any combination thereof.

In some embodiments, a compositions disclosed herein consists essentially of a 5-((7-Chloro-1H-indol-3-yl)methyl)-3-methyl-2,4-imidazolidinedione) compound, a 3,6-Dibromo-a-(1-piperazinylmethyl)-9H-carbazole-9-ethanol dihydrochloride compound, a nicotinamide adenine dinucleotide (NAD), an adenosine triphosphate (ATP), a cyclosporin A, and a manganese superoxide dismutase or a zinc superoxide dismutase. In some embodiments, a compositions disclosed herein consists essentially of a 5-((7-Chloro-1H-indol-3-yl)methyl)-3-methyl-2,4-imidazolidinedione) compound, a 3,6-Dibromo-a-(1-piperazinylinethyl)-9H-carbazole-9-ethanol dihydrochloride compound, a nicotinamide adenine dinucleotide (NAD), an adenosine triphosphate (ATP), a cyclosporin A, or a manganese superoxide dismutase or a zinc superoxide dismutase, or any combination thereof.

In another embodiment, the compositions disclosed herein consists essentially of 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 μM adenosine triphosphate (ATP), 0.01 μM cyclosporin A, and 0.1 Kuntz Unit manganese superoxide dismutase or zinc superoxide dismutase.

In some embodiments, the compositions disclosed herein, consist of a necrosis inhibitor, a Bax channel inhibitor, a nicotinamide adenine dinucleotide (NAD), an adenosine triphosphate (ATP), a cyclosporin A, or a manganese superoxide dismutase or a zinc superoxide dismutase, or any combination thereof. In some embodiments, the compositions disclosed herein, consist of a necroptosis inhibitor, a Bax channel inhibitor, a nicotinamide adenine dinucleotide (NAD), an adenosine triphosphate (ATP), a cyclosporin A, or a manganese superoxide dismutase or a zinc superoxide dismutase, or any combination thereof.

In some embodiments, a compositions disclosed herein consists of a 5-((7-Chloro-1H-indol-3-yl)methyl)-3-methyl-2,4-imidazolidinedione) compound, a 3,6-Dibromo-a-(1-piperazinytmethyl)-9H-carbazole-9-ethanol dihydrochloride compound, a nicotinamide adenine dinucleotide (NAD), an adenosine triphosphate (ATP), a cyclosporin A, and a manganese superoxide dismutase or a zinc superoxide dismutase. In some embodiments, a compositions disclosed herein consist of a 5-((7-Chloro-1-indol-3-yl)methyl)-3-methyl-2,4-imidazolidinedione) compound, a 3,6-Dibromo-a-(1-piperazinylmethyl)-9H-carbazole-9-ethanol dihydrochloride compound, a nicotinamide adenine dinucleotide (NAD), an adenosine triphosphate (ATP), a cyclosporin A, or a manganese superoxide dismutase or a zinc superoxide dismutase, or any combination thereof.

In another embodiment, the compositions disclosed herein consist of 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 μM adenosine triphosphate (ATP), 0.01 μM cyclosporin A, and 0.1 Kuntz Unit manganese superoxide dismutase or zinc superoxide dismutase.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments disclosed herein may be presented in a range format. It should be understood that the description in range format is merely for convenience and brevity and should not be construed as an inflexible limitation on the scope of a composition disclosed herein. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

Kits

Furthermore, disclosed herein are ready-to-use kits comprising the elements of the compositions described above. In some embodiments, the kits comprise the compounds or compositions disclosed herein and one or more other ingredients suitable for methods of use described herein. In some embodiments, the kits comprise a necrosis inhibitor, or an analog, derivative, isomer, or pharmaceutically acceptable salt thereof, and a Bax channel inhibitor compound, or an analog, derivative, isomer, or pharmaceutically acceptable salt thereof. In some embodiments, the kits comprise a necroptosis inhibitor, or an analog, derivative, isomer, or pharmaceutically acceptable salt thereof, and a Bax channel inhibitor compound, or an analog, derivative, isomer, or pharmaceutically acceptable salt thereof. In some embodiments, the kits comprise a necrostatin-1s compound, or an analog, derivative, isomer, or pharmaceutically acceptable salt thereof, and a Bax channel inhibitor compound, or an analog, derivative, isomer, or pharmaceutically acceptable salt thereof. In some embodiments, the kits further comprise a nicotinamide adenine dinucleotide (NAD), an adenosine triphosphate (ATP), a cyclosporine A, or a superoxide dismutase, or any combination thereof.

In some embodiments, one or more of the elements of compositions are provided as dry powder to be reconstituted. In such embodiments, the kit may further comprise a desiccant. In some embodiments, one or more elements of compositions are provided as liquid. In some embodiments, the elements of the compositions are provided in the kits in individual vials for preparation of compositions prior to use, generally by mixing the compounds or elements with the other ingredients or by applying the compounds or compositions to the other ingredients, e.g. supplementing cell growth medium with the compositions. In some embodiments, the kits may further comprise one or more of cryoprotective agents, carriers or excipients. In some embodiments, the kit may further comprise a combination of more than one of these additional components.

In some embodiments, the kits further comprise all necessary brackets and containers for mixing and preparation of the compositions for administration. In some embodiments, the elements of the compositions in the kits are pre-mixed. In some embodiments, the composition of the kit is sterile. In some embodiments, the kits further comprise packaging materials. In some specific embodiments, the packaging materials are air-tight. In these embodiments, the packaging materials may optionally be filled with an inert gas, such as, for example, nitrogen, argon, or the like. In some embodiments, the packaging materials comprise a metal foil container, such as, for example, a sealed aluminum pouch or the like. Such packaging materials are well known by those of ordinary skill in the art. In additional embodiments, the kits further comprise instructions describing how to combine the elements or compounds of disclosed compositions, and, optionally, how to combine disclosed compositions with other ingredients (e.g. a cryoprotective agent, a carrier an excipient) to form a composition for administration.

Methods

In some embodiments, the compositions disclosed herein act to prevent progression of the necrosis pathways during freeze-thaw cycles and to repair physical, chemical, and thermodynamic damage that result from cell manipulations in vitro and during liberation from tissue. In some embodiments, compositions disclosed herein act to suppress necrosis in cells, tissues, or organs undergoing cryopreservation. In some embodiments, compositions disclosed herein act to in inhibit, or reduce the incidence of cellular plasticity, necroptosis, or necrosis in cells, tissues or organs. In some embodiments, compositions, disclosed herein are useful in treating, preventing, inhibiting, or reducing the incidence of cellular plasticity, necroptosis, or necrosis associated with aging or disease, in a subject. In some embodiments, compositions disclosed herein may be used in a method of cryopreservation of a plurality of cells. In some embodiments, compositions disclosed herein may be used in a method of treating, preventing, inhibiting, or reducing the incidence of cellular plasticity, or necroptosis or necrosis in a plurality of cells.

Compositions for use in the methods disclosed herein have been described above. In some embodiments, any of the compositions described herein may be used in a method of use described herein. In some embodiments, the combinations and concentrations of components comprised within a composition for use in the methods described herein have been described in detail above.

In one embodiment provided herein is a method for cryopreservation, the method comprising the steps of (a) bringing a plurality of cells in contact with a composition disclosed herein; and (b) cooling the composition comprising the plurality of cells of step (a).

In one embodiment, provided herein is a method for cryopreservation, the method comprising the steps of (a), bringing a plurality of cells in contact with a composition comprising a necroptosis inhibitor and a Bax channel inhibitor; and (b) cooling the composition comprising the plurality of cells of step (a). Non-limiting examples of necroptosis inhibitors and Bax channel inhibitors have been disclosed in detail above. In another embodiment, provided herein is a method for cryopreservation, the method comprising the steps of (a), bringing a plurality of cells in contact with a composition comprising a necroptosis inhibitor comprising a necrostatin-1s compound, or an analog, derivative, isomer, or pharmaceutically acceptable salt thereof, and a Bax channel inhibitor comprising a 3,6-dibromo-α-(1-piperazinylmethyl)-9H-carbazole-9-ethanol dihydrochloride or an analog, a derivative, an isomer, or a pharmaceutically acceptable salt thereof; and (b) cooling the composition comprising the plurality of cells.

In another embodiment, provided herein is a method for cryopreservation, the method comprising the steps of (a) bringing a plurality of cells in contact with a composition comprising a necroptosis inhibitor compound, or an analog, derivative, isomer, or pharmaceutically acceptable salt thereof, and a Bax channel inhibitor, or an analog, derivative, isomer, or pharmaceutically acceptable salt thereof, and further comprising a nicotinamide adenine dinucleotide (NAD), an adenosine triphosphate (ATP), a cyclosporine A, a manganese superoxide dismutase, a zinc-superoxide dismutase, or any combination thereof; and (b) cooling the composition comprising the plurality of cells. In another embodiment, provided herein is a method for cryopreservation, the method comprising the steps of (a), bringing a plurality of cells in contact with a composition comprising a necroptosis inhibitor compound, and a Bax channel inhibitor, and further comprising a nicotinamide adenine dinucleotide (NAD), an adenosine triphosphate (ATP), a cyclosporine A, a manganese-superoxide dismutase, a zinc-superoxide dismutase, or any combination thereof; and (b) cooling the composition comprising the plurality of cells, wherein the necroptosis inhibitor compound comprises a 5-((7-chloro-1H-indol-3-yl)methyl)-3-methyl-2,4-imidazolidinedione compound or an analog, a derivative, an isomer, or a pharmaceutically acceptable salt thereof, and wherein the Bax channel inhibitor compound comprises a 3,6-dibromo-α-(1-piperazinylmethyl)-9H-carbazole-9-ethanol dihydrochloride or an analog, a derivative, an isomer, or a pharmaceutically acceptable salt thereof.

In another embodiment, provided herein is a method for cryopreservation, the method comprising the steps of (a), bringing a plurality of cells in contact with a composition comprising a necroptosis inhibitor compound, a Bax channel inhibitor compound, and further comprising a nicotinamide adenine dinucleotide (NAD), an adenosine triphosphate (ATP), a cyclosporine A, a manganese-superoxide dismutase, a zinc-superoxide dismutase, or any combination thereof; and (b) cooling the composition comprising the plurality of cells, wherein the necroptosis inhibitor compound comprises a 5-((7-chloro-1H-indol-3-yl)methyl)-3-methyl-2,4-imidazolidinedione compound or an analog, a derivative, an isomer, or a pharmaceutically acceptable salt thereof, a 3-p-Methoxyphenyl-5,6-tetramethylenothieno[2,3-d]pyrimidin-4-one-2-mercaptoethylcyanide compound or a derivative, an isomer, or a pharmaceutically acceptable salt, a (Z)-5((3-(4-Fluorophenyl)-1H-pyrazol-4-yl)methylene)-2-imino-3-(thiazol-2-yl)thiazolidin-4-one or a derivative, an isomer, or a pharmaceutically acceptable salt thereof, a 5-(Indol-3-ylmethyl)-(2-thio-3-methyl)hydantoin or a derivative, an isomer, or a pharmaceutically acceptable salt thereof, a methyl-thiohydantoin-tryptophan compound, or a derivative, an isomer, or a pharmaceutically acceptable salt thereof, a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone or a derivative, an isomer, or a pharmaceutically acceptable salt thereof, a (S)—N-(1-[2-chloro-6-fluorophenyl]ethyl)-5-cyano-1-methyl-1H-pyrrole-2-carboxamide or a derivative, an isomer, or a pharmaceutically acceptable salt thereof a (E)-N-(4-(N-(3-Methoxypyrazin-2-yl)sulfamoyl)phenyl)-3-(5-nitrothiophene-2-yl)acrylamide or a derivative, an isomer, or a pharmaceutically acceptable salt thereof, a 1-(4-(4-Aminofuro[2,3-d]pyrimidin-5-yl)phenyl)-3-(2-fluoro-5-(trifluoromethyl)phenyl)urea, or 2,2-dimethyl-1-(5(S)-phenyl-4,5-dihydro-pyrazol-1-yl)-propan-1-one, or a derivative, an isomer, or a pharmaceutically acceptable salt thereof, and wherein the Bax channel inhibitor comprises a 3,6-dibromo-α-(1-piperazinylmethyl)-9H-carbazole-9-ethanol dihydrochloride or an analog, a derivative, an isomer, or a pharmaceutically acceptable salt thereof.

In another embodiment, provided herein is a method for cryopreservation, the method comprising the steps of (a), bringing a plurality of cells in contact with a composition comprising about 0.2 nM-2 µM 5-((7-chloro-1H-indol-3-yl)methyl)-3-methyl-2,4-imidazolidinedione compound, or an analog, a derivative, an isomer, or a pharmaceutically acceptable salt thereof, about 0.5 nM-50 µM 3,6-Dibromo-a-(1-piperazinylmethyl)-9H-carbazole-9-ethanol dihydrochloride compound, or an analog, a derivative, an isomer, or a pharmaceutically acceptable salt thereof, about 5 nM-500 µM nicotinamide adenine dinucleotide (NAD), about 10 nM-1 mM adenosine triphosphate (ATP), about 1 nM-1 mM cyclosporin A, and 0.001 KU-100 KU manganese-superoxide dismutase, zinc-superoxide dismutase, or any combination thereof; and (b) cooling composition comprising the plurality of cells. In another embodiment, provided herein is a method for cryopreservation, the method comprising the steps of (a), bringing a plurality of cells in contact with a composition comprising about 20 nM 5-((7-chloro-1H-indol-3-yl)methyl)-3-methyl-2,4-imidazolidinedione compound, or an analog, a derivative, an isomer, or a pharmaceutically acceptable salt thereof, about 5 nM 3,6-Dibromo-a-(1-piperazinylmethyl)-9H-carbazole-9-ethanol dihydrochloride compound, or an analog, a derivative, an isomer, or a pharmaceutically acceptable salt thereof, about 50 µM nicotinamide adenine dinucleotide (NAD), about 10 nM adenosine triphosphate (ATP), about 10 nM cyclosporin A, and about 0.1 KU manganese-superoxide dismutase, zinc-superoxide dismutase, or any combination thereof; and (b) cooling the composition comprising the plurality of cells. In another embodiment, provided herein is a method for cryopreservation, the method comprising the steps of (a), bringing a plurality of cells in contact with any composition disclosed herein, as described hereinabove and (b) cooling the composition comprising the plurality of cells.

In another embodiment, provided herein is a method for treating, preventing, inhibiting, or reducing the incidence of cellular plasticity, necroptosis, or necrosis in a plurality of cells, the method comprising the step of: bringing the plurality of cells in contact with a composition disclosed herein. In another embodiment, provided herein is a method for treating, preventing, inhibiting, or reducing the incidence of cellular plasticity, necroptosis, or necrosis in a plurality of cells, the method comprising the step of: bringing the plurality of cells in contact with a composition comprising a necroptosis inhibitor compound and a Bax channel inhibitor compound, in another embodiment, provided herein is a method for treating, preventing, inhibiting, or reducing the incidence of cellular plasticity, necroptosis, or necrosis, in a plurality of cells, the method comprising the step of: bringing the plurality of cells in contact with a composition comprising a necroptosis inhibitor compound and a Bax channel inhibitor, wherein the necroptosis inhibitor compound comprises a 5-((7-chloro-1H-indol-3-yl)methyl)-3-methyl-2,4-imidazolidinedione compound or an analog, a derivative, an isomer, or a pharmaceutically acceptable salt thereof, and wherein the Bax channel inhibitor comprises a 3,6-dibromo-α-(1-piperazinylethyl)-9H-carbazole-9-ethanol dihydrochloride, or an analog, a derivative, an isomer, or a pharmaceutically acceptable salt thereof.

In another embodiment, provided herein is a method for treating, preventing, inhibiting, or reducing the incidence of cellular plasticity, necroptosis, or necrosis, in a plurality of cells, the method comprising the steps of: bringing the plurality of cells in contact with a composition comprising a necroptosis inhibitor compound, and a Bax channel inhibitor, and further comprising a nicotinamide adenine dinucleotide (NAD), an adenosine triphosphate (ATP), a cyclosporine A, a manganese-superoxide dismutase, a zinc-superoxide dismutase, or any combination thereof, wherein the necroptosis inhibitor compound comprises a 5-((7-chloro-1H-indol-3-yl)methyl)-3-methyl-2,4-imidazolidinedione compound or an analog, a derivative, an isomer, or a pharmaceutically acceptable salt thereof, and wherein the Bax channel inhibitor comprises a 3,6-dibromo-α-(1-piperazinylmethyl)-9H-carbazole-9-ethanol dihydrochloride, or an analog, a derivative, an isomer, or a pharmaceutically acceptable salt thereof.

In another embodiment, provided herein is a method for treating, preventing, inhibiting, or reducing the incidence of cellular plasticity, necroptosis, or necrosis, in a plurality of cells, the method comprising the step of bringing the plurality of cells in contact with a composition comprising a necroptosis inhibitor compound, and a Bax channel inhibitor, and further comprising a nicotinamide adenine dinucleotide (NAD), an adenosine triphosphate (ATP), a cyclosporine A, a manganese-superoxide dismutase, a zinc-superoxide dismutase, or any combination thereof, wherein the necroptosis inhibitor compound comprises a 5-((7-chloro-1H-indol-3-yl)methyl)-3-methyl-2,4-imidazolidinedione compound, a 3-p-Methoxyphenyl-5,6-tetramethylenothieno[2,3-d]pyrimidin-4-one-2-mercaptoethylcyanide compound, a (Z)-5-((3-(4-Fluorophenyl)-1H-pyrazol-4-yl)methylene)-2-imino-3-(thiazol-2-yl)thiazolidin-4-one, a 5-(Indol-3-ylmethyl)-(2-thio-3-methyl)hydantoin, a methyl-thiohydantoin-tryptophan compound, a 1-([3S,3aS]-3-[3-fluoro-4-[trifluoromethoxy]phenyl]-8-methoxy-3,3a,4,5-tetrahydro-2H-benzo[g]indazol-2-yl)-2-hydroxyethanone, a (S)—N-(1-[2-chloro-6-fluorophenyl]ethyl)-5-cyano-1-methyl-1H-pyrrole-2-carboxamide, a (E)-N-(4-(N-(3-Methoxypyrazin-2-yl)sulfamoyl)phenyl)-3-(5-nitrothiophene-2-yl)acrylamide, a 1-(4-(4-Aminofuro[2,3-d]pyrimidin-5-yl)phenyl)-3-(2-fluoro-5-(trifluoromethyl)phenyl)urea, or 2,2-dimethyl-1-(5(S)-phenyl-4,5-dihydro-pyrazol-1-yl)-propan-1-one, or a derivative, an isomer, or a pharmaceutically acceptable salt of any one of said necroptosis inhibitor compounds, and wherein the Bax channel inhibitor comprises a 3,6-dibromo-α-(1-piperazinylmethyl)-9H-carbazole-9-ethanol dihydrochloride, or an analog, a derivative, an isomer, or a pharmaceutically acceptable salt thereof.

In another embodiment, provided herein is a method for treating, preventing, inhibiting, or reducing the incidence of cellular plasticity, necroptosis, or necrosis, in a plurality of cells, the method comprising the step of: bringing the plurality of cells in contact with a composition comprising about 0.2 nM-2 μM 5-((7-chloro-1H-indol-3-yl)methyl)-3-methyl-2,4-imidazolidinedione compound, or an analog, a derivative, an isomer, or a pharmaceutically acceptable salt thereof, about 0.5 nM-50 μM 3,6-Dibromo-a-(1-piperazinyl-methyl)-9H-carbazole-9-ethanol dihydrochloride compound, or an analog, a derivative, an isomer, or a pharmaceutically acceptable salt thereof, about 5 nM-500 μM nicotinamide adenine dinucleotide (NAD), about 10 nM-1 mM adenosine triphosphate (ATP), about 1 nM-1 mM cyclosporin A, and 0.001 KU-100 KU manganese-superoxide dismutase, zinc-superoxide dismutase, or any combination thereof. In another embodiment, provided herein is a method, for treating, preventing, inhibiting, or reducing the incidence of cellular plasticity, necroptosis, or necrosis, in a plurality of cells, the method comprising the step of: bringing the plurality of cells in contact with a composition comprising about 20 nM 5-((7-chloro-1H-indol-3-yl)methyl)-3-methyl-2,4-imidazolidinedione compound, or an analog, a derivative, an isomer, or a pharmaceutically acceptable salt thereof, about 5 nM 3,6-Dibromo-a-(1-piperazinylmethyl)-9H-carbazole-9-ethanol dihydrochioride compound, or an analog, a derivative, an isomer, or a pharmaceutically acceptable salt thereof, about 50 μM nicotinamide adenine dinucleotide (NAD), about 10 nM adenosine triphosphate (ATP), about 10 nM cyclosporin A, and about 0.1 KU manganese-superoxide dismutase, zinc-superoxide dismutase, or any combination thereof. In another embodiment, provided herein is a method, for treating, preventing, inhibiting, or reducing the incidence of cellular plasticity, necroptosis, or necrosis, in a plurality of cells, the method comprising the step of: bringing the plurality of cells in contact with a composition disclosed herein.

In some embodiments, necroptosis or necrosis is associated with aging or disease. One of ordinary skill in the art would appreciate that term "disease" may encompass a particular abnormal condition, a disorder of structure or function, that affects part or all of an organism, and which involves cellular plasticity, necroptosis, or necrosis. In one embodiment, the disease is myocardial infarction. In another embodiment, the disease is diabetes secondary to beta-cell necroptosis. In another embodiment, the disease is cholestatic liver disease. In another embodiment, the disease is stroke. In another embodiment, the disease is organ ischemia. In another embodiment, the disease is ischemia-reperfusion injury. In another embodiment, the disease is liver disease. In another embodiment, the disease is necrosis from cancer chemotherapy or radiation therapy. In another embodiment, the disease is traumatic brain injury. In another embodiment, the disease is necrotizing pancreatitis. In another embodiment, the disease is pathogen-induced necroptosis. In another embodiment, the disease is inflammation. In another embodiment, the disease is a neurodegenerative disease. In some embodiments, the disease comprises myocardial infarction, diabetes secondary to beta-cell necroptosis, cholestatic liver disease, stroke, organ ischemia, ischemia-reperfusion injury, liver disease, necrosis from cancer chemotherapy or radiation therapy, traumatic brain injury, necrotizing pancreatitis, pathogen-induced necroptosis, inflammation, a neurodegenerative disease.

In some embodiments, methods disclosed herein for preventing, inhibiting, or reducing the incidence of cellular plasticity, or necrosis or necroptic death, in a plurality of cells, are used during isolation, manipulation, low temperature culturing, or cryopreservation and freeze-thaw cycles thereof, of said plurality of cells. In some embodiments, methods for preventing, inhibiting, or reducing the incidence of cellular plasticity, or necrosis or necroptic death, comprises in vitro, ex vivo, or in vivo use.

One of ordinary skill in the art would appreciate that term "plurality of cells" may encompass any mammalian cell or group of cells either in vivo or grown in an in vitro culture, or maintained in an ex vivo culture. The groups of cells contemplated for the methods of use disclosed herein, include an multicellular sample. In some embodiment, multicellular samples comprise a single cell type or multiple cell types, a tissue, an organ, a portion of an organ, a specific segment of a whole organism, whether within an organism or removed or extracted from an organism. In another embodiment, a plurality of cells comprises an entire organism.

In some embodiments, the compositions disclosed herein are suitable for use with any cell type, whether cultured in vitro, in vivo, or ex-vivo including primary cells comprising stem cells, adult cells, transdifferentiated cells, dedifferentiated cells, differentiated cells. In some embodiments, the cell types compatible with the disclosed methods include reproductive cells (oocytes and spermatocytes), stem cells, Acinar cells, Adipocytes, Alveolar cells, Ameloblasts, Annulus Fibrosus Cells, Arachnoidal cells, Astrocytes, Blastoderms, Calvarial Cells, Cancerous cells (Adenocarcinomas, Fibrosarcomas, Glioblastomas, Hepatomas, Melanomas, Myeloid Leukemias, Neuroblastomas, Osteosarcomas, Sarcomas) Cardiomyocytes, Chondrocytes, Chordoma Cells, Chromaffin Cells, Cumulus Cells, Endothelial cells, Endothelial-like cells, Ensheathing cells, Epithelial cells, Fibroblasts, Fibroblast-like cells, Germ cells, Hepatocytes, Hybridomas, Insulin producing cells, Intersticial Cells, Islets, Keratinocytes, Lymphocytic cells, Macrophages, Mast cells, Melanocytes, Meniscus Cells, Mesangial cells, Mesenchymal Precursor Cells, Monocytes, Mononuclear Cells, Myeloblasts, Myoblasts, Myofibroblasts, Neuronal cells, Nucleus cells, Odontohlasts, Oocytes, Osteoblasts, Osteoblast-like cells, Osteoclasts, Osteoclast precursor cells, Oval Cells, Papilla cells, Parenchymal cells, Pericytess, Peridontal Ligament Cells, Periosteal cells, Platelets, Pneumocytes, Preadipocytes, Proepicardium cells, Renal cells, Salisphere cells, Schwann cells, Secretory cells, Smooth Muscle cells, Sperm cells, Stellate Cells, Stem Cells, Stem Cell-like cells, Stertoli Cells, Stromal cells, Synovial cells, Synoviocytes, T Cells, Tenocytes, T-lymphoblasts, Trophoblasts, Urothelial cells, Vitreous cells, and the like; said cells originating from, for example and without limitation, any of the following tissues: Adipose Tissue, Adrenal gland, Amniotic Amniotic sac, Aorta, Artery (Carotid, Coronary, Pulmonary), Bile Duct, Bladder, Blood, Bone, Bone Marrow, Brain (including Cerebral Cortex), Breast, Bronchi, Cartilage, Cervix, Chorionic Colon, Conjunctiva, Connective Tissue, Cornea, Dental Pulp, Duodenum, Dura Mater, Ear, Endometriotic cyst, Endometrium, Esophagus, Eye, Foreskin, Gallbladder, Ganglia, Gingiva, Head/Neck, Heart, Heart Valve, Hippocampus, Iliac, Intervertebral Disc, Joint, Jugular vein, Kidney, Knee, Lacrimal. Gland, Ligament, Liver, Lung, Lymph node, Mammary gland, Mandible, Meninges, Mesoderm, Microvasculature, Mucosa, Muscle-derived (MD), Myeloid Leukemia, Myeloma, Nasal, Nasopharyngeal, Nerve, Nucleus Pulposus, Oral Mucosa, Ovary, Pancreas, Parotid Gland, Penis, Placenta, Prostate, Renal, Respiratory Tract, Retina, Salivary Gland, Saphenous Vein, Sciatic Nerve, Skeletal Muscle, Skin, Small Intestine, Sphincter, Spine, Spleen, Stomach, Synovium, Teeth, Tendon, Testes, Thyroid, Tonsil, Trachea, Umbilical Artery, Umbilical Cord, Umbilical Cord Blood, Umbilical Cord Vein, Umbilical Cord (Wartons Jelly), Urinary tract, Uterus, Vasculature, Ventricle, Vocal folds and cells, or any combination thereof, said tissues which originate, for example and without limitation, in any of the following species: Baboon, Buffalo, Cat, Chicken, Cow, Dog, Goat, Guinea Pig, Hamster, Horse, Human, Monkey, Mouse, Pig, Quail, Rabbit, and the like.

In some embodiments, a plurality of cells comprises tissue culture cells, primary cells, reproductive cells, for example egg cells and/or sperm, a tissue, an organ or a portion thereof, or any combination thereof. In some embodiments, said tissue culture cells or primary cells comprise stem cells, adult cells, transdifferentiated cells, dedifferentiated cells, or differentiated cells, or any combination thereof. In some embodiments, a plurality of cells comprises human cells or animal cells.

One of ordinary skill in the art would appreciate that the term "in vivo" encompasses methods of use described herein carried out on a living organism in its natural state. For example, in one embodiment, contacting a plurality of cells in vivo comprises perfusion of an animal or a portion thereof. In another embodiment, contacting a plurality of cells in vivo comprises perfusion of an organ or a portion thereof, in an intact animal.

One of ordinary skill in the art would appreciate that the term "ex vivo" encompasses methods of use described herein carried out outside an organism. For example, in one embodiment, contacting a plurality of cells ex vivo may encompass exposes the cells in an artificial environment (sterile conditions) outside of the organism from where the cells originated, if they were primary cells, with minimum alternation of the natural conditions. For example, in one embodiment, contacting a plurality of cells ex vivo comprises perfusion of an organ or a portion thereof that has been removed from a subject. In another embodiment, contacting a plurality of cells ex vivo comprises perfusion of tissue or a portion thereof that has been removed from a subject. In some embodiments, the subject comprises an animal or a human.

One of ordinary skill in the art would appreciate that the term "in vitro" encompasses methods of use described herein that occur in an artificial environment. For example, in one embodiment, contacting a plurality of cells in vitro comprises mixing a composition disclosed herein with a plurality of cells in a test tube or reaction vessel, in cell culture, or in a Petri dish, or in another artificial environment known in the art, rather than within an organism (e.g., animal).

In one embodiment, bringing a plurality of cells in contact with a composition disclosed herein occurs in vivo, ex vivo, or in vitro.

The methods disclosed herein provide for contacting a plurality of cells, with a composition disclosed herein, thereby preserving and protecting the cells before damage results during the process of derivation and isolation or downstream manipulations, including cryopreservation. The contacting step may take place in vivo, for example, in some embodiments preceding removal of a plurality of cells from an organism, in another embodiment, the in vivo contacting step is systemic, delivering the inventive compositions to all cells and organs of an organism. In another embodiment, the in vivo contacting step is local, delivering the inventive compositions locally at the site of procurement of cells. The suitable methods of delivery will be immediately apparent to a skilled artisan, and comprise injection, intravenous perfusion, intra-coronary artery myocardium perfusion, intra-artery organ perfusion by catheter, coronary sinus perfusion, intracardiac perfusion or any method known in the art.

The application of this composition to gross tissues through the processes of non-thermal reversible electroporation, or perfusion bioreactor systems using three-dimensional cultures, for example, and to live organs for transplant is also possible. Since these compounds have great cellular penetrance capabilities, they are ideal for the protection of biological tissues and materials across a wide range of applications and species.

In some embodiments, the contacting step is carried out in vitro, for example on a tissue culture or on cells isolated from an organism. In some embodiments, the in vitro contacting step comprises immersing a plurality of cells into compositions disclosed herein immediately upon procurement. In another embodiment, the in vitro contacting step comprises immersing a plurality of cells into compositions a short time after procurement. In another embodiment, the in vitro contacting step comprises replacing the growth medium of an in vitro culture with a composition disclosed herein. In another embodiment, the in vitro contacting step comprises supplementing the growth medium of an in vitro culture with a composition disclosed herein. In another embodiment, the in vitro contacting step comprises rapid infusion with a composition disclosed herein, through non-thermal reversible electroporation. In another embodiment, the in vitro contacting step comprises incubating a plurality of cells immersed into a composition disclosed herein, in a perfusion bioreactor. In another embodiment, the in vitro contacting step comprises incubating a plurality of cells immersed in a composition disclosed herein in a 3-D culture. In another embodiment, bringing a plurality of cells in contact with a composition disclosed herein comprises contacting the plurality of cells in vivo or ex vivo, wherein said contacting comprises perfusion of an animal or a portion thereof, an organ or a portion thereof, or a tissue.

In some embodiments, a composition disclosed herein is introduced via transcardiac perfusion into animals or humans, thereby entering all organs and cells within seconds. Tissues and organs isolated from these sources are then kept in the composition throughout the subsequent steps until plating, transfer, or freezing. This includes cells dissociated during this process, which are kept in the solution until subsequent plating or freezing. In some embodiments, organs derived from subjects are processed with certain organ transplant procedures of which any solutions required are reformulated to contain the composition such that necrosis and necroptosis is avoided and cells within the tissue are protected.

In some embodiments, perfusion comprises cardiac perfusion. In some embodiments, bringing a plurality of cells into contact in vitro comprises immersing the plurality of cells in a composition disclosed herein, or supplementing a growth media of the plurality of cells with a composition disclosed herein, or perfusing the plurality of cells with a composition described herein via non-thermal reversible electroporation, or perfusing the plurality of cells with a composition disclosed herein in a bioreactor.

In some embodiments, bioreactors are used to expand and propagate a plurality of cells. In some embodiments, bioreactors may be used for cultivation of cells, in which conditions are suitable for high cell concentrations. In another embodiment, a bioreactor provides a closed system for expansion of cells. In another embodiment, multiple bioreactors are used in a series for cell expansion. In another embodiment, a bioreactor used in the methods disclosed herein is a single use bioreactor. In another embodiment, a bioreactor used is a multi-use bioreactor. In yet another embodiment, a bioreactor comprises a control unit for monitoring and controlling parameters of the process.

In some embodiments, a composition disclosed herein is infused rapidly into tissue derived from animals or humans through non-thermal reversible electroporation, or perfusion bioreactor systems using three-dimensional cultures, for example. Other tissue infusion mechanisms may also be used similarly. In other embodiments, the tissue may derive from in vitro sources, for which the composition can be infused in vitro upon replacement of growth media or other supporting solution.

In some embodiments, tissue derived from human subjects may be retrieved and perfused with a composition disclosed herein upon procurement. This may be accomplished through pre treatment with the composition locally at the site of procurement or in vitro immediately after tissue isolation. In some embodiments, the tissue may be procured and simultaneously placed into a container prefilled with the composition solution.

In some embodiments, the tissue derived from animals or humans is placed into a composition disclosed herein and processed to liberate cells that are to be subjected to cryopreservation, or the cells are to be used in vitro for cell culturing. Here the tissue and cells are continuously subjected to the composition and changes in solutions are accompanied by appropriate additions of composition to enable preservation and protection from necrosis and necroptosis.

The introduction of a composition disclosed herein via transcardiac perfusion of living animals, wherein for example, an animal includes a pregnant female adult animals, results in rapid preservation of all organs and cells, including penetration to embryonic tissues across the body axis including privileged organs such as the brain. Also, simple introduction in vitro to tissue or any plurality of cells described herein, permits rapid penetration and activation. This represents a surprising new method to deliver preservation of cellular metabolic states before cells start to die upon tissue or cell procurement techniques, a type of "metabolic suspension".

In some embodiments of methods disclosed herein, a plurality of cells may be subjected to a physical, chemical or thermodynamic manipulation after the step of contacting the plurality of cells with a composition disclosed herein. In some embodiments of methods disclosed herein, a plurality of cells may be subjected to a physical, chemical or thermodynamic manipulation concurrent with the step of contacting the plurality of cells with a composition disclosed herein. In some embodiments of methods disclosed herein, a plurality of cells may be subjected to a physical, chemical or thermodynamic manipulation prior to the step of contacting the plurality of cells with a composition disclosed herein.

In some embodiments, the additional processing step during methods disclosed herein comprises liberating individual cells from the plurality of cells derived from animals or humans, organs thereof, or tissues thereof. In another embodiment, the additional processing comprises proteolytic digestion of extracellular proteins. In another embodiment, the additional processing comprises cell sorting. In another embodiment, the additional processing comprises treating cells with various chemicals and signaling molecules, for example to induce or suppress cell growth or differentiation. In another embodiment, the additional processing comprises centrifugation and resuspension of cells, e.g. in order to concentrate them.

In some embodiments, all the intermediate manipulations are carried out while cells are immersed in a composition disclosed herein. In some embodiments, all the intermediate manipulations are carried out while cells are immersed in a growth medium supplemented with a composition disclosed herein.

In some embodiment, methods disclosed herein include a thermodynamic manipulation comprising heating or cooling a plurality of cells. In another embodiment, the cooling comprising cryopreservation or a freeze-thaw cycle, or a combination thereof. In another embodiment, the cooling comprising multiple freeze-thaw cycles.

In some embodiments, a step of cooling a composition described herein comprising a plurality of cells involves reducing the overall temperature of a plurality cells immersed into or perfused with the compositions disclosed herein. In one embodiment, the temperature is reduced to below freezing temperature, for example for long-term storage. In another embodiment, the temperature is reduced to a value close to freezing point for a short or medium term prior to subsequent use, e.g. transplantation, re-implantation, or additional manipulations of cells, such as separation of cells of a particular type from the plurality of cells.

In some embodiments, the plurality of cells is immersed into or perfused with a composition disclosed herein, wherein the composition comprising the cells is rapidly cooled. In another embodiment, a plurality of cells is immersed into or perfused with a composition disclosed herein is cooled gradually. In another embodiment, rapid cooling is carried out in order to prevent denaturation of proteins in the cells undergoing cooling. In another embodiment, gradual cooling is carried out in order to induce the state of metabolic suspension in the cells undergoing cooling.

In some embodiments, of methods disclosed herein, a composition is pre-cooled prior to contacting a plurality of cells with the composition. In some embodiments of methods disclosed herein, a composition is pre-warmed to match culturing temperatures prior to contacting a plurality of cells with the composition. In some embodiments of methods disclosed herein, a composition is cooled concurrent with contacting a plurality of cells with the composition.

In one embodiment, provided herein is a method for inducing a state of metabolic suspension in a plurality of cells, the method comprising the steps of (a) bringing a plurality of cells in contact with a composition disclosed herein. In another embodiment, a method for inducing a state of metabolic suspension in a plurality of cells comprises the steps of (a) bringing a plurality of cells in contact with a composition comprising a necroptosis inhibitor compound and a Bax channel inhibitor; and (b) optionally cooling the plurality of cells. In some embodiments, a state of metabolic suspension comprises reversible cessation of oxygen metabolism. In some embodiments, a state of metabolic suspension is induced during or following methods of cryopreservation and/or freeze-thaw cycles thereof described herein. In some embodiments, a state of metabolic suspension is induced during or following methods of treating, preventing, inhibiting, or reducing the incidence of cellular plasticity, or necroptosis or necrosis, in a plurality of cells as described herein.

One skilled in the art would appreciate that the term "metabolic suspension" may encompass a slowing and/or halting of metabolic biochemical pathways, including the halting of oxygen metabolism. In some embodiments, methods disclosed herein protect viability and preserve the identity of cells by inducing a state of metabolic suspension. For examples, in another embodiment methods disclosed herein induce a metabolic suspension in stem cells and adult cells that are reprogrammed, de-differentiated, or trans-differentiated into new cell types, wherein the identity of the reprogrammed, de-differentiated, or trans-differentiated cell is maintained. In some embodiments, methods disclosed herein inducing metabolic suspension preserve cellular metabolic states, thereby preventing cell death due to stress caused by tissue or cell procurement procedures. In some embodiments, methods disclosed herein inducing metabolic suspension, enhance cell viability. In some embodiments, methods disclosed herein using compositions disclosed herein prevent, inhibit, or reduce changes in the differentiation state of a plurality of cells brought into contact with a composition disclosed herein, wherein the identity of the cells are stabilized compared with an uncontacted cell population, or a population contacted with compositions known in the art. In another embodiment, methods disclosed herein result in a plurality of cells retaining their cellular identity. In another embodiment, cellular identity is retained during cooling of said cells. In another embodiment, cellular identity is retained during freezing of said cells. In another embodiment, cellular identity is retained during and following freeze-thaw cycles performed as part of cryopreservation of said cells. In another embodiment, cellular identity is retained during physical manipulation of said cells. In another embodiment, cellular identity is retained during storage of said cells.

In some embodiments, methods disclosed herein prevent, inhibit, or reduce necrosis or necroptic death of said plurality of cells during a method of cryopreservation or a freeze-thaw cycle thereof, compared with a control plurality of cells not contacted with a composition disclosed herein. In some embodiments, methods disclosed herein prevent, inhibit, or reduce necrosis or necroptic death of said plurality of cells during a method comprising a freeze-thaw cycle, compared with a control plurality of cells not contacted with a composition disclosed herein.

In some embodiments, a method disclosed herein protects a plurality of cells from physical damage during a cryopreservation step or a freeze-thaw cycle thereof. In another embodiment, physical damage due to cryopreservation of a freeze-thaw cycle thereof comprises cellular shrinkage and dehydration due to ice formation upon freezing. Rapid loss of intracellular water may occur as a result of initial extracellular ice crystal formation and ensuing osmotic strength increase. With this loss of water comes the concomitant loss of critical levels of cellular metabolites. For example, in another embodiment, ATP and NAD may be lost during this process of cryopreservation or a freeze-thaw cycle thereof. In another embodiment, cells are physically "poked" open transiently at the plasma membrane, temporarily exposing open holes where metabolites may be lost.

In some embodiments, a method disclosed herein protects the plurality of cells by inhibiting or reducing excess calcium release within cells, inhibiting or reducing excess ATP release from cells, inhibiting or reducing excess NAD release from cells, or by inhibiting activation of pathways that lead to necrosis and necroptosis, or any combination thereof. In some embodiments, a method disclosed herein protects a plurality of cells, for example an organ or portion thereof, or a tissue by inhibiting or reducing a lack of oxygenation, free radical generation, or ischemia, or any combination thereof. In another embodiment, a method disclosed herein protects the plurality of cells by inhibiting or reducing increased $Ca^{2+}$ concentration in cells, activation of PARP within cells leading to decreased NAD and ATP levels, or increased reactive oxygen species, or any combination thereof.

One of ordinary skill in the art would appreciate that term "physical damage" may encompass any disruption of physiological cell functions or cell death. Non-limiting examples for disruption of physiological cell functions include: oxidative stress (for example, lipid peroxidation, DNA and RNA oxidation and protein oxidation), non-specific glycation, protein misfolding, DNA mutation, loss of any cellular structure integrity, metabolic stress, thermodynamic stress, temperature fluctuation shock, ionizing and non-ionizing radiation damage and chemical stress (for example, exposure to acid or basic substances). Accordingly, the expression "protection from physical damage" in some embodiments encompasses either preventing or decreasing cell death, or preventing or decreasing the deterioration in cellular function, as compared to control cells not contacted with a composition disclosed herein.

In some embodiments, methods of cryopreservation enhance growth potential of said plurality of cells compared with an uncontacted plurality of cells or a plurality of cells contacted with known cryopreservation solutions. In another embodiment, the time frame for storage of cells is increased following cryopreservation using a composition disclosed herein. In another embodiment, methods of cryopreservation enhance growth potential of said plurality of cells, wherein the use of a composition disclosed herein provides superior post-thaw cellular viability, growth potential and differentiation characteristics across species and cell types, as compared with cells cryopreserved using compositions known in the art. In another embodiment, provided herein is a method for enhancing growth potential in a plurality of cells during isolation, manipulation, low temperature culturing, or cryopreservation and freeze-thaw cycles thereof, the method comprising the steps of (a), bringing a plurality of cells in contact with a composition comprising a necroptosis inhibitor compound and a Bax channel inhibitor; and (b) optionally cooling the plurality of cells.

In some embodiments, the methods described herein preserve health and viability of isolated cells or cells within tissues or organs, and thereby enhance medical potency and utility of cells in transplant, regenerative and reproductive medical applications, such as biobanking, and preservation of cells for in-vitro fertilization. Thus, in another embodiment, provided herein is a method for preservation of cells for in-vitro fertilization, the method comprising the steps of (a), bringing a plurality of cells in contact with a composition comprising a necroptosis inhibitor compound and a Bax channel inhibitor; and (b) optionally cooling the plurality of cells. In another embodiment, provided herein is a method for biobanking of personalized cellular medical samples, the method comprising the steps of (a), bringing a plurality of cells in contact with a composition comprising a necroptosis inhibitor compound and a Bax channel inhibitor; and (b) optionally cooling the plurality of cells. In another embodiment, provided herein is a method for preservation of cells for regenerative medicine and cosmetic surgery, the method comprising the steps of (a), bringing a plurality of cells in contact with a composition comprising a necroptosis inhibitor compound and a Bax channel inhibitor; and (b) optionally cooling the plurality of cells.

One of ordinary skill in the art would appreciate that the term "enhance growth potential" may encompass any measurable increase in the cell's mitotic cell division rate, as compared to control cells not treated with compositions disclosed herein.

In some embodiments, methods disclosed herein using a composition disclosed herein improve the viability or latent viability of cells compared with an uncontacted plurality of cells, or a plurality of cells contacted by compositions known in the art.

Major causes of cell damage during its lifetime are through the oxidative cellular respiration pathways, and the normal processes of energy production and maintenance. This is enhanced under a variety of cellular stressors and environmental conditions, during which the ability of cellular machinery to compensate for these changes is compromised. Stressors burden the machinery that protects from excessive oxidative damage to many cellular substrates, causing a feedback loop that rapidly escalates damage and leads to a vulnerable phase for cell viability.

One example of conditions leading to this vulnerability is temperature fluctuation shock, which occurs during the cryopreservation freeze-thaw process. In addition, the isolation of cells from tissue during dissection of animal organs, during biopsy, or isolation of stem cells for growth and differentiation in bioreactors for cell therapy purposes all cause damage in the process. This damage includes physical damage when removing cells from tissues and organs, chemical damage when introducing agents that facilitate this removal of cells, and environmental damage when cells are removed from their source of metabolic nourishment, including lack of sufficient oxygenation (ischemia) or changes in osmolality.

In some embodiments, methods of cryopreservation disclosed herein using a composition described herein, prevent oxidative damage to said plurality of cells compared with an uncontacted plurality of cells or a plurality of cells contacted with known cryopreservation solutions. In some embodiments, methods of cryopreservation disclosed herein using a composition described herein, prevent ischemia of a plurality of cells during said cryopreservation of freeze-thaw cycles thereof, compared with an uncontacted plurality of cells or a plurality of cells contacted with known cryopreservation solutions.

In some embodiments, methods disclosed herein for cryopreservation or for treating, preventing, inhibiting or reducing the incidence of cellular plasticity, or necroptosis or necrosis, in a plurality of cells, inhibits necrosis pathway signaling within the plurality of cells. In another embodiment, inhibition of the necrosis pathway may be at any level of the pathway.

In one embodiment, provided herein is a method of cryopreservation, wherein said method induces a state of metabolic suspension in a plurality of cells during cryopreservation and freeze-thaw cycles thereof, the method comprising the steps of (a), bringing a plurality of cells in contact with a composition comprising a necroptosis inhibitor compound and a Bax channel inhibitor; and (b) cooling the plurality of cells. In one embodiment, provided herein is a method for improving viability of a plurality of cells, the method comprising the steps of (a), bringing a plurality of cells in contact with a composition comprising a necroptosis inhibitor compound and a Bax channel inhibitor; and (b) optionally cooling the plurality of cells.

EXAMPLES

Tissue dissection and cell manipulation were studied in several cell types. Comparative levels of reactive oxygen species (ROS) were measured as a function of Nox1 levels; comparative levels of apoptosis were measured as a function of CASP3 levels; comparative levels of necrosis were measured as a function of staining with PI and/or Annexin V in several cell types.

Example 1

A Cryopreservation Solution Reduced Levels of Reactive Oxygen Species (ROS), Apoptosis, and Necrosis Resulting from Tissue Dissection and Cell Manipulation.

Figure 1A:
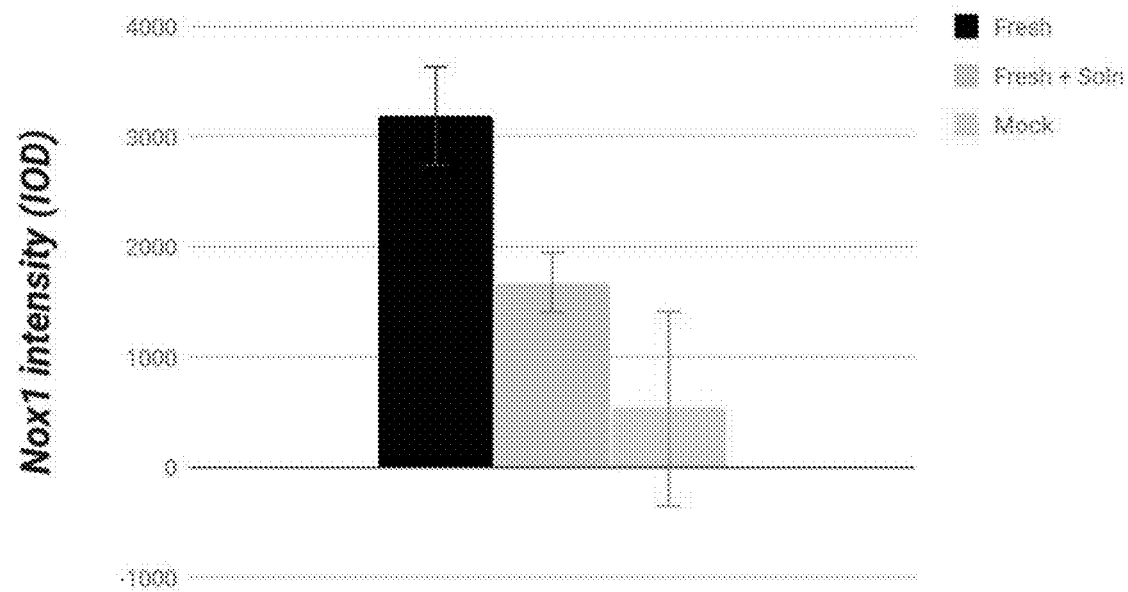
FIGS. 1A-C. Tissue dissection and cell manipulation produces reactive oxygen species (ROS) (detection of Nox1), apoptosis (detection of CASP3), necrosis (detection of staining with PI and/or Annexin V) in several cell types.
Figure 1B:
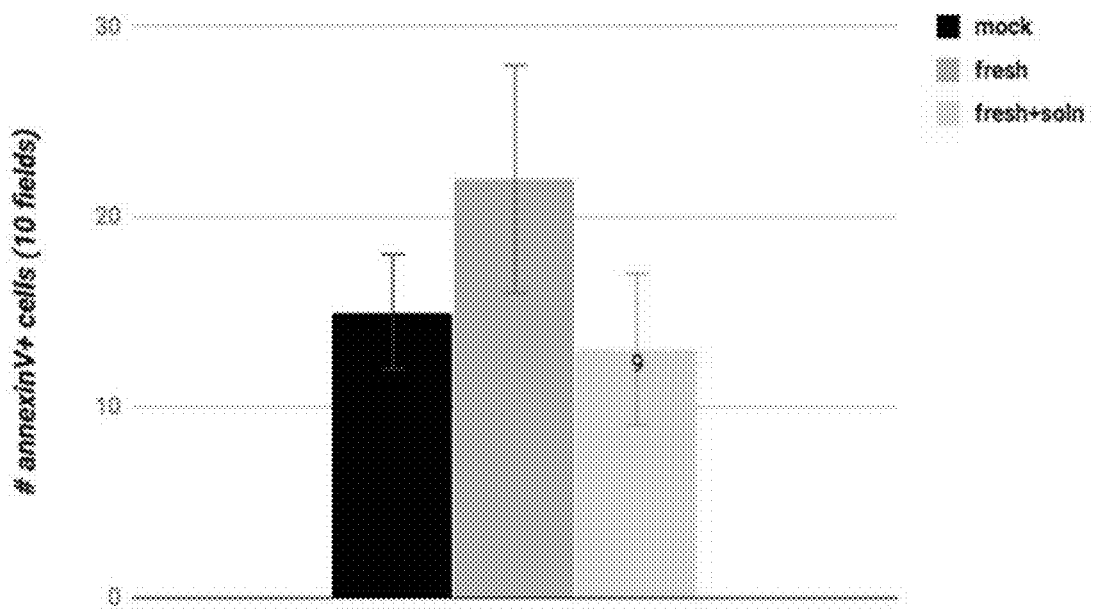
Figure 1C:
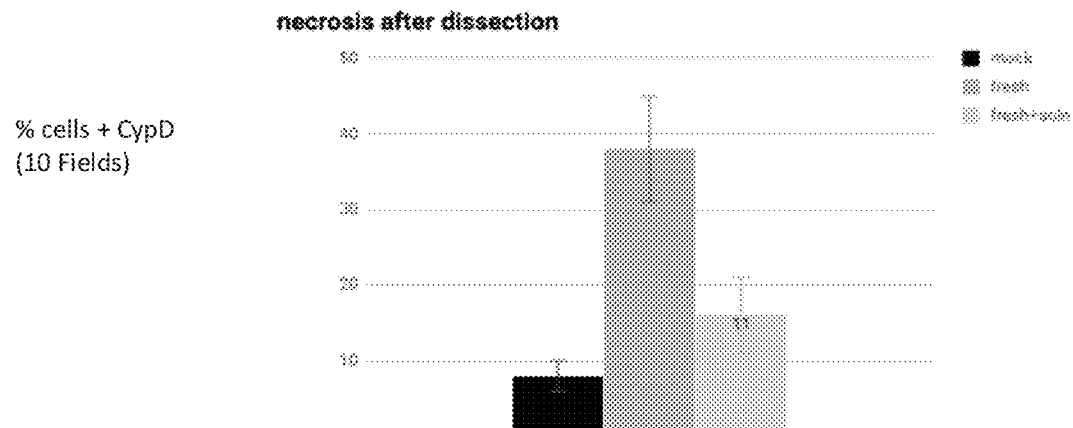

Tissue dissection and cell manipulation of mouse cortical neuron tissue was studied in the presence and absence of a cryopreservation solution (Sola, soln). (For FIGS. 1A-1C Soln/soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 μM adenosine triphosphate (ATP), 0.01 μM cyclosporin A, and 0.1 Kuntz Unit manganese superoxide dismutase.) Tissue dissection and cell manipulation of freshly dissected tissue (Fresh) produced reactive oxygen species (ROS) (FIG. 1A), whereas little ROS was observed in tissue without dissection (mock). The freshly dissected tissue (Fresh) yielded several-fold increase in ROS generation, while inclusion of the cryopreservation solution (Soln) diminished ROS levels in freshly dissected tissue (Fresh+Soln) (FIG. 1A), FIG. 1B shows that apoptosis was enhanced after dissection (fresh) compared to unmanipulated tissue (mock), although to a lesser extent than ROS generation (FIG. 1A) or necrosis (FIG. 1C), while inclusion of the cryopreservation solution (+soln) decreased this hack to baseline levels. FIG. 1C shows that necrosis was enhanced after tissue dissection and cell manipulation (fresh) compared to no tissue manipulation (mock), an effect that was almost completely removed by inclusion of the cryopreservation solution (+soln).

Example 2

A Cryopreservation Solution Reduced Levels of Reactive Oxygen Species (ROS), Apoptosis, and Necrosis Resulting from Cellular Freezing with Subsequent Thawing.

Figure 2A:
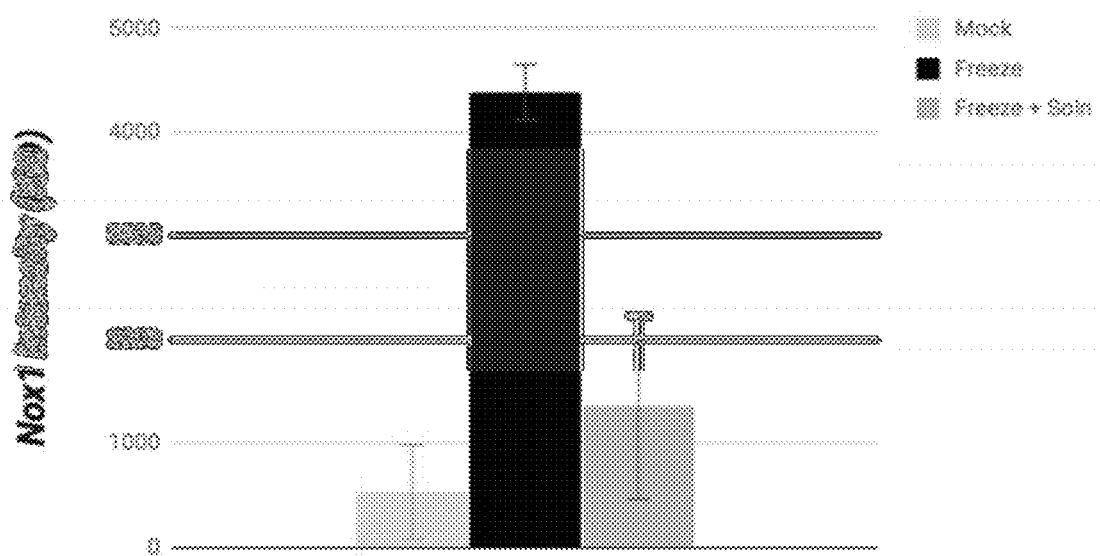
FIGS. 2A-2C. Cellular freeze/thaw generates significant increases in ROS, apoptosis, and necrosis markers in a number of cell types over time.
Figure 2B:
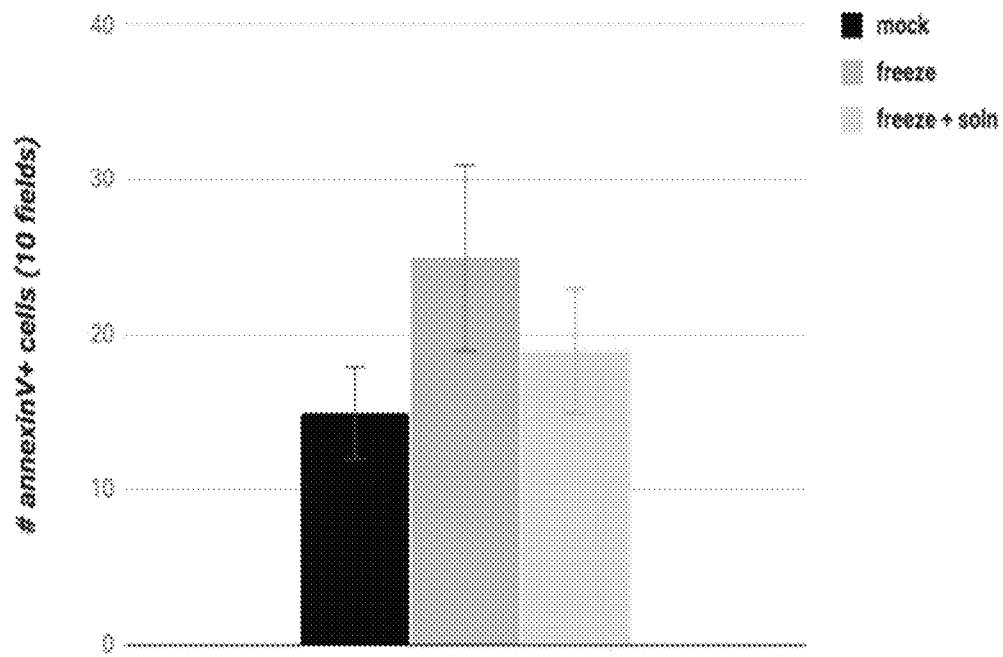
Figure 2C:
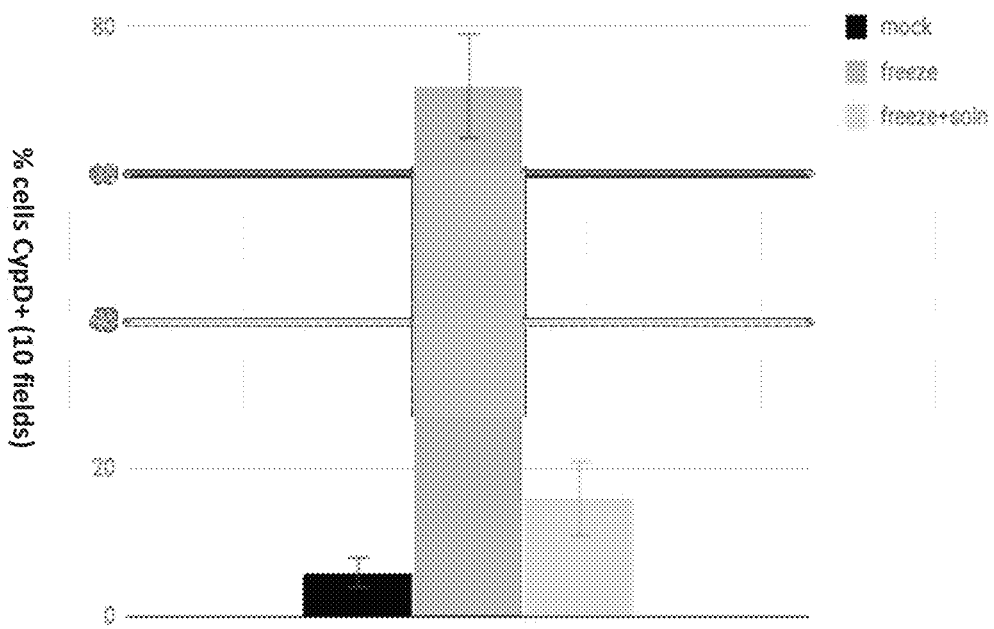

Cellular freeze/thaw of neurons was studied with respect to levels of ROS, apoptosis, and necrosis markers in a number of cell types over time. (For FIGS. 2A-2C Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 μM adenosine triphosphate (ATP), 0.01 μM cyclosporin A, and 0.1 Kuntz Unit manganese superoxide dismutase.) (CypD-Cyclophilin D) Freeze/thaw of neurons produced ROS (detection of Nox1) (Freeze) compared to tissue before freezing (Mock), an effect which was almost completely abolished by inclusion of the cryopreservation solution (+Soln) (FIG. 2A). Apoptosis was slightly enhanced after freeze/thaw (freeze) compared to tissue before freezing (mock), an effect that was decreased by inclusion of the cryopreservation solution during the freezing process (+soln) (FIG. 2B). Necrosis was greatly enhanced after cell freeze/thaw (freeze) compared to tissue before freezing (mock), an effect that was almost eliminated by inclusion of the cryopreservation solution (+soln) (FIG. 2C).

Example 3

Figure 3:
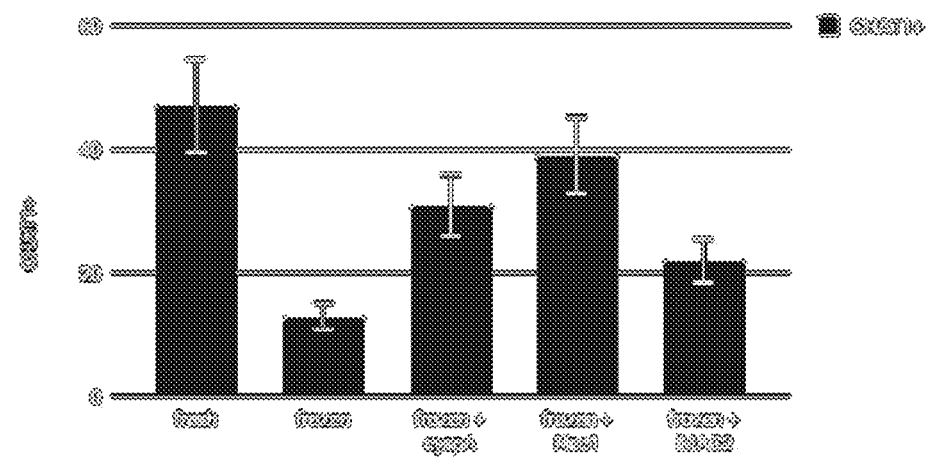
FIG. 3 shows that stem cells (motor neuron precursors) cultured and expressing CHAT1 (fresh) and then frozen in solutions comprising 0.01 µM cyspA, (cyclosporine A), or 20 nM Nec1, or 5 nM iMAC2 maintained CHAT1 as compared with stem cells frozen in the absence of these compounds, which showed very low levels of CHAT1+ cells after freezing (frozen). As shown here, each of cyspA, Nec1, and IMAC2 provided cryoprotection to stem cells upon freezing, maintaining cellular characteristics.

Motor Neuron Stem Cells Frozen in a Cryoprotectant Solution Maintained Motor Neuron Identity Cellular freeze/thaw cycle causes stem cells to lose their identity, as measured by the level of CHAT1 in motor neurons. Stem cells (motor neuron precursors), which were cultured and expressed CHAT1 (fresh) and then frozen in solutions comprising 0.01 µM cyspA (cyclosporine A), or 20 nM Nec1, or 5 nM iMAC2, maintained CHAT1 levels as compared with stem cells frozen in the absence of these compounds, which showed very low levels of CHAT1+ cells after freezing (frozen) (FIG. 3). As shown here (FIG. 3), each of cyspA, Nec1, and IMAC2 provided cryoprotection to stem cells upon freezing, maintaining cellular characteristics. Cryoprotectants in solution used to freeze the cells, maintained motor neuron identity, as measure by the level of CHAT1.

Example 4

Figure 4A:
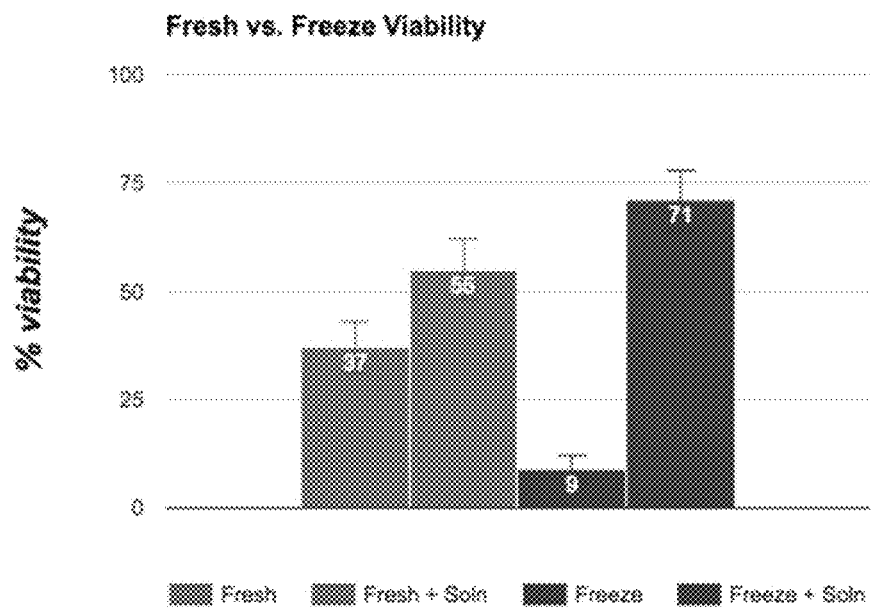
FIGS. 4A-4B. Fresh versus frozen cell viability was analyzed by maintenance of dissected cells (hippocampal neurons) in one embodiment of a cryopreservation solution.
Figure 4B:
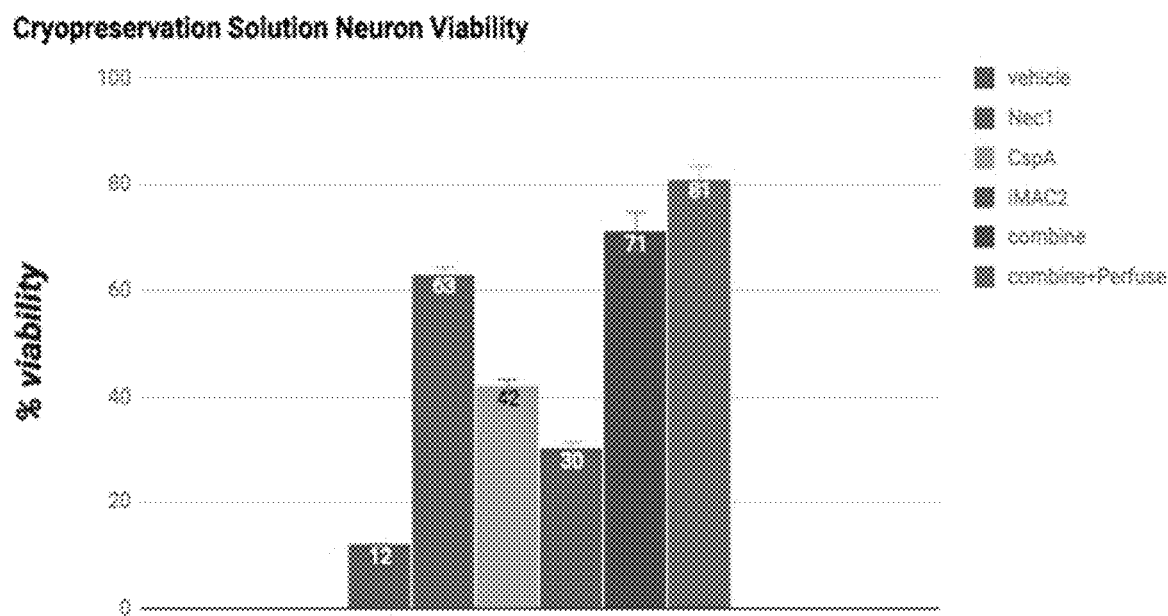

A Cryopreservation Solution Maintained Cell Viability of Frozen Dissected Hippocampal Neurons Fresh versus frozen cell viability was analyzed by maintenance of dissected cells (hippocampal neurons) in one embodiment of a cryopreservation solution. The cell viability for neurons was measured after 7 days in vitro. Vehicle had no cryopreservation solution addition, while necrostatin1 (Nec1), cyclosporine A (CspA), iMAC2 (iMAC2), or the combination of those 3 reagents (combine), were introduced to cells before the freeze/thaw process. In one embodiment (combine+Perfuse), the 3-reagent cryopreservation solution was perfused into a living pregnant mouse briefly just minutes before the pups were isolated from the dam, and then the hippocampal neurons isolated from the E18 (embryonic day 18) pups. The concentrations of the different components are those concentrations used in FIG. 4A. (Soln: 20 nM 5-((7-Chloro-1H-ndol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.) Key FIG. 4A and throughout the figures: Fresh represents Freshly dissected cells; Fresh+Soln represents Freshly dissected cells in composition solution; Freeze represents Frozen/Thawed cells; and Freeze+Soln represents Frozen/Thawed cells in composition solution. Cryopreservation solutions disclosed herein, by itself was able to increase the percent viability of freshly dissected cells as well as cells that had been frozen in an embodiment of a cryopreservation solution, and then thawed (FIG. 4A). Metabolic suspension of cells (hippocampal neuron) enhanced cell viability, wherein the percent viability provided by different components of cryopreservation solutions is shown (FIG. 4B).

Example 5

Figure 5:
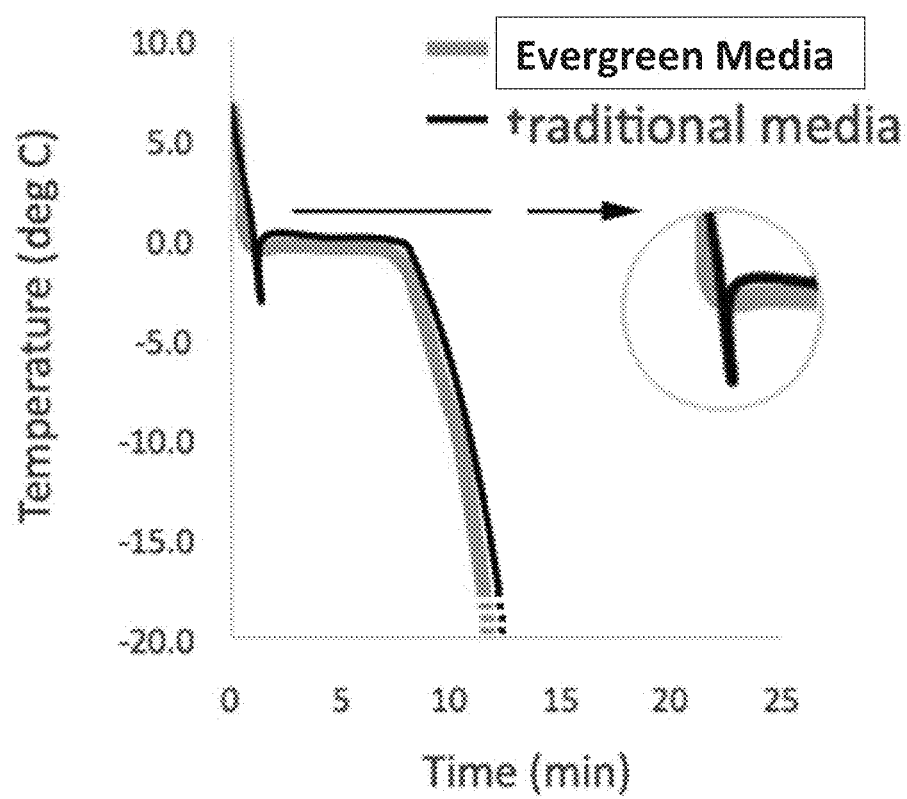
FIG. 5. Freezing process used herein, avoids supercooling effects that damages cells.

Use of a Cryopreservation Solution Avoids Supercooling Effects that Damage Cells A comparison study was made of the change in temperature over time during freezing in either an embodiment of a cryopreservation solution, disclosed herein (EVEKCREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase) versus a traditional media (FIG. 5). There was a notable absence of the early downward spike in temperature that occurred in traditional media (FIG. 5, inset). Therefore, these results demonstrated that the freezing process used herein avoids supercooling effects that damages cells.

Example 6

A Cryopreservation Solution Maintained Cell Viability of Cortical Neuron Cells and Adipose Stem Cells Over Time Viability and growth rates for cortical neurons and for fat (adipose tissue) stem cells, both fresh and frozen, were observed over time with respect to a cryopreservation solution. (For FIGS. 6A-6D, Soln: 20 nM 5-((7-Chloro-1H-indol-3-yl)methyl)-3-methyl-2,4-imidazolidinedione). 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

Figure 6A:
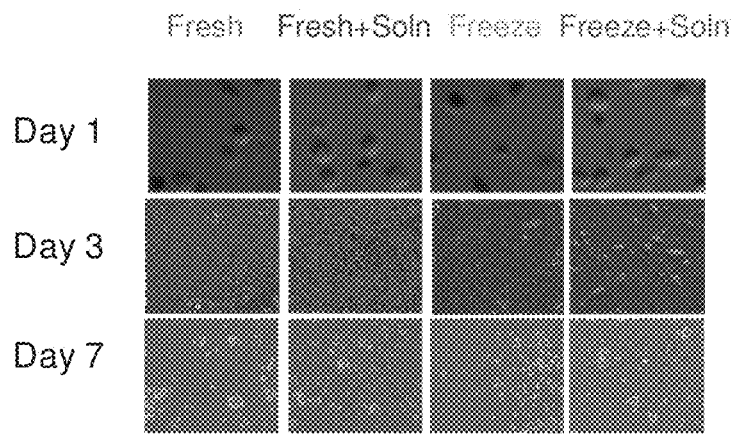
FIGS. 6A-D. Viability and Growth rates: Fresh vs. Frozen Cell Viability Time Course: neurons and fat (adipose tissue) stem cells.
Figure 6B:
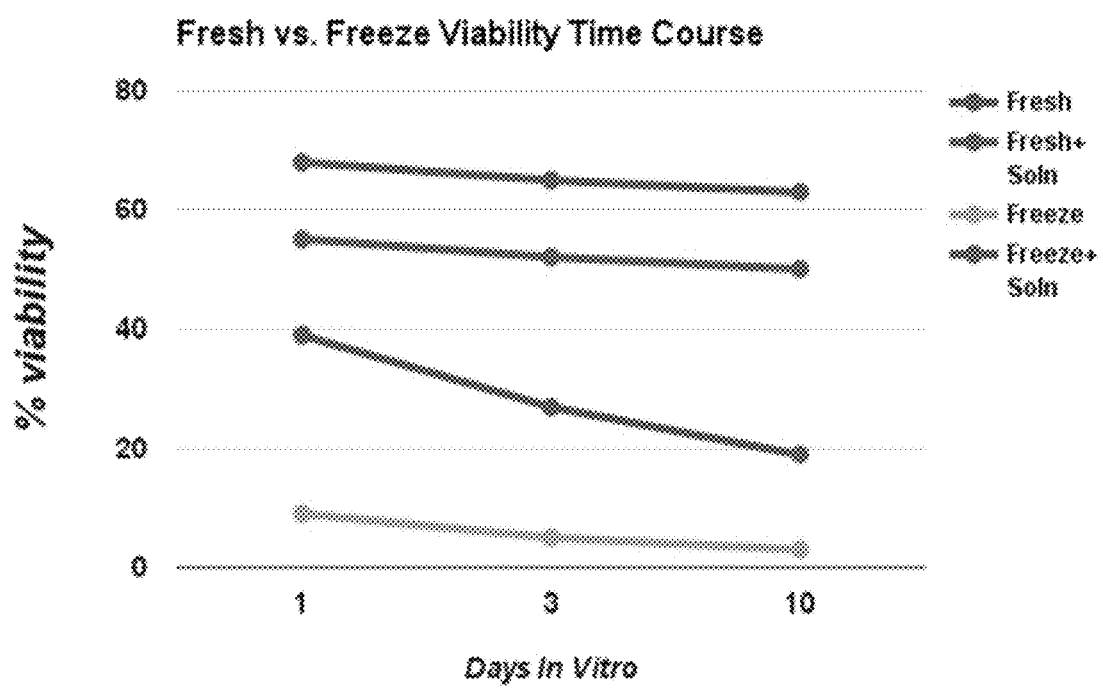

Cortical neuron cell viability was maintained when freshly dissected cells were suspended in an embodiment of a cryopreservation solution (fresh+Soln) disclosed herein, or dissection in and then frozen in an embodiment of a cryopreservation solution disclosed herein (freeze+Soln) (FIG. 6A). FIG. 6B shows the time course of percent neuron viability over time (days) after plating cells subjected to these freezing and non-freezing conditions. The inclusion of cryopreservation solution was compared to the same cells exposed to 10% DMSO before freezing (freeze) or to cells that were freshly dissected without any freezing cryoprotectant (fresh).

Figure 6C:
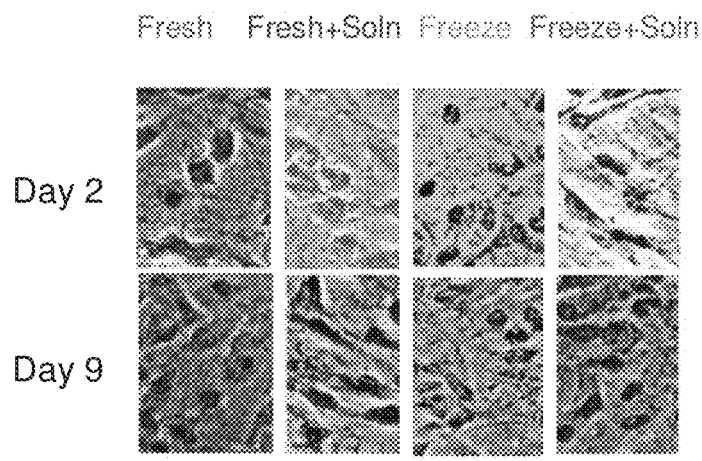
Figure 6D:
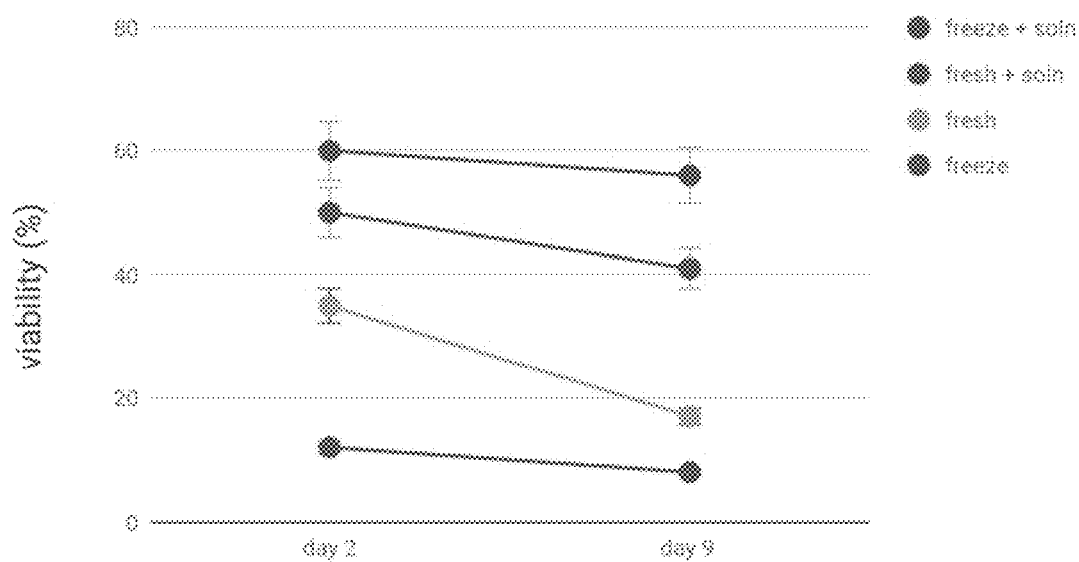

Similarly, fat (adipose tissue-derived) stem cell viability was maintained when freshly dissected cells were suspended in an embodiment of a cryopreservation solution (fresh+Soln) disclosed herein, or dissection in and then frozen in an embodiment of a cryopreservation solution disclosed herein (freeze+Soln) (FIG. 6C). FIG. 6D shows the time course of percent fat stem cell viability over time ((days) after plating cells subjected to these freezing and non-freezing conditions. The inclusion of cryopreservation solution was compared to the same cells exposed to 10% DMSO before freezing (freeze) or to cells that were freshly dissected without any freezing cryoprotectant (fresh).

Example 7

Figure 7A:
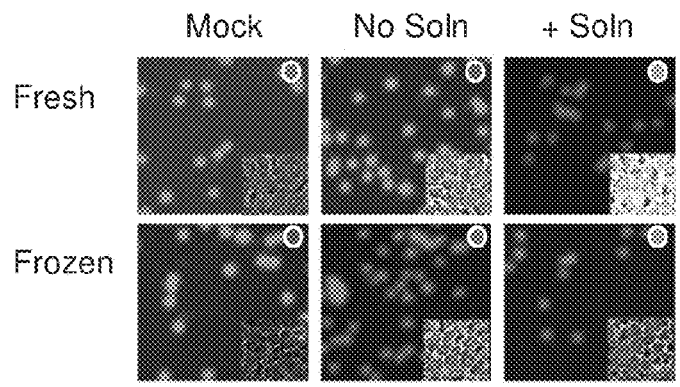
FIGS. 7A-B. Apoptosis after dissection and freeze/thaw with cryopreservation solution.
Figure 7B:
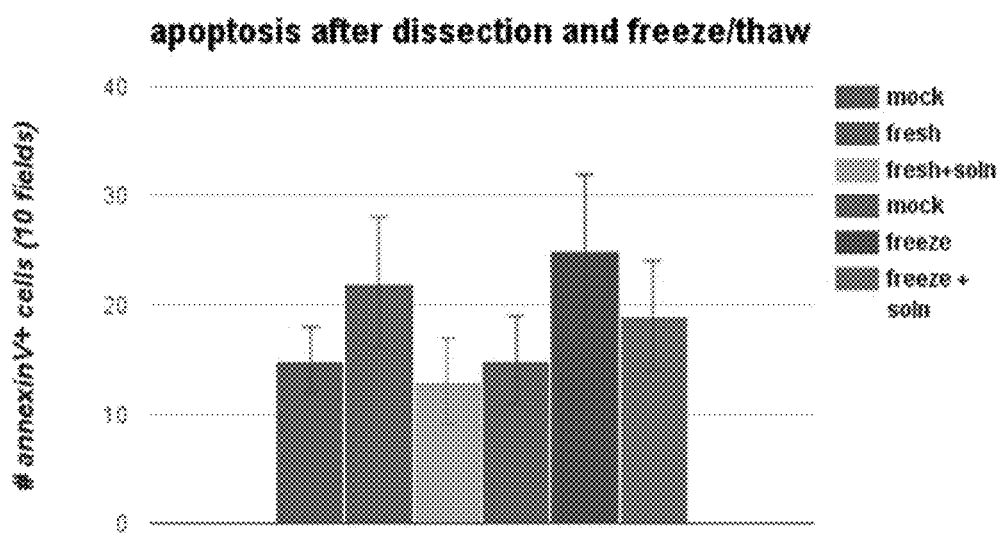

A Cryopreservation Solution Reduced the Number of Apoptotic Cells after Dissection and Freeze/Thaw Apoptosis of primary liver hepatocytes after dissection and freeze/thaw, with and without cryopreservation solution, was studied. (For FIGS. 7A-7B, Soln: 20 nM 5-((7-Chloro-1-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.) FIG. 7A shows a comparison of the effects of cryoprotectant on early apoptotic cells (primary liver hepatocytes) from fresh and frozen cells suspended in an embodiment of a cryopreservation solution disclosed herein, compared with cell suspended in an absence of such a solution (mock). For cells frozen that were not treated with cryopreservation solution (mock), they were suspended in 10% DMSO before freezing. Caspase3 (green) labels cells in an early apoptotic state in culture. FIG. 7B shows the number of apoptotic cells, as defined by annexin V labeling, in fresh or frozen and thawed cells suspended in an embodiment of a cryopreservation solution disclosed herein or in the absence of such a solution (mock). The addition of the cryopreservation solution reduced the number of apoptotic cells.

Example 8

A Cryopreservation Solution Reduced the Number of Necrotic Cells after Dissection and Freeze/Thaw Necrosis after dissection and freeze/thaw of cortical neuron cells suspended in the presence or absence of an embodiment of a cryopreservation solution, disclosed herein, was studied. (For FIGS. 8A-8B, Soln: 20 nM 5-((7-Chloro-1H-indol-3-yl)methyl)-3-methyl-2,4-imidazolidinedione), 5 nM. 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

Figure 8A:
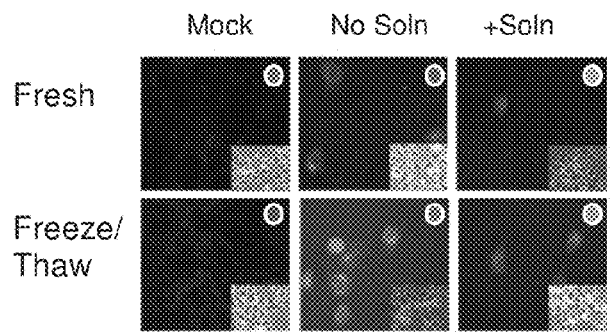
FIGS. 8A-8B. Necrosis after dissection and freeze/thaw of cortical neuron cells suspended in an embodiment of a cryopreservation solution disclosed herein.
Figure 8B:
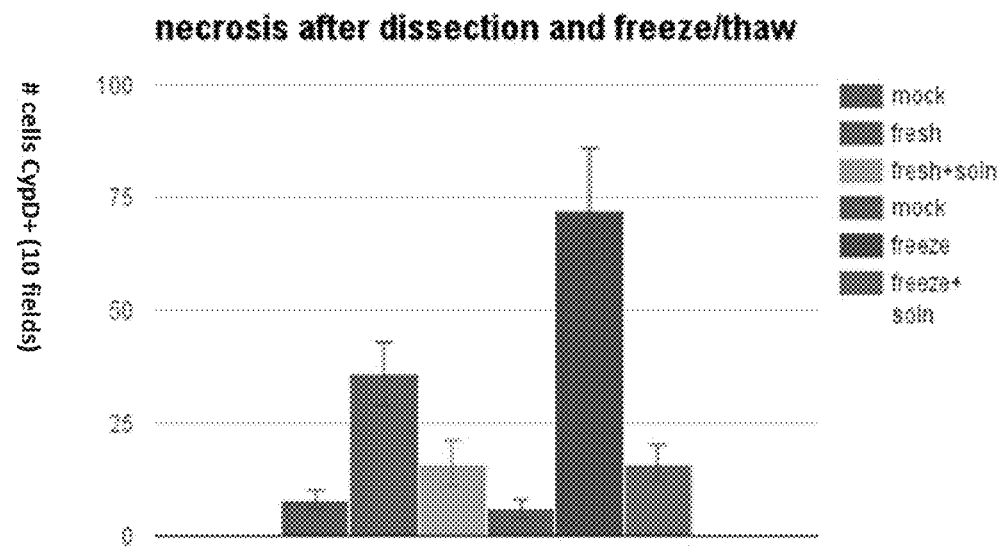

FIG. 8A shows a comparison of the presence of necrotic cells from solutions of fresh and frozen cells suspended in an embodiment of a cryopreservation solution disclosed herein, compared with cell suspended in an absence of such a solution. Anti-cyclophilin antibody labels cells in an early apoptotic state in culture. FIG. 8B shows the percent of necrotic cells after dissection performed in an embodiment of a cryopreservation solution, or the absence of such a solution. The addition of the cryopreservation solution reduced the number of necrotic cells.

Example 9

A Cryopreservation Solution Reduced the Generation of Reactive Oxygen Species (ROS) after Dissection and Freeze/Thaw, as Compared with DMSO, a Conventional Cryoprotectant.

Generation of Reactive Oxygen Species (ROS) (Nox1 as marker) in cortical neuron tissue after dissection and freeze/thaw, with respect to a cryopreservation solution (Soln) of the present invention vs. a conventional cryoprotectant (DMSO), was studied. (For FIGS. 9A-9B, Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosportin A, and 0.1 Kuntz. Unit manganese superoxide dismutase.)

Figure 9A:
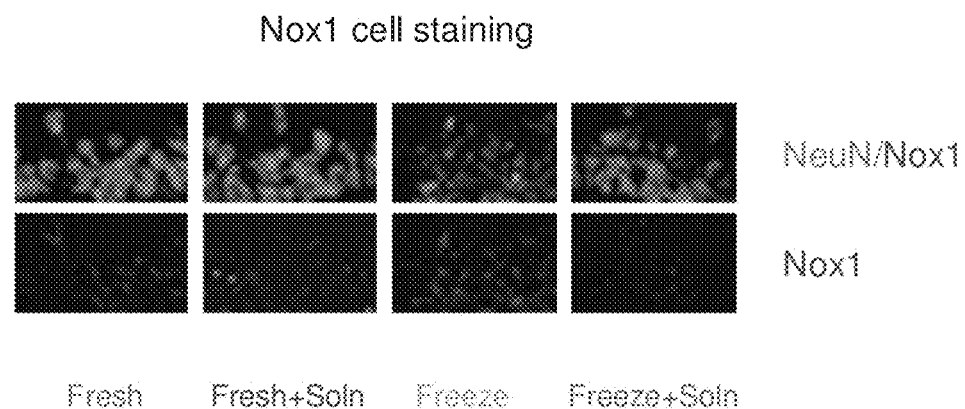
FIGS. 9A-9B. Reactive Oxygen Species (ROS) (Nox1 as marker) generation after cortical neuron tissue dissection and freeze/thaw.
Figure 9B:
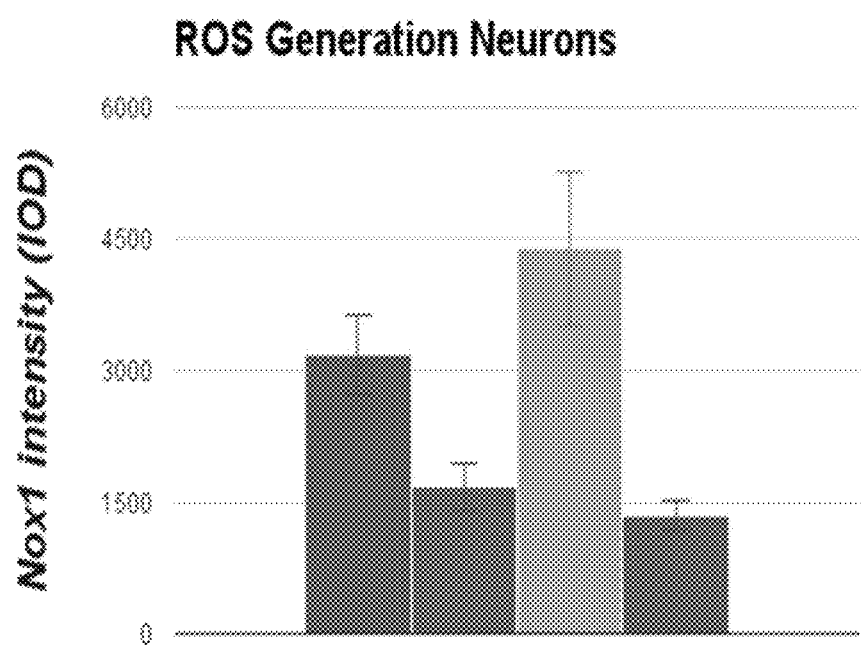

FIG. 9A shows Nox1 staining in fresh (dissected in saline only, and not frozen) neurons, fresh neurons dissected in cryopreservation solution (Fresh+Soln), neurons frozen while suspended in an embodiment of a cryopreservation solution disclosed herein, then thawed (Freeze+Soln) or in the presence of a conventional cryoprotectant (10% DMSO, dimethyl sulfoxide) (Freeze). Fresh or thawed neurons were plated and allowed to adhere before fixation and labeling for 4 hours. NADPH Oxidase (Nox1) labels ROS in cells. NeuN stains for cortical neurons (not glia). FIG. 9B shows ROS generation (Nox1 intensity) in freshly dissected cortical neuron tissue alone (fresh, blue bar), fresh cortical neuronal tissue dissected in the suspension of an embodiment of a cryopreservation solution disclosed herein (fresh+Soln, red bar), frozen cells suspended in an embodiment of a cryopreservation solution disclosed herein (freeze+soln, yellow bar) then thawed, or cells frozen and then thawed in the presence of 10% DMSO (green bar). The addition of the cryopreservation solution of the present invention (Soln) reduced the generation of ROS with respect to DMSO, a conventional cryoprotectant.

Example 10

A Cryopreservation Solution Preserved Neuronal Lineage of Motor Neuron Markers Significantly More than DMSO, a Conventional Cryoprotectant.

Figure 10A:
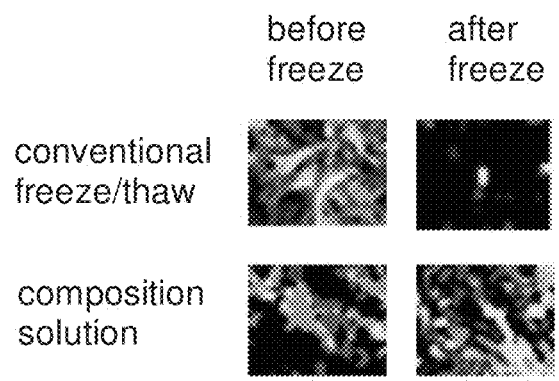
FIGS. 10A-B. Neuronal lineage of motor neuron markers are preserved significantly above that using conventional cryoprotectants (10% DMSO) compared to the composition solution.
Figure 10B:
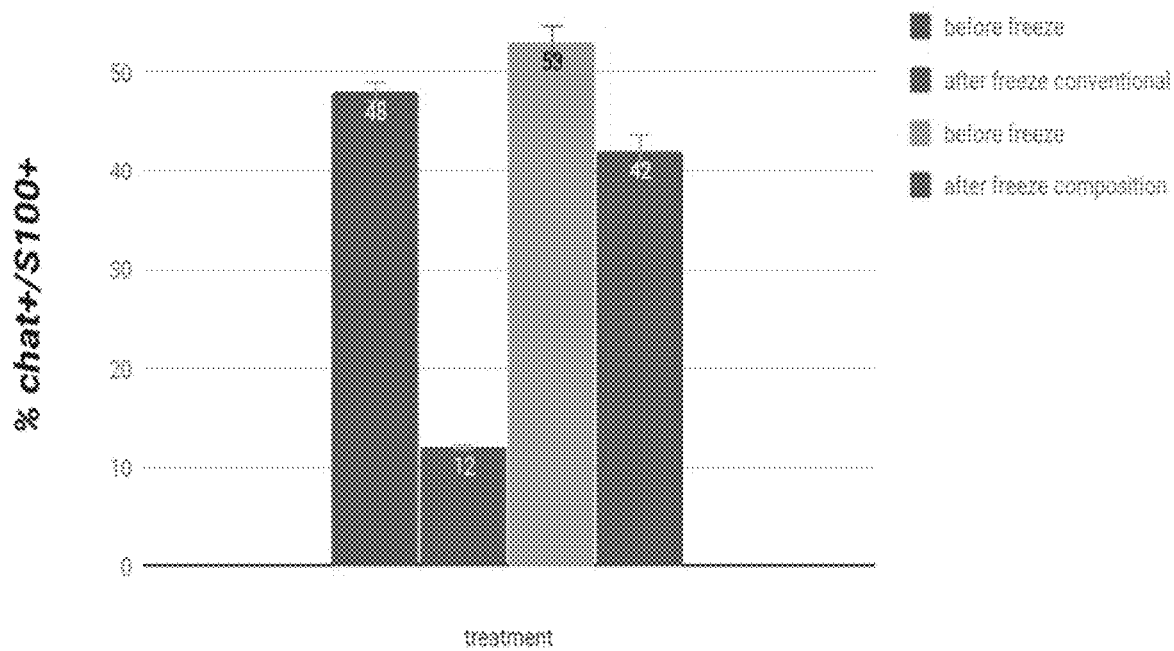

Preservation of the neuronal lineage of motor neuron markers (MN stem cell identity) was studied as a comparison of a cryopreservation solution of the present invention versus DMSO, a conventional cryoprotectant. (For FIGS. 10A-10B, Soln: 20 nM 5-((7-Chloro-1H-indol-3-yl) methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.) FIG. 10A shows the micrographs of neurons before or after freezing, in the presence or absence (10% DMSO only) of a cryopreservation solution disclosed herein. FIG. 10B shows motor neuron cell identity (as measure by the presence of CHAT1-positive, S100-positive immunofluorescence signal) in cells before and after freezing in conventional cryopreservation solutions (10% DMSO), and an embodiment of a cryopreservation solution disclosed herein ("after freeze composition"). MN stem cell identity was preserved after using the composition solution to a greater degree than after using DMSO, a conventional cryopreservation solution. Neuronal lineage of motor neuron markers were preserved significantly above that using conventional cryoprotectants (10% DMSO) compared to the composition solution.

Example 11

A Cryopreservation Solution Preserved Liver Cell Activity after Freeze/Thaw

The effect of a cryopreservation solution on liver cell activity after freeze/thaw, as compared with fresh samples, was studied. (For FIGS. 11A-11B, Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

Figure 11A:
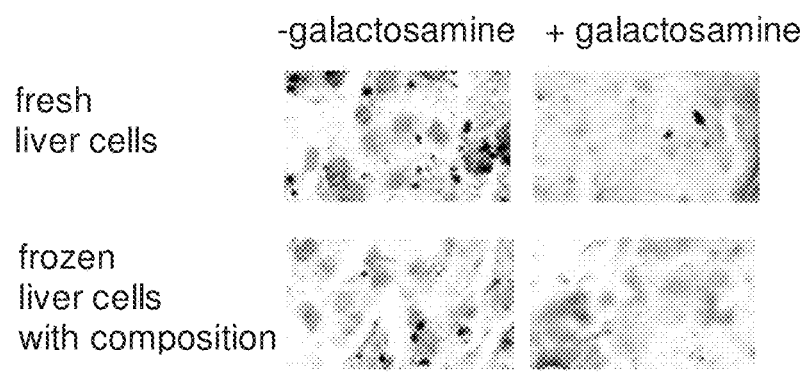
FIGS. 11A-11B. Primary mouse liver cells (hepatocytes) show similar physiological characteristics after freeze/thaw in the presence of composition solution as they do compared to freshly dissected tissue.
Figure 11B:
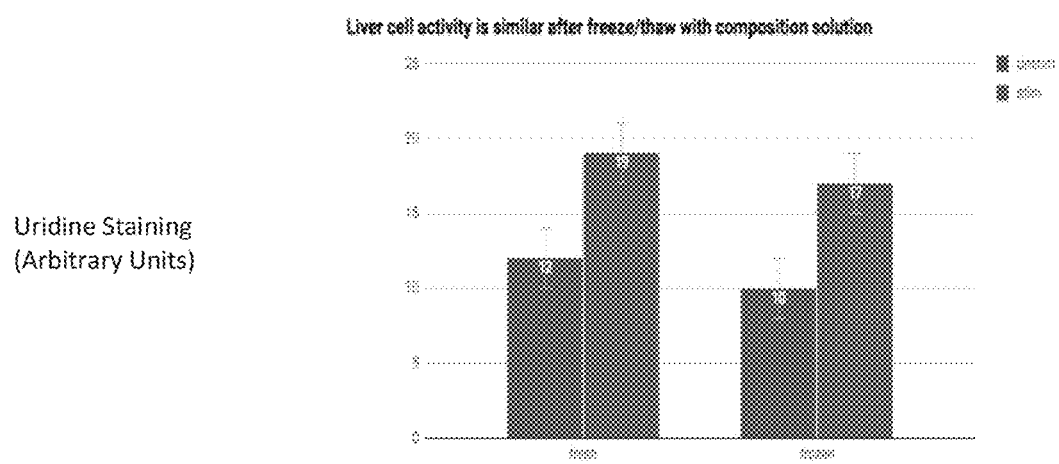

FIG. 11A shows a comparison of fresh and frozen liver cells (blue stain), incubated in the presence or absence (fresh, not frozen) of a cryopreservation solution disclosed herein, and either not (-galactosamine) or stimulated with galactosamine briefly before fixation and staining for anti-body-conjugated uridine (red stain), as a general measure of galactosamine-induced transcription. FIG. 11B shows a comparison of liver cell transcriptional activity in fresh and frozen cells suspended in an embodiment of a cryopreservation solution disclosed herein, wherein the liver cell activity is similar after freeze/thaw when cells are maintained in the presence of a cryopreservation solution disclosed herein. Bars measure anti-body-conjugated uridine staining (arbitrary units). Primary mouse liver cells (hepatocytes) show similar physiological characteristics after freeze/thaw in the presence of composition solution as they do compared to freshly dissected tissue.

Example 12

Figure 12:
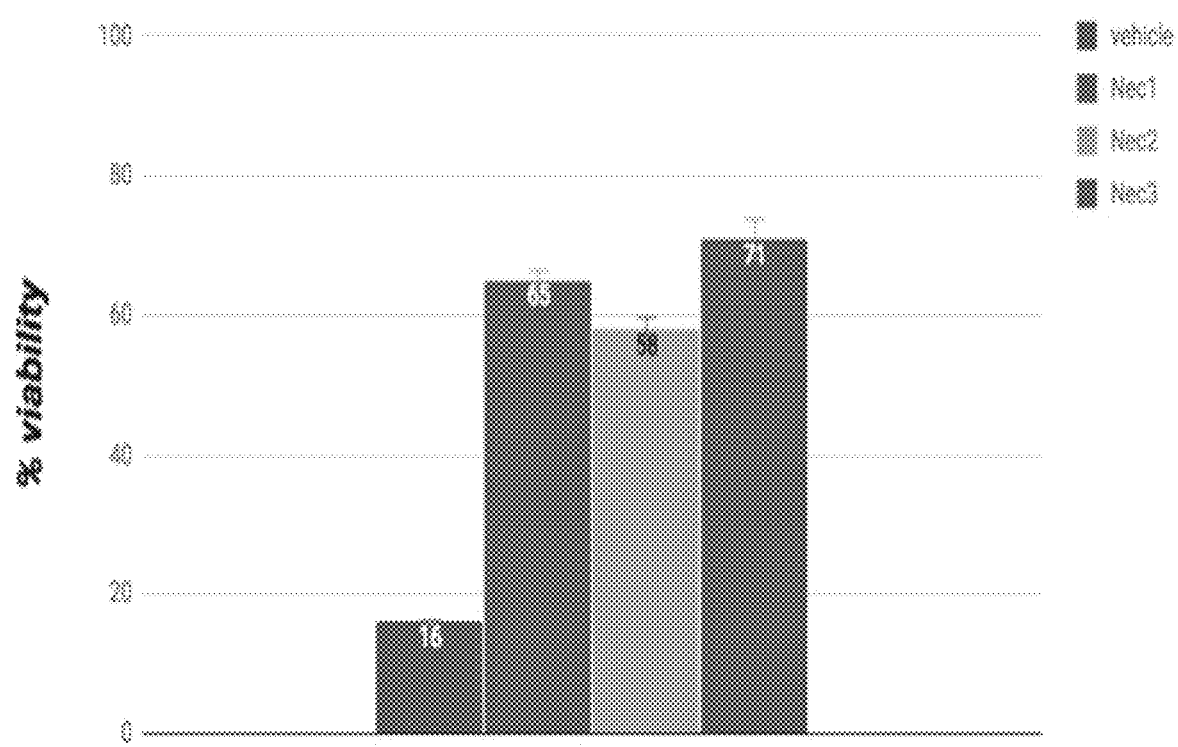
FIG. 12. Several analogs of necrostatins work similarly in their cryoprotective effect after freeze/thaw.

Comparison of Several Analogs of Necrostatins with Respect to Cryoprotective Effects Several analogs of necrostatins were studied and found to work similarly in their cryoprotective effect after freeze/thaw. FIG. 12 shows the effects of cryopreservation solutions comprising different necrostatins, wherein the presence of necrostatins (Nec1 (red bar), Nec2 (yellow bar), Nec3 (green bar) significantly enhanced percent viability of primary mouse cortical neuron cells compared to control cells (vehicle, blue bar) cryopreserved with conventional cryoprotectant (10% DMSO). The concentration of the different necrostatins is 20 nM, and the other components of the "soln" remain the same, that is: 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.

Example 13

A Cryopreservation Solution Inhibited Necroptotic Markers in Liver Cells

Expression of necroptotic markers in primary mouse liver cells (hepatocytes) was studied before and after freezing either in a cryopreservation solution of the present invention or in the convention cryopreservation solution DMSO. (Cryopreservation solution used herein was: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase.)

Figure 13A:
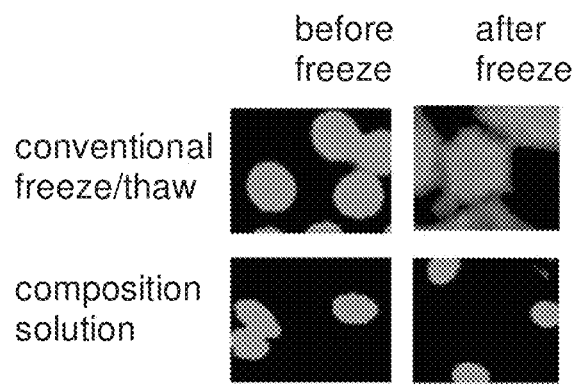
FIGS. 13A-13B. Necrostatic pathways are halted by the composition solution.
Figure 13B:
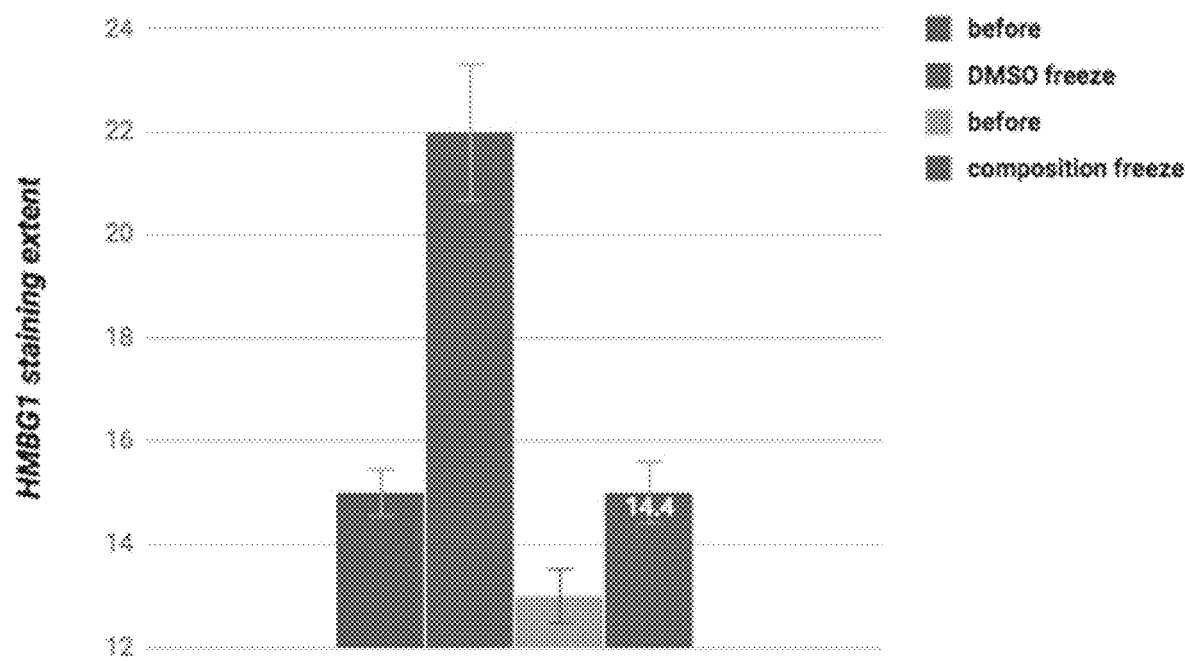

FIG. 13A shows images of primary mouse liver cells (hepatocytes) before and after freezing in conventional cryopreservation solution (10% DMSO) and in an embodiment of a cryopreservation solution disclosed herein ("composition freeze"). The cells here are staining with an antibody that recognizes HMBG1 (green) as a marker for necroptosis. FIG. 13B shows that necroptotic markers were significantly inhibited in a cell suspension in an embodiment of a cryopreservation solution disclosed herein, compared with 10% DMSO ("DMSO freeze").

Example 14

TNF-Alpha Production in Necroptosis-Induced THP-1 Cells was Significantly Diminished with Use of a Cryopreservation Solution.

NE-alpha production in necroptosis-induced THP-1 cells was studied with respect to a cryopreservation solution (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™). Briefly, necrotic cell lysates were first generated and used in the assays for THP-1 cell cytokine production. Necrotic cell lysates were generated by taking THP-1 cells and culturing on 60 mm dishes in complete medium (RPMI 1640, supplemented with 2 mM glutamine, 10% fetal bovine serum, 100 U per mL penicillin, 100 µg/mL streptomycin) at 1-million cells per ml, and stimulating with 0.5 µg/ml of LPS. After ~12 h, the cells were collected, then washed briefly with PBS (2 times with 10× volume), then resuspended in complete medium at 1-million cells per mL. These cells were then used for necrosis induction by repeated (5-6 cycles) freezing with liquid nitrogen and thawing to 37° C. Lysates were made from these by centrifugation at 15K R.P.M. (24K×g) for 20 minutes at 4° C., and then added to freshly cultured THP-1 cells at a 50% volume/volume ratio with fresh medium. To this medium, LPS at 0.5 µg/mL was also added for maximum cytokine production. TNF-alpha and IL-6 protein concentrations were measured in the cultured supernatant using an ELBA kit (R&D Systems, Minneapolis, MN) following the manufacturers protocol. Each sample was assayed in duplicate, with standard known cytokine protein measurements as references. Data are mean of 3 independent experiments+standard error of the mean (S.E.M.). p values were calculated using the Students T-test.

Figure 14:
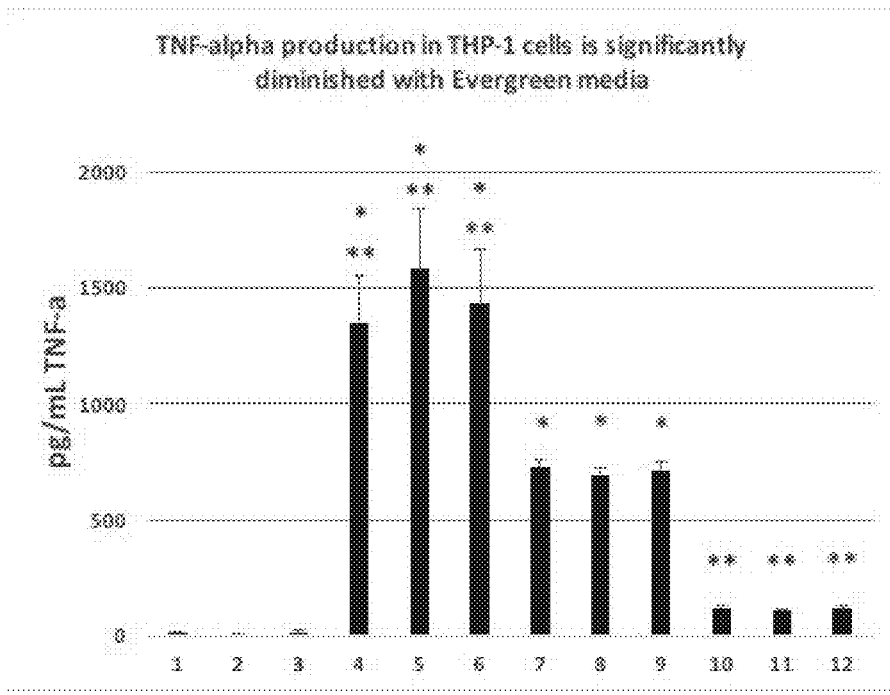
FIG. 14. TNF-alpha production in necroptosis-induced THP-1 cells was significantly diminished with a cryopreservation solution, EVERGREEN™ Media Solution (EVERGREEN™ Media Soln: 20 nM 5-((7-Chloro-1H-indol-3-yl)methyl)-3-methyl-2,4-irnidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; also known as EVERLAST™). ELISA assay results for TNF-alpha after THP-1 cells were cultured and induced by necrotic cell lysates combined with lipopolysaccharide (LPS) to produce pro-inflammatory cytokines. TNF-alpha levels (pg/mL) after mock stimulation (1-3), LPS stimulation alone (4-6), LPS stimulation in the presence of 10% the active level of EVERGREEN™ Media Solution used in the cryopreservation protocol (7-9), LPS stimulation in the presence of 100% active level of EVERGREEN™ Media Solution used in the cryopreservation protocol (10-12). (*) Significant difference (p<0.01) between mock (1-3) and LPS alone (4-6), and between LPS alone (4-6) and LPS+10% EVERGREEN™ Media Solution (7-9). (**) Significant difference (p<0.001) between LPS alone (4-6) and LPS+100% EVERGREEN™ Media Solution (10-12).

TELISA assay results for TNF-alpha after THP-1 cells were cultured and induced by necrotic cell lysates combined with lipopolysaccharide (LPS) to produce pro-inflammatory cytokines. FIG. 14 shows TNF-alpha levels (pg/mL) after mock stimulation (1-3), LPS stimulation alone (4-6), LPS stimulation in the presence of 10% the active level of EVERGREEN™ Media Solution used in the cryopreservation protocol (7-9), LPS stimulation in the presence of 100% active level of EVERGREEN™ Media Solution used in the cryopreservation protocol (10-12). (*) Significant difference ($p<0.01$) between mock (1-3) and LPS alone (4-6), and between LPS alone (4-6) and LPS+10% EVERGREEN™ Media Solution (7-9). (**) Significant difference ($p<0.001$) between LPS alone (4-6) and LPS+100% EVERGREEN™ Media Solution (10-12).

TNF-alpha production in necroptosis-induced THP-1 cells was significantly diminished with the EVERGREEN™ cryopreservation solution of the present invention.

Example 15

IL-6 Production in Encroptosis-Induced THP-1 Cells was Significantly Diminished with a Cryopreservation Solution IL-6 production in necroptosis-induced THP-1 cells was studied with respect to the effects of a cryopreservation solution of the present invention (EVERGREEN™ Media Soln: 20 nM ((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™).

Briefly, necrotic cell lysates were first generated and used in the assays for THP-1 cell cytokine production. Necrotic cell lysates were generated by taking THP-1 cells and culturing on 60 mm dishes in complete medium (RPMI 1640, supplemented with 2 mM glutamine, 10% fetal bovine serum, 100 U per mL penicillin, 100 µg/mL streptomycin) at 1-million cells per ml, and stimulating with 0.5 µg/mL of LPS, After ~12 h, the cells were collected, then washed briefly with PBS (2 times with 10× volume), then resuspended in complete medium at 1-million cells per mL. These cells were then used for necrosis induction by repeated (5-6 cycles) freezing with liquid nitrogen and thawing to 37'C. Lysates were made from these by centrifugation at 15K R.P.M. (24K×g) for 20 minutes at 4° C., and then added to freshly cultured THP-1 cells at a 50% volume/volume ratio with fresh medium. To this medium, LPS at 0.5 µg/mL was also added for maximum cytokine production. TNF-alpha and IL-6 protein concentrations were measured in the cultured supernatant using an ELISA kit (R&D Systems, Minneapolis, MN) following the manufacturers protocol. Each sample was assayed in duplicate, with standard known cytokine protein measurements as references. Data are mean of 3 independent experiments+standard error of the mean (S.E.M.). p values were calculated using the Students T-test.

Figure 15:
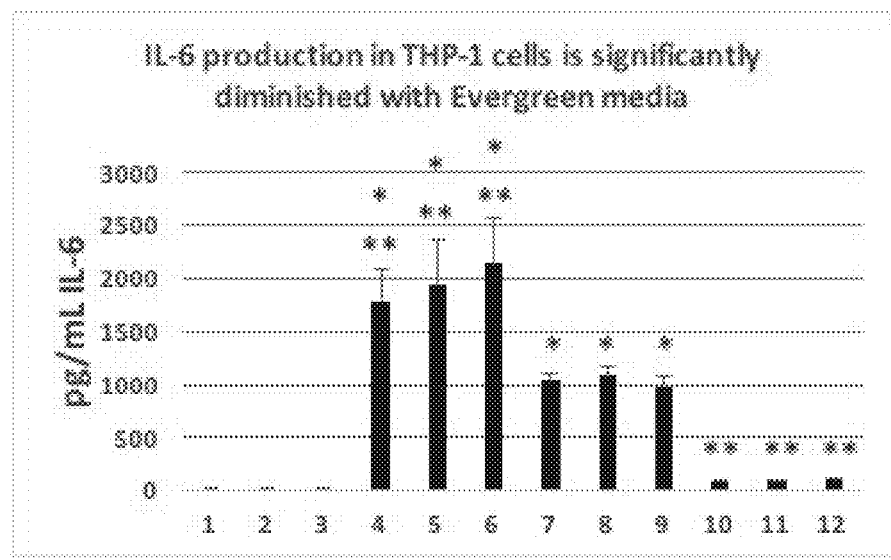
FIG. 15. IL-6 production in necroptosis-induced THP-1 cells was significantly diminished with a cryopreservation solution (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanoldihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; also known as EVERLAST™). ELISA assay results for 1L-6 after THP-1 cells were cultured and induced by necrotic cell lysates combined with lipopolysaccharide (LPS) to produce pro-inflammatory cytokines. IL-6 levels (pg/mL) measured after (1-3) mock stimulation, (4-6) LPS stimulation alone, (7-9) LPS stimulation in the presence of 10% the active level of EVERGREEN™ Media. Solution used in the cryopreservation protocol, (10-12) LPS stimulation in the presence of 100% active level of EVERGREEN™ Media Solution used in the cryopreservation protocol. (*) Significant difference (p<0.01) between mock (1-3) and LPS alone (4-6), and between LPS alone (4-6) and LPS+10% EVERGREEN™

ELISA assay results for IL-6 after THP-1 cells were cultured and induced by necrotic cell lysates combined with lipopolysaccharide (LPS) to produce pro-inflammatory cytokines, FIG. 15 shows IL-6 levels (pg/mL) measured after (1-3) mock stimulation, (4-6) LPS stimulation alone, (7-9) LPS stimulation in the presence of 10% the active level of EVERGREEN™ Media Solution used in the cryopreservation protocol, (10-12) LPS stimulation in the presence of 100% active level of EVERGREEN™ Media Solution used in the cryopreservation protocol. (*) Significant difference ($p<0.01$) between mock (1-3) and LPS alone (4-6), and between LPS alone (4-6) and LPS+10% EVERGREEN™ Media Solution (7-9). (**) Significant difference ($p<0.001$) between LPS alone (4-6) and LPS+100% EVERGREEN™ Media Solution (10-12).

IL-6 production in necroptosis-induced THP-1 cells was significantly diminished with the EVERGREEN™ cryopreservation solution of the present invention.

Example 16

Consistency of IL-6 Cytokine Release Measures Using a Cryopreservation Solution.

A cryopreservation solution of the present invention (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™) produced significant consistency in cytokine release measures (FIG. 16). Percent variability was calculated by averaging the percent errors of each (triplicate) experiment (n=3), and expressing each group's (stimulated, 10% EVERGREEN™, 100% EVERGREEN™) percent variability as a ratio to the mock (control) stimulated group variability. From this, there is ~100% increase in variability without the use of EVERGREEN™ (both at 10% and 100% levels).

Example 17

Consistency of Neuronal Cell Viability Post-Freeze-Thaw with a Cryopreservation Solution of the Present Invention Compared with a Conventional Cryopreservation Solution A cryopreservation solution of the present invention (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™) conferred significantly consistently greater neuronal viability post-freeze/thaw compared to DMSO, a conventional cryopreservation solution (FIG. 17). EVERGREEN™ Media Solution was used to freeze primary mouse hippocampal neurons compared to dimethyl sulfoxide (DMSO) and viability post-thaw was measured and plotted. Five independent experiments were measured.

Example 18

Consistency of Neuronal Cell Viability Post-Freeze-Thaw with a Cryopreservation Solution of the Present Invention Compared with a Conventional Cryopreservation Solution A cryopreservation solution of the present invention (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™) induced significant consistency in neuronal cell viability post-freeze/thaw compared to DMSO, a conventional cryopreservation solution (FIG. 18). Percent variability was calculated by averaging the means of each experiment (n=5) and expressing each group's individual measurement as a ratio of the individual value to the mean value. From this, the percent deviation was calculated and expressed as a ratio to the mean. From this, there is an ~300% increase in variability without the use of EVERGREEN™ Media Solution.

Example 19

Neuronal Cell Activity Maintained Post-Freeze-Thaw with a Cryopreservation Solution of the Present Invention The effects of freeze-thaw in a cryopreservation solution of the present invention (EVERGREEN™ Media Soln: 20 nM 5-((7-Chloro-1H-indol-3-yl)methyl)-3-methyl-2,4-imidazolidinedione), 5 nM 3,6-Dibromo-a-(1-piperazinylmethyl)-9H-carbazole-9-ethanol dihydrochloride, 0.05 mM nicotinamide adenine dinucleotide (NAD), 0.01 µM adenosine triphosphate (ATP), 0.01 µM cyclosporin A, and 0.1 Kuntz Unit manganese superoxide dismutase; EVERLAST™) on neuronal cell activity were studied.

Briefly, hippocampal neurons were either freshly dissected (before) or frozen with Evergreen media then thawed 48-72 hours later (after) and placed into cultures in vitro. Neuron cultures after 17-19 days in vitro were placed into the recording chamber upon the Zeiss Axiozoom stage and washed in standard recording medium. Neurons were recorded with patch clamp pipettes containing: 130 mM K-gluconate, pH 7.3, 10 mM Kcl, 0.1 mM EGTA, 5 mM NaCl, 10 mM HEPES, 0.3 mM sodium-GTP, and 5 mM phosphocreatine, 1 mM Mg-ATP (range of 5-10 MΩ resistance). Signals were amplified with AxoPatch 200A/AxoClamp2 amplifiers and recorded with pClamp8.

FIG. 19A shows hippocampal neurons from freshly dissected mouse brain showing whole cell current clamp (at resting membrane potential) recording demonstrates network activity in culture. Vertical bar represents 20 milliVolts (mV) magnitude and horizontal bar 2 seconds (sec) of recording. FIG. 19B shows hippocampal neuron from freshly dissected mouse brain after freeze/thaw using EVERGREEN™ Media Solution showing whole cell current clamp (at resting membrane potential) recording demonstrates network activity in culture. Vertical bar represents 20 milliVolts (mV) magnitude and horizontal bar 2 seconds (sec) of recording. FIG. 19C shows Cumulative frequency over 5 minutes recording interval for current clamp data showing average frequency of action potential discharges.

Values are mean+SE (standard error) of at least 4 independent experiments, which show no statistically significant differences (p>0.7, Student's t-test) either before or after freeze/thaw using EVERGREEN™ Media Solution.

FIG. 19D shows hippocampal neuron from freshly dissected mouse brain showing whole cell voltage clamp (at −60 mV) recording demonstrates network activity in culture. Vertical bar represents 200 picoAmps (pA) magnitude and horizontal bar 2 seconds (sec) of recording. FIG. 19E shows hippocampal neuron from freshly dissected mouse brain after freeze/thaw using EVERGREEN™ Media Solution showing whole cell voltage clamp (at −60 mV) recording demonstrates network activity in culture. Vertical bar represents 200 picoAmps (pA) magnitude and horizontal bar 2 seconds (sec) of recording. FIG. 19F shows cumulative frequency over 5 minutes recording interval for voltage clamp data showing average frequency of action potential discharges. Values are mean+SE (standard error) of at least 4 independent experiments, which show no statistically significant difference (p>0.8) either before or after freeze/thaw using EVERGREEN™ Media Solution.

FIG. 19G shows evoked pre-synaptic action potential shown (lower traces) in current clamp mode at resting potential and the post-synaptic excitatory synaptic response (upper traces) (shown on schematic at left as black circle at end of axon from lower presynaptic neuron) from two adjacent coupled hippocampal neurons, both before (left traces, freshly dissected) and after (right traces) freeze/thaw using EVERGREEN™ Media Solution. Here, the excitatory post synaptic currents (EPSCs) are not statistically different between treatments (actual values 71+/−23 pA before versus 76+/−28 pA after). Representative traces from n=19-22 neurons, at least 3 independent experiments for each treatment (p>0.7, Student's t-test). Vertical bar represents 20 picoAmps (pA) magnitude for current clamped neurons (pre-synaptic, lower traces) and 20 milliVolts (mV) for the excitatory synaptic responses (post-synaptic, upper traces); horizontal bar represents 20 milliSeconds (ms) of recording. FIG. 19H shows evoked action potential amplitude ratios for presynaptic over post-synaptic (pre/post) responses for 19 hippocampal neurons (as measured in part G) both before (closed circles) and after (open circles) freeze/thaw using EVERGREEN™ Media Solution. Average ratios are not statistically different for neurons before and after freeze/thaw using EVERGREEN™ Media Solution (p>0.7, Student's t-test) (average values 71+/−23 pA for before versus 76+/−28 pA for after freeze/thaw). X values correspond to neuron numbers for each treatment.

Therefore, hippocampal neurons show physiological characteristics that are indistinguishable from before (freshly dissected) and after freeze/thaw using Evergreen media. Patch clamp of embryonic day 17-19 neurons shows current and voltage profiles from both spontaneous and evoked neuronal activities.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A cryopreservation composition comprising:
   (a) about 0.2 nM to 2 µM of a necroptosis inhibitor compound selected from the group consisting of 5-(Indol-3-ylmethyl)-(2-thio-3-methyl)hydantoin (necrostatin-1, Nec-1), 5-((7-Chloro-1H-indol-3-yl)methyl)-3-methyl-2,4-imidazolidinedione (necrostatin-1s, Nec-1s), or an isomer thereof, or a pharmaceutically acceptable salt thereof;
   (b) about 0.5 nM to 50 µM of a Bax channel inhibitor compound selected from the group consisting of 3,6-dibromo-9-(2-fluoro-3-(piperazin-1-yl)propyl)-9H-carbazole, 3,6-Dibromo-a-(1-piperazinylmethyl)-9H-carbazole-9-ethanol, or an isomer thereof, or a pharmaceutically acceptable salt thereof; and
   (c) about 1 nM to 1 mM of cyclosporin A.

2. A cryopreservation composition of claim 1, wherein:
   (a) the necroptosis inhibitor compound is 5-((7-Chloro-1H-indol-3-yl)methyl)-3-methyl-2,4-imidazolidinedione (necrostatin-1s, Nec-1s), an isomer thereof, or a pharmaceutically acceptable salt thereof; and
   (b) the Bax channel inhibitor compound is 3,6-Dibromo-a-(1-piperazinylmethyl)-9H-carbazole-9-ethanol, an isomer thereof, or a pharmaceutically acceptable salt thereof.

3. A cryopreservation composition of claim 1, wherein the necroptosis inhibitor compound is 5-(Indol-3-ylmethyl)-(2-thio-3-methyl)hydantoin (necrostatin-1, Nec-1), or an isomer thereof, or a pharmaceutically acceptable salt thereof.

4. A cryopreservation composition of claim 1, wherein the cyclosporin A is at a concentration of about 1 nM to 1 mM.

5. A cryopreservation composition of claim 1, comprising:
   a) about 20 nM 5-((7-Chloro-1H-indol-3-yl)methyl)-3-methyl-2,4-imidazolidinedione;
   b) about 5 nM 3,6-dibromo-9-(2-fluoro-3-(piperazin-1-yl)propyl)-9H-carbazole dihydrochloride (iMAC2); and
   c) about 0.01 UM cyclosporin A.

6. The caspase-independent cryopreservation composition of claim 1, further comprising a cryoprotective agent.

7. The caspase-independent cryopreservation composition of claim 6, wherein said cryoprotective agent comprises DMSO, or serum, or any combination thereof.

8. The caspase-independent cryopreservation composition of claim 1, further comprising pharmaceutically acceptable excipients or carriers.

9. A method of cryopreservation comprising contacting one or more cells, tissues, organs or organisms, with a cryopreservation composition of claim 1.

10. A method of treating, preventing, inhibiting, or reducing the incidence of cellular plasticity, or necroptosis, or necrosis in one or more cells, tissues, organs or organisms, comprising administering a cryopreservation composition of claim 1 to the cells, tissues, organs or organisms.

11. The method of claim 10, wherein said necroptosis or necrosis is associated with aging or disease.

12. The method of claim 11, wherein said disease is myocardial infarction, diabetes secondary to beta-cell necroptosis, cholestatic liver disease, stroke, organ ischemia, ischemia-reperfusion injury, liver disease, necrosis from cancer chemotherapy or radiation therapy, traumatic brain injury, necrotizing pancreatitis, pathogen-induced necroptosis, inflammation, or neurodegenerative disease.

13. The method of claim 10, wherein said treating, preventing, inhibiting, or reducing the incidence of cellular plasticity, or necroptosis or necrosis, comprises in vitro or in vivo or ex vivo treating, preventing, inhibiting, or reducing the incidence of cellular plasticity, necroptosis, or necrosis.

14. The method of claim 10, wherein the one or more cells comprise tissue culture cells, primary cells, egg cells, a tissue, or organ or a portion thereof, or any combination thereof.

15. The method of claim 14, wherein said tissue culture cells or primary cells comprise stem cells, adult cells, transdifferentiated cells, dedifferentiated cells, or differentiated cells, or any combination thereof.

16. The method of claim 10, wherein the one or more cells comprise human cells or animal cells.

17. The method of claim 10, wherein the method is an in vivo, ex vivo, or in vitro method.

18. The method of claim 17, wherein the in vivo, ex vivo method comprises perfusion of an animal or a portion thereof, an organ or a portion thereof, or a tissue.

19. The method of claim 18, wherein said perfusion is cardiac perfusion.

20. The method of claim 10, further comprising the step of physical, chemical, or thermodynamic manipulation of said one or more cells.

21. The method of claim 20, wherein the thermodynamic manipulation comprises heating or cooling said one or more cells.

22. The method of claim 21, wherein said cooling comprises cryopreservation or a freeze-thaw cycle, or a combination thereof.

23. The method of claim 10, wherein:
(a) the concentration of 5-((7-Chloro-1H-indol-3-yl)methyl)-3-methyl-2,4-imidazolidinedione, an isomer thereof, or a pharmaceutically acceptable salt thereof, is about 20 nM;
(b) the concentration of 3,6-Dibromo-a-(1-piperazinylmethyl)-9H-carbazole-9-ethanol, an isomer thereof, or a pharmaceutically acceptable salt thereof, is about 5 nM; and
(c) the concentration of the cyclosporin A is about 0.01 μM.

24. The method of claim 10, wherein the composition further comprises a cryoprotective agent.

25. The method of claim 24, wherein said cryoprotective agent comprises DMSO, or serum, or any combination thereof.

26. The method of claim 10, wherein the composition further comprises a pharmaceutically acceptable carriers or excipients.

27. The cryopreservation composition of claim 1, comprising:
(a) about 20 nM 5-((7-Chloro-1H-indol-3-yl)methyl)-3-methyl-2,4-imidazolidinedione, an isomer thereof, or a pharmaceutically acceptable salt thereof;
(b) about 5 nM 3,6-Dibromo-a-(1-piperazinylmethyl)-9H-carbazole-9-ethanol, an isomer thereof, or a pharmaceutically acceptable salt thereof; and
(c) about 1 nM to 1 mM cyclosporin A.

* * * * *